United States Patent

Matsumoto et al.

Patent Number: 5,266,707
Date of Patent: Nov. 30, 1993

[54] 3,5-DIHYDROXYHEPTANOIC ACID DERIVATIVES

[75] Inventors: Masakatsu Matsumoto, Sagamihara; Nobuko Watanabe, Kamakura; Eiko Mori, Kodaira; Tetsuaki Yamaura, Niiza; Misao Aoyama, Fussa, all of Japan

[73] Assignee: Fujirebio Inc., Tokyo, Japan

[21] Appl. No.: 946,533

[22] Filed: Sep. 17, 1992

[30] Foreign Application Priority Data

Sep. 18, 1991 [JP] Japan .................. 3-265405

[51] Int. Cl.$^5$ ............... C07D 309/30; C07D 307/79; C07D 307/80
[52] U.S. Cl. .................. 549/292; 546/148; 546/167; 546/196; 546/269; 544/153; 544/149; 548/454; 548/491; 548/525; 548/311.4; 549/60; 549/462; 549/467; 549/472; 549/473
[58] Field of Search ............. 549/292, 462, 467, 472, 549/473, 60; 544/153, 149; 546/148, 167, 196, 269; 548/336, 454, 491, 525

[56] References Cited

U.S. PATENT DOCUMENTS 5,149,834  9/1992  Matumoto et al. .............. 549/292

FOREIGN PATENT DOCUMENTS 0455827  9/1991  European Pat. Off. .

Primary Examiner—C. Warren Ivy
Assistant Examiner—Ba K. Trinh
Attorney, Agent, or Firm—Oblon, Spivak, McClelland, Maier & Neustadt

[57] ABSTRACT

4-hydroxytetrahydropyran-2-one and 3,5-Dihydroxyheptanoic acid derivatives of formula (I) and formula (II) have an inhibition effect on HMG-CoA reductase, a cholesterol value reduction effect, and an antioxidation function, thus serving as cholesterol reducing agent or lipid reducing agents:

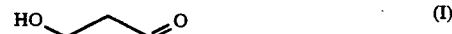

(I)

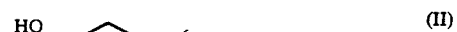

(II)

wherein $R^1$ represents hydrogen, a nitro group, or $-N(R^4)R^5$ in which $R^4$ and $R^5$ each represent an alkyl group, an alkenyl group, an aryl group, an aralkyl group; an acyl group, an aroyl group, a carbamoyl group, or a thiocarbamoyl group, and $R^4$ and $R^5$ may be combined to form a cyclic amino group; and $R^2$ and $R^3$ each represent hydrogen or an alkyl group; and $R^6$ represents hydrogen, an alkyl group, an alkali metal, or an alkaline earth metal.

17 Claims, No Drawings

3,5-DIHYDROXYHEPTANOIC ACID DERIVATIVES

BACKGROUND OF THE INVENTION

1. Field of the Invention

The present invention relates to 4-hydroxytetrahydropyran-2-one and 3,5-dihydroxyheptanoic acid derivatives, which are useful as cholesterol reducing agents as well as lipid reducing agents since the 4-hydroxytetrahydropyran-2-one and 3,5-dihydroxyheptanoic acid derivatives have a strong inhibition of effect on 3-hydroxy-3-methyl-glutaryl-coenzyme A reductase (hereinafter referred to as HMG-CoA reductase).

The present invention alto relates to intermediates for synthesizing the above derivatives which are useful as cholesterol reducing agents or lipid reducing agents.

2. Discussion of Background

As a remedy for reducing blood cholesterol which works as one of significant factors relating to the development of arteriosclerosis, ML-236B has been discovered which inhibits the biosynthesis of cholesterol by the competitive inhibition of the effect of HMG-CoA reductase, which serves as a rate-determining enzyme for the formation of cholesterol, thereby reducing the level of the blood cholesterol (refer to Japanese Laid-Open Patent Application 50-155690). ML-236B is a compound having a 6-substituted-4-hydroxytetrahydropyran-2-one skeleton. After the discovery of the ML-236B, various compounds with a 4-hydroxytetrahydropyran-2-one skeleton, having a blood-lipid-reducing effect, have been proposed (refer to T.-J. Lee, Trends in Pharmacol. Scie., 8 (1), 4420 (1987), and Drugs of the Future 12 (5), (1987)).

Furthermore, it is considered that a compound which has an antioxidation effect and therefore inhibits the formation of peroxidized lipids will also be useful as a remedy for arteriosclerosis, and it is reported that vitamin E and probucol have such effects.

SUMMARY OF THE INVENTION

It is therefore an object of the present invention to provide 4-hydroxytetrahydropyran-2-one and 3,5-dihydroxyheptanoic acid derivatives which have an HMG-COA reductase inhibition effect, thereby significantly lowering the blood cholesterol level in vital bodies, and an antioxidation effect, thereby inhibiting the formation of peroxidized lipids like vitamin E.

This object of the present invention can be achieved by 4-hydroxytetrahydropyran-2-one derivatives with the following general formula (I):

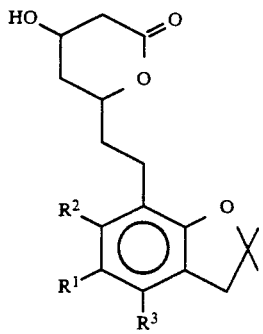

wherein R represents hydrogen, a nitro group, or -N(R$^4$)R$^5$ in which R$^4$ and R$^5$ each represent a straight chain or branched chain alkyl group having 1 to 5 carbon atoms; an alkenyl group having 2 to 5 carbon atoms; an aryl group such as furyl group, thienyl group, pyrrolyl group, phenyl group, and pyridyl group; an aralkyl group such as benzyl group, phenethyl group, phenylpropyl group, naphthylmethyl group, furfuryl group, and thienylmethyl group; an acyl group having 2 to 5 carbon atoms; an aroyl group such as benzoyl group, pyridinecarbonyl group, imidazolylcarbonyl group, furoyl group, and thiophenecarbonyl group; a carbamoyl group; or a thiocarbamoyl group, and R$^4$ and R$^5$ may be combined to form a cyclic amino group; and R$^2$ and R$^3$ each represent hydrogen or a straight chain or branched chain alkyl group having 1 to 5 carbon atoms.

The above object of the present invention can also be achieved by 3,5-dihydroxyhepanoic acid represented by the following formula (II):

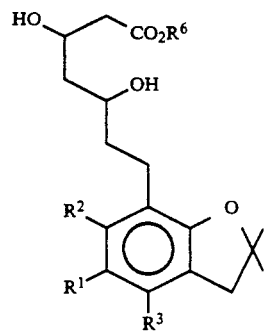

wherein R$^1$, R$^2$, R$^3$, R$^4$ and R$^5$ are respectively the same as those in formula (I); and R$^6$ represents hydrogen, a straight chain or branched chain alkyl group having 1 to 5 carbon atoms, an alkali metal, or an alkaline earth metal.

DETAILED DESCRIPTION OF THE PREFERRED EMBODIMENTS

In the 4-hydroxytetrahydropyran-2-one derivatives of the invention having the previously mentioned formula (i), R$^1$ represents hydrogen, a nitro group, or -N(R$^4$)R$^5$ in which R$^4$ and R$^5$ each represent a straight chain or branched chain alkyl group having 1 to 5 carbon atoms; an alkenyl group having 2 to 5 carbon atoms; an aryl group; an aralkyl group; an acyl group having 2 to 5 carbon atoms; an aroyl group; a carbamoyl group; or a thiocarbonyl group, and R$^4$ and R$^5$ may be combined to form a cyclic amino group, and R$^2$ and R$^3$ each represent hydrogen or a straight chain or branched chain alkyl group having 1 to 5 carbon atoms.

Specific examples of the alkyl group having 1 to 5 carbon atoms represented by R$^4$ and R$^5$ are methyl group, ethyl group, propyl group, isopropyl group, butyl group, isobutyl group, s-butyl group, t-butyl group, and pentyl group.

Specific examples of the alkenyl group having 2 to 5 carbon atoms represented by R$^4$ and R$^5$ are ethylene group, 1-propenyl group, 2-propenyl group, 2-methyl-1-propenyl group, 2-methyl-2-propenyl group, 1-butenyl group, 2-butenyl group, 3-butenyl group, and phenyl group.

Examples of the aryl group represented by R$^4$ and R$^5$ are furyl group, thienyl group, pyrrolyl group, phenyl group, and pyridyl group.

Examples of the aralkyl group represented by $R^4$ and $R^5$ are benzyl group, phenethyl group, phenylpropyl group, naphthylmethyl group, furfuryl group, and thienylmethyl group.

Specific examples of the acyl group having 2 to carbon atoms represented by $R^4$ and $R^5$ are acetyl group, propionyl group, butyryl group, isobutyryl group, and pivaloyl group.

Examples of the aroyl group represented by $R^4$ and $R^5$ are benzoyl group, pyrydinecarbonyl group, imidazolylcarbonyl group, furoyl group, and thiophenecarbonyl group.

The carbamoyl group represented by $R^4$ and $R^5$ may have a substituent. Examples of the substituted carbamoyl group represented by $R^4$ and $R^5$ are methylcarbamoyl group, dimethylcarbamoyl group, ethylcarbamoyl group, diethylcarbamoyl group, phenylcarbamoyl group, and cyclohexylcarbamoyl group.

The thiocarbamoyl group represented by $R^4$ and $R^5$ may also have a substituent. Examples of the substituted thiocarbamoyl group represented by $R^4$ and $R^5$ are methylthiocarbamoyl group, dimethylthiocarbamoyl group, ethylthiocarbamoyl group, diethylthiocarbamoyl group, phenylthiocarbamoyl group, and cyclohexylthiocarbamoyl group.

Examples of the cyclic amino group formed by $R^4$ and $R^5$ in combination are pyrrolidin-1-yl group, piperidino group, morpholino group, isoindolin-2-yl group, isoindolyl group, and 1,2,3,4-tetrahydroisoquinolin-2-yl group.

Furthermore, $R^1$, $R^2$, and $R^3$ of the 3,5-dihydroxyheptanoic acid derivatives represented by the previously mentioned general formula (II) are the same as those of the 4-hydroxytetrahydropyran-2-one derivatives represented by the previously mentioned general formula (I). $R^6$ represents hydrogen, a straight chain or branched chain alkyl group having 1 to 5 carbon atoms, an alkali metal, or an alkaline earth metal. The alkyl group represented by $R^6$ may be the same as those of the alkyl group represented by $R^1$.

Specific examples of the alkali metal are lithium, sodium, and potassium. Specific examples of the alkaline earth metal are magnesium, calcium, and barium.

The 4-hydroxytetrahydropyran-2-one and 3,5-dihydroxyheptanoic acid derivatives of the present invention, which are represented by the previously mentioned formulas (I) and (II) can be prepared in accordance with the following respective reaction schemes:

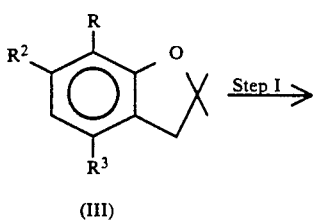

(III)

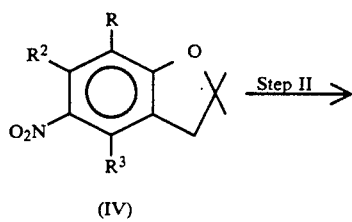

(IV)

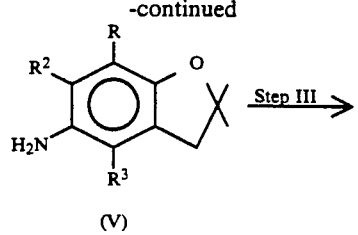

(V)

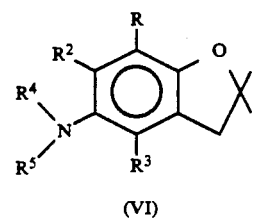

(VI)

wherein R represents (a) 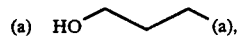

(b) 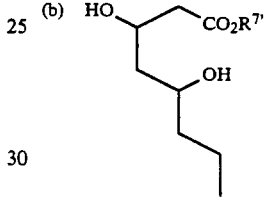

or (c) 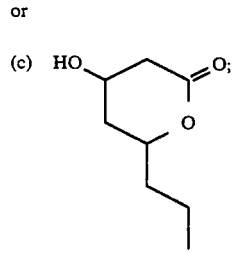

$R^2$, $R^3$, $R^4$, and $R^5$ are respectively the same as those previously defined formulas (I) and (II); and $R^7$ represents an alkyl group having 1 to 5 carbon atoms.

The compounds represented by the above-mentioned formulas (III-b), (III-c), (IV-b), (IV-c), (V-b), (V-c), (VI-b), and (VI-c) are within the scope of the compounds represented by the previously mentioned formulas (I) and (II).

[Step I]

In this step, a benzofuran derivative of formula (III) is nitrated, so that a nitro derivative of formula (IV) is produced.

The reaction can be carried out by use of a conventionally known nitration reagent or solvent such as nitric acid, a mixture of nitric acid and sulfuric acid, a mixture of concentrated nitric acid and anhydrous acetic acid (acetyl nitrate), a mixture of nitric acid and acetic acid, a mixture of cupric nitrate and anhydrous acetic acid, or a mixture of nitric acid and nitro methane.

The benzofuran derivatives represented by the general formula (III) can be produced, for example, in accordance with the following reaction scheme. A phenol derivative represented by general formula (VII) are commercially available, or can be easily produced from a commercially available starting material.

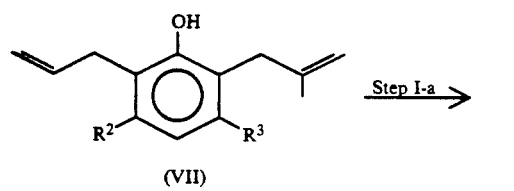
(VII)

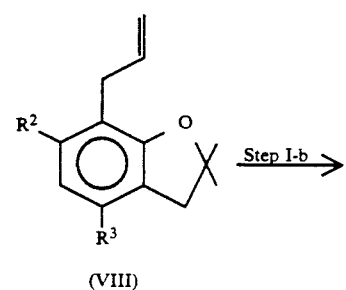
(VIII)

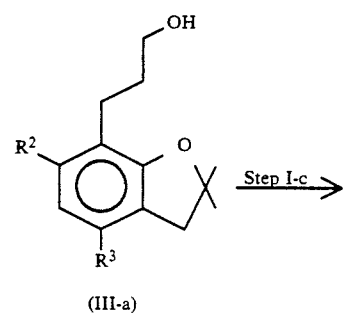
(III-a)

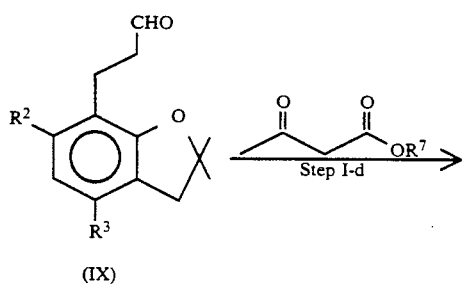
(IX)

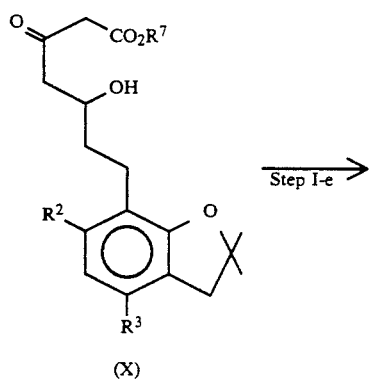
(X)

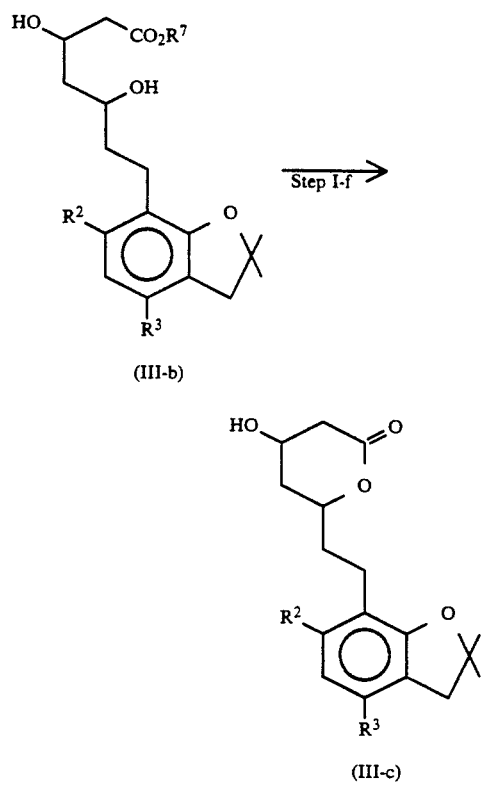
(III-b)

(III-c)

wherein $R^2$, $R^3$ and $R^7$ are respectively the same as those defined previously.

[Step I-a]

In this step, a phenol derivative represented by formula (VII) is subjected to a cyclization in the presence of an acid, so that a propene derivative represented by formula (VIII) is produced. $R^2$ and $R^3$ in the formula (VIII) are respectively the same as those defined previously.

As mentioned above, this reaction can be carried out in the presence of an acid such as boron trifluoride etherate, p-toluenesulfonic acid, or hydrochloric acid. In this step, the acid is employed in a catalytic amount to the phenol derivative represented by the previously mentioned general formula (VII).

It is preferable that this step be carried out in an inert solvent in an atmosphere of an inert gas. Specific examples of the inert solvent are halogenated hydrocarbons such as methylene chloride, chloroform, and 1,2-dichloroethane; esters such as ethyl acetate; and aromatic hydrocarbons such as benzene, toluene, and xylene. The reaction can be carried out at a temperature in the range of −5° to −150° C.

[Step I-b]

In this step, an alcohol derivative represented by formula (III-a) is produced by subjecting the propene derivative of the formula (VIII) obtained in Step I-a to hydroboration by use of a boran derivative, followed by the oxidation thereof.

As the boran derivative for use in this step, diboran, and a dialkylboran represented by 9-borabicyclo[3.3.1-]nonane (9-BBN) are usable. Of these boran derivatives, 9-BBN is preferable for use in this reaction. It is preferable that the boran derivative be employed in an amount of 1 to 2 equivalents to one equivalent of the propene derivative represented by the formula (VIII). The reaction can be preferably carried out in an atmosphere of an inert gas in an inert solvent. As such inert solvents, for example, ethers such as diethyl ether, THF and dioxane can be used. The reaction can proceed at a temperature in the range of 0° C to 100° C. The oxidation of the produced boron compound to produce a corresponding alcohol can be preferably performed by use of a conventionally employed alkaline hydrogen peroxide.

Examples of the benzofuran derivatives represented by the formula (III-a) are as follows:
3-[2,3-dihydro-2,2,4-trimethylbenzo[b]furan-7-yl]propanol,
3-[2,3-dihydro-2,2-dimethyl-4-(propan-2-yl)benzo[b]furan-7yl-]propanol,
3-[2,3-dihydro-2,2,4,6-tetramethylbenzo[b]furan-7-yl]propanol,
3-[2,3-dihydro-2,2,6-trimethyibenzo[b]furan-7-yl]propanol,
3-[2,3-dihydro-2,2,6-trimethyl-4-(propan-2-yl)benzo[b]furan-7-yl]propanol,
3-[4-(t-butyl)-2,3-dihydro-2,2,6-trimethylbenzo[b]furan-7-yl]propanol,
3-[2,3-dihydro-2,2-dimethyl-6-(propan-2-yl)benzo[b]furan-7-yl]propanol,
3-[2,3-dihydro-2,2,4-trimethyl-6-(propan-2-yl)benzo[b]furan-7-yl]propanol,
3-[6-(t-butyl)-2,3-dihydro-2,2-dimethylbenzo[b]furan-7-yl]propanol, and
3-[6-(t-butyl)-2,3-dihydro-2,2,4-trimethylbenzo[b]furan-7-yl]propanol.

[Step I-c]

In this step, an aldehyde derivative of formula (IX) is produced by oxidizing the alcohol derivative of the formula (III-a) obtained in Step I-b. As an oxidizing agent for use in this reaction, any oxidizing agents which oxidize hydroxyl group to aldehyde group can be employed. Specifically, chromium compounds such as pyridinium chlorochromate, sulfur trioxide pyridine complex, and N-chlorosuccinimide can be used.

The reaction can be preferably carried out in an atmosphere of an inert gas in an inert solvent. As such a solvent, for example, ethers such as diethyl ether, THF, and dioxane; halogenated hydrocarbons such as methylene chloride, chloroform, and 1,2-dichloroethane; dimethylformamide; and dimethyl sulfoxide can be employed. The reaction can be carried out at a temperature in the range of 0° C to 100° C.

[Step I-d]

In this step, the aldehyde derivative of the formula (IX) obtained in Step I-c is allowed to react with acetoacetic acid ester to produce a ketoester derivative represented by formula (X).

$R^7$ in the ketoester derivative represented by the formula (X) is an alkyl group having 1 to 5 carbon atoms, such as methyl group, ethyl group, propyl group, and butyl group.

Examples of the acetoacetic acid ester for use in this step are methyl acetoacetate, ethyl acetoacetate, propyl acetoacetate, and butyl acetoacetate. Examples of a base to derive a dianion of the acetoacetic ester are sodium hydride and butyl lithium.

It is preferable that the reaction be carried out in an atmosphere of an inert gas in an inert solvent. As such a solvent, for example, ethers including diethyl ether, THF, dioxane and dimethoxyethane may be used alone or in combination. The reaction can be carried out at a temperature in the range of −78° to room temperature.

[Step I-e]

In this step, the ketoester derivative represented by the formula (X) obtained in Step I-d is reduced to produce a 3,5-dihydroxyheptanoic acid ester derivative represented by formula (III-b). For the reduction in this step, a variety of reductants for reducing carbonyl group can be used. Specifically, sodium borohydride can be employed.

To carry out this step, the reductant is used in an amount of 1 to 6 equivalents, preferably 1 to 4 equivalents, to one equivalent of the ketoester derivative of the formula (X) to synthesize the 3,5-dihydroxyheptanoic acid ester derivative of the formula (III-b). Furthermore, the reaction can be carried out by the addition of a trialkylborane such as trimethylborane or triethylborane, or pivalic acid to improve the steric selectiveness.

The reaction is usually carried out in an inert solvent, for example, in water; alcohols such as methanol, ethanol, and butanol; ethers such as THF and dioxane; halogenated hydrocarbons such as methylene chloride and 1,2-dichloroethane; or aromatic hydrocarbons such as benzene and toluene. These solvents can be used alone or in combination. The reaction can usually be carried out at a temperature in the range of −78° C. to room temperature.

Examples of the benzofuran derivatives represented by the previously mentioned general formula (III-b) are as follows:
ethyl 7-[2,3-dihydro-2,2,4-trimethylbenzo[b]furan-7-yl]-3,5-dihydroxyheptanoate,
ethyl 7-[2,3-dihydro-2,2-dimethyl-4-(propan-2-yl)benzo[b]furan-7-yl]-3,5-dihydroxyheptanoate,
ethyl 7-[2,3-dihydro-2,2,4,6-tetramethylbenzo[b]furan-7-yl]-3,5-dihydroxyheptanoate,
ethyl 7-[2,3-dihydro-2,2,6-trimethylbenzo[b]furan-7-yl]-3,5-dihydroxyheptanoate,
ethyl 7-[2,3-dihydro-2,2,6-trimethyl-4-(propan-2-yl)benzo[b]furan-7-yl]-3,5-dihydroxyheptanoate,
ethyl 7-[4-(t-butyl)-2,3-dihydro-2,2,6-trimethylbenzo[b]furan-7-yl]-3,5-dihydroxyheptanoate,
ethyl 7-[2,3-dihydro-2,2-dimethyl-6-(propan-2-yl)benzo[b]furan-7-yl]-3,5-dihydroxyheptanoate,
ethyl 7-[2,3-dihydro-2,2,4-trimethyl-6-(propan-2-yl)benzo[b]furan-7-yl]-3,5-dihydroxyheptanoate,
ethyl 7-[6-(t-butyl)-2,3-dihydro-2,2-dimethylbenzo[b]furan-7-yl]-3,5-dihydroxyheptanoate, and
ethyl 7-[6-(t-butyl)-2,3-dihydro-2,2,4-trimethylbenzo[b]furan-7-yl]-3,5-dihydroxyheptanoate.

[Step I-f]

In this step, the 3,5-dihydroxyheptanoic acid ester derivative represented by the formula (III-b) obtained in Step I-e is hydrolyzed by use of a base to produce a hydroxyheptanoic acid derivative having a carboxyl group, and this hydroxyheptanoic acid derivative is then subjected to cyclization with application of heat thereto, so that a 4-hydroxytetrahydropyran-2-one derivative represented by formula (III-c) is produced.

As the base for use in the hydrolysis in this step, hydroxides of alkali metals and alkaline earth metals such as sodium hydroxide, potassium hydroxide, calcium hydroxide and barium hydroxide are used.

In this step, the base is employed in an amount of 1 to 3 equivalents, preferably in an amount of 1.5 to 2 equivalents, to one mole of the 3,5-dihydroxyheptanoic acid ester derivative represented by the formula (III-b).

The reaction can usually be carried out in water, or a mixed solvent of water and a water-miscible solvent such as methanol and ethanol at a temperature in the range of 0° to 80° C.

Furthermore, from the hydroxyheptanoic acid derivative obtained by hydrolysis, the 4-hydroxytetrahydropyran-2-one derivative represented by the formula (III-c) can be obtained without isolating the hydroxyheptanoic acid derivative. The reaction can be carried out in an inert solvent, for example, in an aromatic hydrocarbon solvent such as toluene, xylene, halogenated hydrocarbons such as methylene chloride and chloroform, or esters such as ethyl acetate, and a mixed solvents of these, under a neutral or acidic condition. The reaction can usually be carried out at a temperature in the range of 40° to 150° C. In the case where that the above reaction is carried out under an acidic condition, acids such as trifluoroacetic acid and p-toluene sulfonic acid can be used to obtain the acidic condition.

Examples of the benzofuran derivatives represented by the previously mentioned general formula are as follows:

trans-(±)-6-[2,3-dihydro-2,2,4-trimethylbenzo[b]furan-7-yl]ethyl-4-hydroxytetrahydropyran-2-one, trans-(±)-6-[2,3-dihydro-2,2-dimethyl-4-(propan-2-yl)benzo[b]furan-7-yl]ethyl-4-hydroxytetrahydropyran-2-one, trans-(±)-6-[2,3-dihydro-2,2,4,6-tetramethylbenzo[b]furan-7-yl]ethyl-4-hydroxytetrahydropyran-2-one, trans-(±)-6-[2,3-dihydro-2,2,6-trimethylbenzo[b]furan-7-yl]ethyl-4-hydroxytetrahydropyran-2-one, trans-(±)-6-[2,3-dihydro-2,2,6-trimethyl-4-(propan-2-yl)benzo[b]furan-7-yl]ethyl-4-hydroxytetrahydropyran-2-one, trans-(±)-6-[4-(t-butyl)-2,3-dihydro-2,2,6-trimethylbenzo[b]furan-7-yl]ethyl-4-hydroxytetrahydropyran-2-one, trans-(±)-6-[2,3-dihydro-2,2-dimethyl-6-(propan-2-yl)benzo[b]furan-7-yl]ethyl-4-hydroxytetrahydropyran-2-one, trans-(±)-6-[2,3-dihydro-2,2,4-trimethyl-6-(propan-2-yl)benzo[b]furan-7-yl]ethyl-4-hydroxytetrahydropyran-2-one, trans-(±)-6-[6-(t-butyl)-2,3-dihydro-2,2-dimethylbenzo[b]furan-7-yl]ethyl-4-hydroxytetrahydropyran-2-one, and trans-(±)-6-[6-(t-butyl)-2,3-dihydro-2,2,4-trimethylbenzo[b]furan-7-yl]ethyl-4-hydroxytetrahydropyran-2-one.

When the nitro compound represented by the formula (IV-b) synthesized in Step I is subjected to the same hydrolysis reaction as in Step I-f to produce a 3,5-dihydroxyheptanoic acid derivative having a nitro group, and the thus obtained 3,5-dihydroxyheptanoic acid derivative is then subjected to a cyclization, the nitro compound represented by the formula (IV-c) can be synthesized.

In addition, when the amine compound represented by the formula (V-b) synthesized in Step II is subjected to the same hydrolysis reaction and cyclization as the above, the amine compound represented by the formula (V-c) can be synthesized.

Furthermore, when the substituted amine compound represented by the formula (IV-b) synthesized in Step III is subjected to the same hydrolysis reaction and cyclization as the above, the substituted amine compound represented by the formula (IV-c) can also be synthesized.

[Step II]

In this step, the nitro derivative represented by the previously mentioned formula (IV) is reduced, so that an amine derivative represented by the formula (V) is produced.

As the reduction for use in this step, for instance, a catalytic reduction may be used. In an atmosphere of hydrogen, conventionally known catalysts such as platinum, platinum oxide, platinum black, palladium on carbon (Pd-C), Raney nickel, and a combination of sodium borohydride and palladium on carbon can be used.

It is preferable that the reaction in Step II be carried out in an inert solvent. As the inert solvent, for instance, water; alcohols such as methanol and ethanol; and acetic acids can be employed. These inert solvents may be used alone or in combination.

[Step III]

In this step, a substituted amine derivative represented by the previously mentioned formula (VI) is produced by use of the amine derivative represented by the formula (V).

The substituted amine derivative represented by the formula (VI) can be synthesized by allowing the amine derivative of the formula (V) to react with a respectively corresponding alkyl halide, alkenyl halide, aralkyl halide, acyl halide, aroyl halide, isothiocyanate, or isocyanate.

It is preferable that the reaction in Step III be carried out in an inert solvent. As the inert solvent, for instance, ethers such as diethyl ether, dioxane, THF, dimethoxyethane; alcohols such as methanol, ethanol, propanol; ketones such as acetone, and methyl ethyl ketone; and amides such as dimethylformamide, dimethylacetoamide, and N-methylpyrrolidone can be employed. These inert solvents may be used alone or in combination.

It is also preferable that a base be used in order to efficiently carry out the reaction between the amine derivative represented by the previously mentioned general formula (V) and alkyl halide, alkenyl halide, aralkyl halide, acyl halide, or aroyl halide.

Examples of the base employed in this reaction are alkali metal hydroxides such as sodium hydroxide and potassium hydroxide; alkali metal salts such as potassium carbonate, sodium carbonate, potassium hydrogencarbonate and sodium hydrogencarbonate; and organic bases such as triethylamine, pyridine and picoline.

Examples of the substituted amine derivatives represented by the previously mentioned general formula (VI-b) in this step are as follows:

ethyl 7-[2,3-dihydro-5-methylamino-2,2,4,6-tetramethylbenzo[b]furan-7-yl]-3,5-dihydroxyheptanoate, ethyl 7-[2,3-dihydro-2,2,4-trimethyl-5-methylamino-6-(propan-2-yl)benzo[b]furan-7-yl)-3,5-dihydroxyheptanoate, ethyl 7-[2,3-dihydro-2,2,4,6-tetramethyl-5-dimethylaminobenzo[b]furan-7-yl]-3,5-dihydroxyheptanoate, ethyl 7-[2,3-dihydro-2,2,4-trimethyl-5-dimethylamino-6-(propan-2-yl)benzo[b]furan-7-yl]-3,5-dihydroxyheptanoate, ethyl 7-[2,3-dihydro-5-(isoindolin-2-yl)-2,2,4,6-tetramethylbenzo[b]furan-7-yl]-3,5-dihydroxyheptanoate,
ethyl 7-[2,3-dihydro-5-(isoindolin-2-yl)-2,2,4-trimethyl-6-(propan-2-yl)benzo[b]furan-7-yl]-3,5-dihydroxyheptanoate,
ethyl 7-[2,3-dihydro-5-isoindolyl-2,2,4,6-tetramethylbenzo[b]furan-7-yl]-3,5-dihydroxyheptanoate,
ethyl 7-[2,3-dihydro-5-isoindolyl-2,2,4-trimethyl-6-(propan-2-yl)benzo[b]furan-7-yl]-3,5-dihydroxyheptanoate,
ethyl 7-[2,3-dihydro-2,2,4,6-tetramethyl-5-(pyrrolidin-1-yl)benzo[b]furan-7-yl]-3,5-dihydroxyheptanoate,
ethyl 7-[2,3-dihydro-2,2,4-trimethyl-5-(pyrrolidin-1-yl)-6-(propan-2-yl)benzo[b]furan-7-yl]-3,5-dihydroxyheptanoate,
ethyl 7-[2,3-dihydro-2,2,4,6-tetramethyl-5-piperidinobenzo[b]furan-7-yl]-3,5-dihydroxyheptanoate,
ethyl 7-[2,3-dihydro-2,2,4,-trimethyl-5-piperidino-6-(propan-2-yl)benzo[b]furan-7-yl]-3,5-dihydroxyheptanoate,
ethyl 7-[5-benzylamino-2,3-dihydro-2,2,4,6-tetramethylbenzo[b]furan-7-yl]-3,5-dihydroxyheptanoate,
ethyl 7-[5-benzylamino-2,3-dihydro-2,2,4-trimethyl-6-(propan-2-yl)benzo[b]furan-7-yl]-3,5-dihydroxyheptanoate,
ethyl 7-[5-(N-benzyl-N-methylamino)-2,3-dihydro-2,2,4,6-tetramethylbenzo[b]furan-7-yl]-3,5-dihydroxyheptanoate,
ethyl 7-[5-(N-benzyl-N-methylamino)-2,3-dihydro-2,2,4-trimethyl-6-(propan-2-yl)benzo[b]furan-7-yl]-3,5-dihydroxyheptanoate,
ethyl 7-[5-dibenzylamino-2,3-dihydro-2,2,4,6-tetramethylbenzo[b]furan-7-yl]-3,5-dihydroxyheptanoate,
ethyl 7-[5-dibenzylamino-2.3-dihydro-2,2,4-trimethyl-6-(propan-2-yl)benzo[b]furan-7-yl]-3,5-dihydroxyheptanoate,
ethyl 7-[2,3-dihydro-5-(1,2,3,4-tetrahydroisoquinolin-2-yl)-2,2,4,6-tetramethylbenzo[b]furan-7-yl]-3,5-dihydroxyheptanoate,
ethyl 7-[2,3-dihydro-5-(1,2,3,4-tetrahydroisoquinolin-2-yl)-2,2,4-trimethyl-6-(propan-2-yl)benzo[b]furan-7-yl]-3,5-dihydroxyheptanoate,
ethyl 7-[5-acetoamino-2,3-dihydro-2,2,4,6-tetramethylbenzo[b]furan-7-yl]-3,5-dihydroxyheptanoate,
ethyl 7-[5-acetoamino-2,3-dihydro-2,2,4-trimethyl-6-(propan-2-yl)benzo[b]furan-7-yl]-3,5-dihydroxyheptanoate,
ethyl 7-[5-benzoylamino-2,3-dihydro-2,2,4,6-tetramethylbenzo[b]furan-7-yl]-3,5-dihydroxyheptanoate,
ethyl 7-[5-benzoylamino-2,3-dihydro-2,2,4-trimethyl-6-(propan-2-yl)benzo[b]furan-7-yl]-3,5-dihydroxyheptanoate,
ethyl 7-[2,3-dihydro-2,2,4,6-tetramethyl-5-(N'-phenylcarbamoylamino)benzo[b]furan-7-yl]-3,5-dihydroxyheptanoate,
ethyl 7-[2,3-dihydro-2,2,4-trimethyl-5-(N'-phenylcarbamoylamino)-6-(propan-2-yl)benzo[b]furan-7-yl]-3,5-dihydroxyheptanoate,
ethyl 7-[2,3-dihydro-2,2,4,6-tetramethyl-5-(N'-phenylthiocarbamoylamino)benzo[b]furan-7-yl]-3,5-dihydroxyheptanoate,
ethyl 7-[2,3-dihydro-2,2,4-trimethyl-5-(N'-phenylthiocarbamoylamino)-6-(propan-2-yl)benzo[b]furan-7-yl]-3,5-dihydroxyheptanoate,
methyl 7-[2,3-dihydro-5-(isoindolin-2-yl)-2,2-dimethyl-6-(propan-2-yl)benzo[b]furan-7-yl]-3,5-dihydroxyheptanoate,
methyl 7-[2,3-dihydro-5-isoindolyl-2,2-dimethyl-6-(propan-2-yl)benzo[b]furan-7-yl]-3,5-dihydroxyheptanoate,
methyl 7-[6-(t-butyl)-2,3-dihydro-5-(isoindolin-2-yl)-2,2-dimethylbenzo[b]furan-7-yl]-3,5-dihydroxyheptanoate, and
methyl 7-[6-(t-butyl)-2,3-dihydro-5-isoindolyl-2,2-dimethylbenzo[b]furan-7-yl]-3,5-dihydroxyheptanoate.

Examples of the substituted amine derivatives represented by the previously mentioned general formula (VI-c) in this step are as follows:
trans-(±)-6-[2,3-dihydro-2,2,4,6-tetramethyl-5-methylaminobenzo[b]furan-7-yl]ethyl-4-hydroxytetrahydropyran-2-one,
trans-(±)-6-[2,3-dihydro-2,2,4-trimethyl-5-methylamino-6-(propan-2-yl)benzo[b]furan-7-yl]ethyl-4-hydroxytetrahydropyran-2-one,
trans-(±)-6-[2,3-dihydro-2,2,4,6-tetramethyl-5-dimethylaminobenzo[b]furan-7-yl]ethyl-4-hydroxytetrahydropyran-2-one,
trans-(±)-6-[2,3-dihydro-2,2,4-trimethyl-5-dimethylamino-6-(propan-2-yl)benzo[b]furan-7-yl]ethyl-4-hydroxytetrahydropyran-2-one,
trans-(±)-6-[2,3-dihydro-5-(isoindolin-2-yl)-2,2,4,6-tetramethylbenzo[b]furan-7-yl]ethyl-4-hydroxytetrahydropyran-2one,
trans-(±)-6-[2,3-dihydro-5-(isoindolin-2-yl)-2,2,4-trimethyl-6-(propan-2-yl)benzo[b]furan-7-yl]ethyl-4-hydroxytetrahydropyran-2-one,
trans-(±)-6-[2,3-dihydro-5-isoindolyl-2,2,4,6-tetramethylbenzo[b]furan-7-yl]ethyl-4-hydroxytetrahydropyran-2-one,
trans-(±)-6-[2,3-dihydro-5-isoindolyl-2,2,4-trimethyl-6-(propan-2-yl)benzo[b]furan-7-yl]ethyl-4-hydroxytetrahydropyran-2-one,
trans-(±)-6-[2,3-dihydro-2,2,4,6-tetra-methyl-5-(pyrolidin-1-yl)benzo[b]furan-7-yl]ethyl-4-hydroxytetrahydropyran-2one,
trans-(±)-6-[2,3-dihydro-2,2,4-trimethyl-5-(pyrrolidin-1-yl)-6-(propan-2-yl)benzo[b]furan-7-yl]ethyl-4-hydroxytetrahydropyran-2-one,
trans-(±)-6-[2,3-dihydro-2,2,4,6-tetramethyl-5-piperidinobenzo[b]furan-7-yl]ethyl-4-hydroxytetrahydropyran-2-one,
trans-(±)-6-[2,3-dihydro-2,2,4-trimethyl-5-piperidino-6-(propan-2-yl)benzo[b]furan-7-yl]ethyl-4-hydroxytetrahydropyran-2-one,
trans-(±)-6-[5-benzylamino-2,3-dihydro-2,2,4,6-tetramethylbenzo[b]furan-7-yl]ethyl-4-hydroxytetrahydropyran-2-one,
trans-(±)-6-[5-benzylamino-2,3-dihydro-2,2,4-trimethyl-6-(propan-2-yl)benzo[b]furan-7-yl]ethyl-4-hydroxytetrahydropyran-2-one,
trans-(±)-6-[5-(N-benzyl-N-methylamino)-2,3-dihydro-2,2,4,6-tetramethylbenzo[b]furan-7-yl]ethyl-4-hydroxytetrahydropyran-2-one,
trans-(±)-6-15-(N-benzyl-N-methylamino)-2,3-dihydro-2,2,4-trimethyl-6-(propan-2-yl)benzo[b]furan-7-yl]ethyl-4-hydroxytetrahydropyran-2-one,
trans-(±)-6-[5-dibenzylamino-2,3-dihydro-2,2,4,6-tetramethylbenzo[b]furan-7-yl]ethyl-4-hydroxytetrahydropyran-2-one,
trans-(±)-6-[5-dibenzylamino-2,3-dihydro-2,2,4-trimethyl-6-(propan-2-yl)benzo[b]furan-7-yl]ethyl-4-hydroxytetrahydropyran-2-one,
trans-(±)-6-[2,3-dihydro-5-(1,2,3,4-tetrahydroisoquinolin-2-yl)-2,2,4,6-tetramethylbenzo[b]furan-7-yl]ethyl-4-hydroxytetrahydropyran-2-one, trans-(±)-6-[2,3-dihydro-5-(1,2,3,4-tetrahydroisoquinolin-2-yl)-2,2,4-trimethyl-6-(propan-2-yl)benzo[b]furan-7-yl]ethyl-4-hydroxytetrahydropyran-2-one, trans-(±)-6-[5-acetoamino-2,3-dihydro-2,2,4,6-tetramethylbenzo[b]furan-7-yl]ethyl-4-hydroxytetrahydropyran-2-one, trans-(±)-6-[5-acetoamino-2,3-dihydro-2,2,4-trimethyl-6-(propan-2-yl)benzo[b]furan-7-yl]ethyl-4-hydroxytetrahydropyran-2-one, trans-(±)-6-[5-benzoylamino-2,3-dihydro-2,2,4,6-tetramethylbenzo[b]furan-7-yl]ethyl-4-hydroxytetrahydropyran-2-one, trans-(±)-6-[5-benzoylamino-2,3-dihydro-2,2,4-trimethyl-6-(propan-2-yl)benzo[b]furan-7-yl]ethyl-4-hydroxytetrahydropyran-2-one, trans-(±)-6-[2,3-dihydro-2,2,4,6-tetramethyl-5-(N'-phenylcarbamoylamino)benzo[b]furan-7-yl]ethyl-4-hydroxytetrahydro-pyran-2-one, trans-(±)-6-[2,3-dihydro-2,2,4-trimethyl-5-(N'-phenylcarbamoylamino)-6-(propan-2-yl)benzo[b]furan-7-yl]ethyl-4-hydroxytetrahydropyran-2-one, trans-(±)-6-[2,3-dihydro-2,2,4,6-tetramethyl-5-(N'-phenylthiocarbamoylamino)benzo[b]furan-7-yl]ethyl-4-hydroxytetrahydropyran-2-one, trans-(±)-6-[2,3-dihydro-2,2,4-trimethyl-5-(N'-phenylthiocarbamoylamino)-6-(propan-2-yl)benzo[b]furan-7-yl]ethyl-4-hydroxytetrahydropyran-2-one, trans-(±)-6-[2,3-dihydro-5-(isoindolin-2-yl)-2,2-dimethyl-6-(propan-2-yl)benzo[b]furan-7-yl]ethyl-4-hydroxytetrahydropyran-2-one, trans-(±)-6-[2,3-dihydro-5-isoindolyl-2,2-dimethyl-6-(propan-2-yl)benzo[b]furan-7-yl]ethyl-4-hydroxytetrahydropyran-2-one, trans-(±)-6-[6-(t-butyl)-2,3-dihydro-5-(isoindolin-2-yl)-2,2-dimethylbenzo[b]furan-7-yl]ethyl-4-hydroxytetrahydropyran-2-one, and trans-(±)-6-[6-(t-butyl)-2,3-dihydro-5-isoindolyl-2,2-dimethylbenzo[b]furan-7-yl]ethyl-4-hydroxytetrahydropyran-2-one.

The 3,5-dihydroxyheptanoic acid derivatives represented by the formula (II) wherein $R^6$ represents hydrogen, an alkali metal or an alkaline earth metal can be synthesized by a hydrolysis reaction of the compounds represented by the formulas (III-b), (IV-b), (V-b), (VI-b), (III-c), (IV-c), (V-c) and (VI-c) in an inert solvent. In addition, the 3,5-dihydroxyheptanoic acid derivatives represented by the formula (II) can be synthesized by use of the base employed in Step I-f under the same reaction conditions as in Step I-f.

4-hydroxytetrahydropyran-2-one and 3,5-dihydroxyheptanoic acid derivatives of the present invention which are represented by the previously mentioned general formulas (I) and (II) have an inhibition effect on the biosynthesis of cholesterol, which effect is based on the inhibition effect against the HMG-COA reductase, as show in Test Examples which will be described later. The 4-hydroxytetrahydropyran-2-one and 3,5-dihydroxyheptanoic acid derivatives represented by the previously mentioned general formulas (I) and (II) also have an antioxidation effect like vitamin E. Therefore, they serve as remedies for arteriosclerosis.

These derivatives can be administered not only by oral administration, but also by intravenous administration, subcutaneous administration, and intramuscular administration. Therefore, these compounds can be used in various administration forms, such as tablets, capsules, liquid, and suppository.

Obviously, numerous modifications and variations of the present invention are possible in light of the above teachings. It is therefore to be understood that within the scope of the appended claims, the invention may be practiced otherwise than as specifically described herein.

Other features of this invention will become apparent in the course of the following description of exemplary embodiments, which are given for illustration of the invention and are not intended to be limiting thereof.

REFERENCE EXAMPLE 1

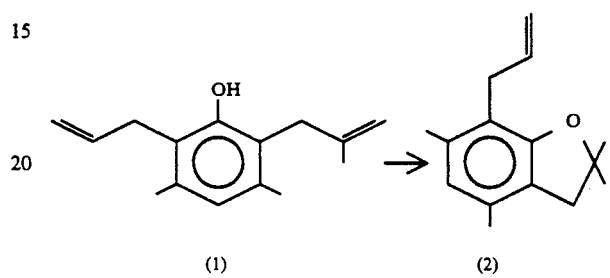

2.44 g (11.3 mmol) of 3,5-dimethyl-2-(2-methyl-2-propen-1-yl)-6-(2-propen-1-yl)phenol (Compound No. 1) was dissolved in 20 ml of 1,2-dichloroethane, and 0.42 ml (3.39 mmol) of boron trifluoride etherate was added thereto at 0° C. The above mixture was then stirred in an atmosphere of argon gas for 4 hours, poured into an aqueous solution of sodium hydrogencarbonate, and extracted with ethyl acetate. The thus obtained extract layer was washed successively with water and a saturated aqueous solution of sodium chloride, dried over magnesium sulfate, and then concentrated, whereby 2.37 g of a crude 2,3-dihydro-2,2,4,6-tetramethyl-7-(2-propen-1-yl)benzo[b]furan (Compound No. 2) was obtained as a yellow oily material.

$^1$HNMR (300 MHz, CDCl$_3$): δ 1.45 (s, 6H), 2.14 (s, 3H), 2.21 (s, 3H), 2.89 (s, 2H), 3.29 (d with fine coupling, J=6.1 Hz, 2H), 4.90–5.00 (m, 2H), 5.89 (ddt, J=17.8, 9.3 and 6.1 Hz, 1H), 6.47 (s, 1H) ppm IR (liquid film): 2976, 2924, 1640, 1594 cm$^{-1}$ Mass (m/z, %): 216 (M+, 100), 201 (54), 173 (20), 159 (27), 145 (10), 43 (7)

REFERENCE EXAMPLE 2

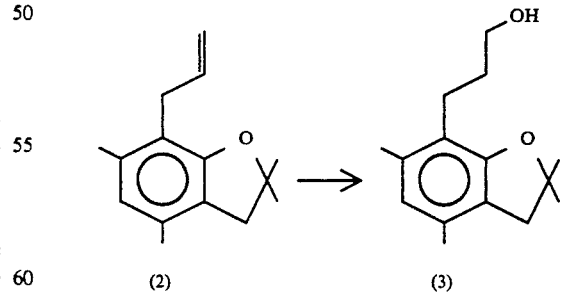

12.5 g (51.1 mmol) of 9-BBN dimer was suspended in 130 ml of anhydrous THF. In an atmosphere of argon gas, a solution of the Compound No. 2 synthesized in Reference Example 1 in 20 ml of anhydrous THF was added dropwise to the above obtained suspension at room temperature over a period of 20 minutes, followed by stirring for 3 hours and 25 minutes. After the addition of 10.4 ml of ethanol, 90 ml of an aqueous solution of 2N sodium hydroxide was further added to the above mixture at 0° C. Subsequently, 50 ml of a 30% aqueous hydrogen peroxide was gradually added to the above mixture.

The mixture was stirred at room temperature for 3 days, poured into 1N hydrochloric acid and extracted with ethyl acetate. The thus obtained extract layer was washed successively with water, a saturated aqueous solution of sodium thiosulfate and a saturated aqueous solution of sodium chloride, dried over magnesium sulfate, and concentrated. The thus concentrated material was chromatographed on a silica gel column and eluted with a mixed solvent of ethyl acetate and hexane at a ratio of 1:3, whereby 18.1 g of 3-[2,3-dihydro-2,2,4,6-tetramethylbenzo[b]furan-7-yl]propanol (Compound No. 3) was obtained as a colorless oily material in a yield of 90.4%.

$^1$HNMR (300 MHz, CDCl$_3$): δ 1.48 (s, 6H), 1.69-1.80 (m, 2H), 2.15 (s, 3H), 2.24 (s, 3H), 2.68(t, J=6.7 Hz, 2H), 2.85 (t, J=6.9 Hz, 1H), 2.93 (s, 2H), 3.45-3.55 (m, 2H), 6.52 (s, 1H) ppm IR (liquid film): 3428, 3024, 2972, 2936 cm$^{-1}$ Mass (m/z, %): 234 (M+, 61), 189 (100), 175 (13), 173 (14), 147 (12), 91 (9)

REFERENCE EXAMPLE 3

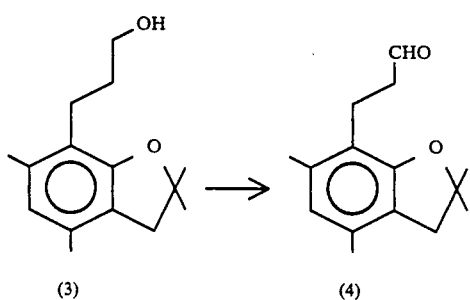

(3)    (4)

2.97 g (12.7 mmol) of the Compound No. 3 synthesized in Reference Example 2 was dissolved in a mixed solvent of 30 ml of dimethyl sulfoxide and 8 ml of anhydrous THF. and 8.85 ml (63.5 mmol) of triethylamine was added thereto. To the above mixture, 8.09 g (50.8 mmol) of sulfur trioxide pyridine complex was added, followed by stirring in an atmosphere of argon gas at room temperature for 1 hour and 30 minutes. After the addition of ice, the above obtained reaction mixture was stirred for a while, poured into 1N hydrochloric acid and extracted with hexane. The thus obtained extract layer was washed successively with water and a saturated aqueous solution of sodium chloride, dried over magnesium sulfate and then concentrated. The concentrated material was chromatographed on a silica gel column and eluted with a mixed solvent of ethyl acetate and hexane at a ratio of 1:6, whereby 2.24 g of 3-[2,3-dihydro-2,2,4,6-tetramethylbenzo[b]furan-7-yl]propanal (Compound No. 4) was obtained in a yield of 76.1%.

Melting Point (°C.): 36.0-36.5 (colorless particles, recrystallized from hexane)

$^1$HNMR (300 MHz, CDCl$_3$): δ 1.45 (s, 6H), 2.14 (s, 3H), 2.24 (s, 3H), 2.63 (td, J=6.9 and 1.8 Hz, 2H), 2.87 (t, J=6.9 Hz, 2H), 2.89 (s, 2H), 6.48 (s, 1H) 9.82 (t, J=1.8H, 1H) ppm IR (KBr): 2972, 2864, 2814, 2716, 1718 cm$^{-1}$ Mass (m/z, %): 232 (M+, 12), 189 (100), 176 (76), 173 (34), 161 (25), 147 (16), 91 (12)

REFERENCE EXAMPLE 4

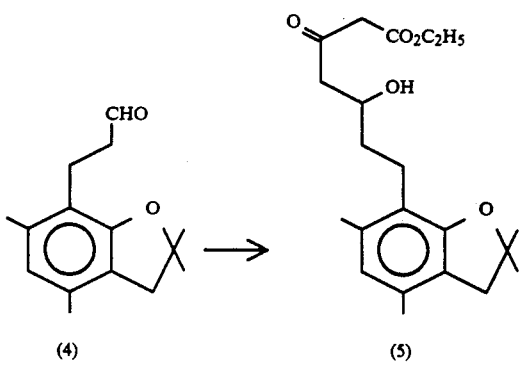

(4)    (5)

4.82 g (120.6 mmol) of a 60% sodium hydride was suspended in 150 ml of anhydrous THF in a stream of argon gas at 0° C., and 15.4 ml (120.6 mmol) of ethyl acetoacetate was added thereto, followed by stirring for 55 minutes.

Subsequently, 77.2 ml (120.6 mmol) of a 15% hexane solution of butyl lithium was added to the above mixture. The reaction mixture was stirred for 40 minutes, and cooled to −78° C. After the addition of a solution of 21.5 g (92.8 mmol) of the Compound No. 4 synthesized in Reference Example 3 in 40 ml of anhydrous THF, the above reaction mixture was further stirred for 2 hours and 10 minutes. After the addition of a saturated aqueous solution of ammonium chloride, the reaction mixture was extracted with ethyl acetate. The thus obtained extract layer was washed successively with 1N hydrochloric acid, water and a saturated aqueous solution of sodium chloride, dried over magnesium sulfate and concentrated. The thus obtained concentrated material was chromatographed on a silica gel column and eluted with a mixed solvent of ethyl acetate and hexane at a ratio of 1:4, and then with a mixed solvent of ethyl acetate and hexane at a ratio of 1:2, whereby 23.8 g of ethyl 7-[2,3-dihydro-2,2,4,6-tetramethylbenzo[b]furan-7-yl]-5-hydroxy-3-oxoheptanoate (Compound No. 5) was obtained as a colorless oily material in a yield of 70.9%.

$^1$HNMR (300 MHz, CDCl$_3$): δ 1.26 (t, J=7.2 Hz, 3H), 1.47 (s, 311), 1.48 (s, 3H), 1.55-1.74 (m, 2H), 2.14 (s, 3H), 2.23 (s, 3H), 2.56 (dd, J=16.1 and 3.3 Hz, 1H), 2.56-2.80 (m, 2H), 2.71 (dd, J=16.1 and 8.9 Hz, 1H), 2.91 (s, 2H), 3.49 (s, 2H), 3.59 (d, J=4.2 Hz, 1H), 3.85-3.97 (m, 1H), 4.17 (q, J=7.2 Hz, 2H), 6.50 (s, 1H) ppm IR (liquid film): 3526, 2974, 2928, 1746, 1716 cm$^{-1}$

EXAMPLE 1

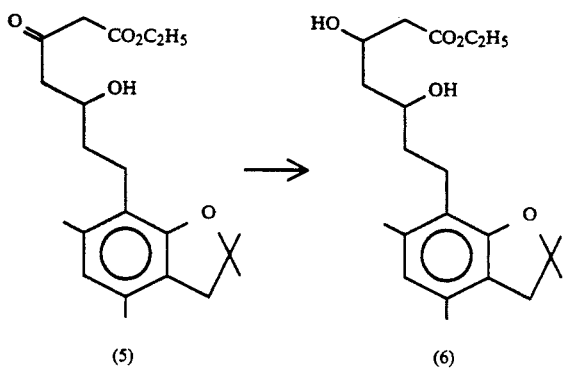

16.1 ml (16.1 mmol) of a 1.0M THF solution of triethyl borane was added to 63 mg (0.62 mmol) of pivalic acid, followed by stirring in an atmosphere of argon gas at room temperature for 1 hour. To the thus obtained mixture, a solution of 4.48 g (12.4 mmol) of the Compound No. 5 synthesized in Reference Example 4 in 15 ml of anhydrous THF. After the addition of 35 ml of anhydrous THF, the reaction mixture was further stirred for 1 hour and 30 minutes. The reaction mixture was cooled to −78° C., and 18.6 ml of methanol was added thereto. Subsequently, 562 mg (14.9 mmol) of sodium borohydride was added to the above reaction mixture in installments, followed by stirring for 1 hour and 45 minutes.

The above obtained reaction mixture was gradually poured into 150 ml of a 30% aqueous hydrogen peroxide cooled to 0° C., and stirred overnight at room temperature. Then, the reaction mixture was poured into a saturated aqueous solution of ammonium chloride and extracted with ethyl acetate. The thus obtained extract layer was washed successively with water, a saturated aqueous solution of sodium thiosulfate, water and a saturated aqueous solution of sodium chloride, dried over magnesium sulfate and concentrated. The thus obtained concentrated material was chromatographed on a silica gel column and eluted with a mixed solvent of ethyl acetate and hexane at a ratio of 1:2, whereby 4.24 g of ethyl 7-[2,3-dihydro-2,2,4,6-tetramethylbenzo[b]furan-7-yl]-3,5-dihydroxyheptanoate (Compound No. 6) was obtained as a light yellow oily material in a yield of 94.0%.

$^1$HNMR (300 MHz, CDCl$_3$): δ 1.24 (t, J=7.1 Hz, 3H), 1.48 (s, 3H), 1.50 (s, 3H), 1.40–1.76 (m, 4H), 2.15 (s, 3H), 2.23 (s, 3H), 2.37 (dd, J=15.4 and 5.7 Hz, 1H), 2.50 (dd, J=15.4 and 7.4 Hz, 1H), 2.59 (ddd, J=14.1, 4.8 and 4.8 Hz, 1H), 2.76 (ddd, J=14.1, 11.5 and 5.0 Hz, 1H), 2.94 (s, 2H), 3.61–3.73 (m, 1H), 4.13 (q, J=7,1 Hz, 2H), 4.15–4.28 (m, 1H), 4.25 (s with fine coupling, 1H), 4.43 (s, 1H), 6.53 (s, 1H) ppm IR (liquid film): 3480, 2976, 2936, 1740 cm$^{-1}$ Mass (m/z, %): 364 (M+, 42), 346 (16), 189 (100), 176 (17), 173 (16), 147 (12)

EXAMPLE 2

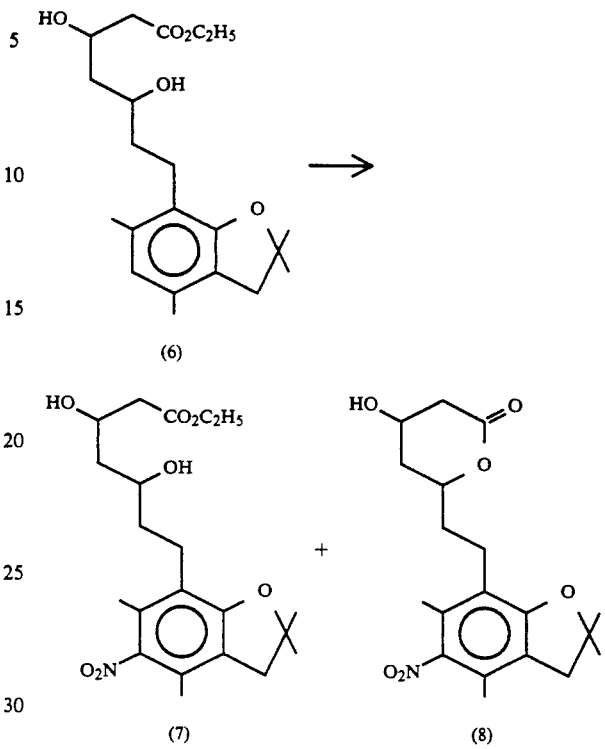

3.35 g (9.20 mmol) of the Compound No. 6 synthesized in Example 1 was dissolved in 20 ml of acetic acid. To this solution, 9.2 ml (18.4 mmol) of a 2M nitric acid in acetic acid was added dropwise on a water bath at 10° C. in a stream of argon gas, followed by stirring for 20 minutes. Furthermore, the thus obtained reaction mixture was stirred at room temperature for 5 minutes, poured into water and extracted with ethyl acetate. The thus obtained extract layer was washed successively with water, a saturated aqueous solution of sodium hydrogencarbonate and a saturated aqueous solution of sodium chloride, dried over magnesium sulfate and concentrated. The thus obtained concentrated material was chromatographed on a silica gel column and eluted with a mixed solvent of ethyl acetate and hexane at a ratio of 1:1, whereby 2.29 g of ethyl 7-[2,3-dihydro-2,2,4,6-tetramethyl-5-nitrobenzo[b]furan-7-yl]-3,5-dihydroxyheptanoate (Compound No. 7) was obtained in a yield Subsequently, 140 mg of trans-(±)-6-[2,3-dihydro-2,2,4,6-tetramethyl-5-nitrobenzo[b]furan-7-yl]ethyl-4-hydroxytetrahydropyran-2-one (Compound No. 8) was obtained (Compound No. 7)

Melting Point (°C.): 91.0–92.0 (yellow columns, recrystallized from ethyl acetate and hexane)

$^1$HNMR (300 MHz, CDCl$_3$): δ 1.26 (t, J=7.1 Hz, 3H), 1.50 (s, 3H), 1.51 (s, 3H), 1.50–1.75 (m, 4H), 2.14 (s, 3H), 2.19 (s, 3H), 2.41 (dd, J=15.9 and 5.0 HZ, 1H), 2.51 (dd, J=15.9 and 7.7 Hz, 1H), 2.60–2.82 (m, 2H), 2.98 (s, 2H), 3.65–3.77 (m, 1H), 3.83 (s with fine coupling, 1H), 4.10 (s with fine coupling, 1H), 4.15 (q, J=7.1 Hz, 2H), 4.18–4.30 (m, 1H) ppm IR (KBr): 3464, 2984, 2936, 1716 cm$^{-1}$ Mass (m/z, %): 409 (M+, 30), 392 (16), 379 (24), 356 (32), 318 (24), 234 (65), 189 (44), 69 (100)

(Compound No. 8)

Melting Point (°C.): 112.5-113.0 (yellow fine particles, recrystallized from ethyl acetate and hexane)

$^1$HNMR (300 MHz, CDCl$_3$): δ 1.47 (s, 3H), 1.48 (s, 3H), 1.70-1.90 (m, 4H), 1.92-2.04 (m, 1H), 2.13 (s, 3H), 2.20 (s, 3H), 2.63 (ddd, J=17.6, 3.9 and 1.5 Hz, 1H), 2.67-2.88 (m, 2H), 2.77 (dd, J=17.6 and 5.1 Hz, 1H), 2.93 (s, 2H), 4.38-4.44 (m, 1H) 4.65-4.75 (m, 1H) ppm IR (KBr): 3462, 2984, 2964, 2936, 1716 cm$^{-1}$ Mass (m/z, %): 363 (M+, 100), 346 (70), 234 (78), 216 (100), 187 (74), 129 (40), 91 (35)

EXAMPLE 3

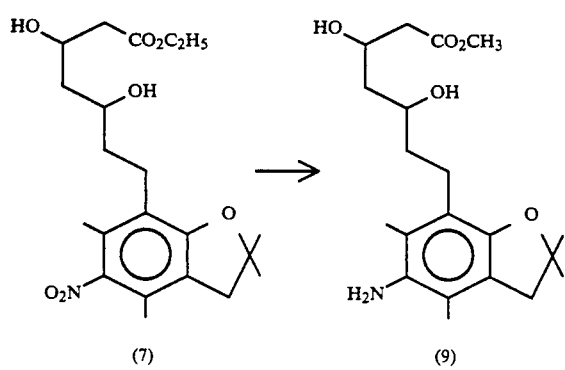

(7)         (9)

1.30 g (3.18 mmol) of the Compound No. 7 synthesized in Example 2 was dissolved in 20 ml of methanol. To this solution, 675 mg of platinum oxide was added. The thus obtained mixture was stirred in an atmosphere of hydrogen at room temperature for 2 hours and 30 minutes. After the addition of ethyl acetate, the reaction mixture was filtered through a Celite and concentrated. The thus obtained concentrated material was chromatographed on a silica gel column and eluted with a mixed solvent of ethyl acetate and methanol at a ratio of 10:1, whereby 982 mg of methyl 7-[5-amino-2,3-dihydro-2,2,4,6-tetramethylbenzo[b]furan-7-yl]-3,5-dihydroxyheptanoate (Compound No. 9) was obtained in a yield of 84.6%.

Melting Point (C°): 100.0-101.5 (yellow fine particles, recrystallized from ethyl acetate and hexane)

$^1$HNMR (300 MHz, CDCl$_3$): δ 1.46 (s, 3H), 1.48 (s, 3H), 1.50-1.75 (m, 4H), 2.06 (s, 3H), 2.08 (s, 3H), 2.37 (dd, J=15.4 and 6.0 Hz, 1H), 2.52 (dd, J=15.4 and 7.4 Hz, 1H), 2.57-2.68 (m, 1H), 2.76-2.90 (m, 1H), 2.97 (s, 2H), 3.30 (broad s, 2H), 3.59-3.70 (m, 1H), 3.67 (s, 3H), 4.12-4.24 (m, 1H), 4.45 (s with fine coupling, 1H), 4.56 (s, 1H) ppm IR (liquid film): 3410, 2970, 2932, 1738 cm$^{-1}$ Mass (m/z, %): 365 (M+, 100), 347 (6), 204 (22), 190 (5), 189 (15), 174 (6)

EXAMPLE 4

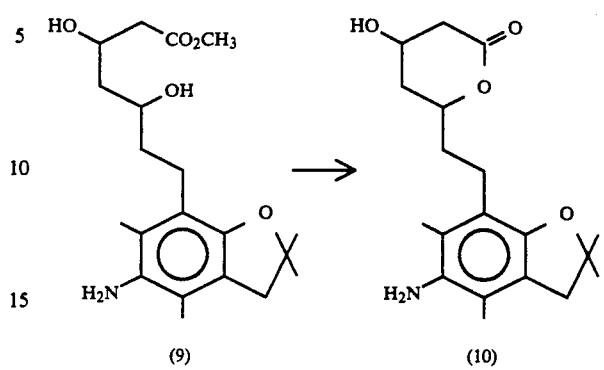

(9)         (10)

60 mg (0.16 mmol) of the Compound No. 9 synthesized in Example 3 was dissolved in 2 ml of acetone. To the thus obtained solution, 0.16 ml (0.16 mmol) of 1N sodium hydroxide was added. The thus obtained mixture was stirred overnight in an atmosphere of argon gas at room temperature. After the addition of 0.16 ml of 1N hydrochloric acid, the reaction mixture was concentrated. The thus obtained concentrated material was dissolved in 4 ml of anhydrous toluene and refluxed in an atmosphere of argon gas for 4 hours. The thus obtained reaction mixture was concentrated, chromatographed on a silica gel column and eluted with a mixed solvent of ethyl acetate and methanol at a ratio of 20:1, whereby 25 mg of trans-(±)-6-[5-amino-2,3-dihydro-2,2,4,6-tetramethylbenzo[b]furan-7-yl]ethyl-4-hydroxytetrahydropyran-2-one (Compound No. 10) was obtained in a yield of 45.8%.

Melting Point (C°): 140.0-142.0 (light yellow particles, recrystallized from ethyl acetate and hexane)

$^1$HNMR (300 MHz, CDCl$_3$): δ 1.42 (s, 3H), 1.43 (s, 3H), 1.70-1.98 (m, 4H), 1.98-2.10 (m, 1H), 2.05 (s, 3H), 2.11 (s, 3H), 2.61 (dd, J=17.9 and 4.0 Hz, 1H), 2.65-2.84 (m, 2H), 2.76 (dd, J=17.9 and 5.0 Hz, 1H), 2.91 (s, 2H), 3.26 (broad s, 1H), 4.35-4.44 (m, 1H), 4.65-4.76 (m, 1H) ppm IR (KBr): 3464, 2976, 2936, 2900, 1718 cm$^{-1}$ Mass (m/z, %): 333 (M+, 100), 315 (18), 247 (2), 204 (18), 188 (18), 144 (3)

EXAMPLE 5

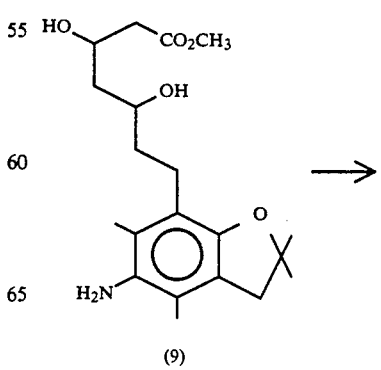

(9)

-continued

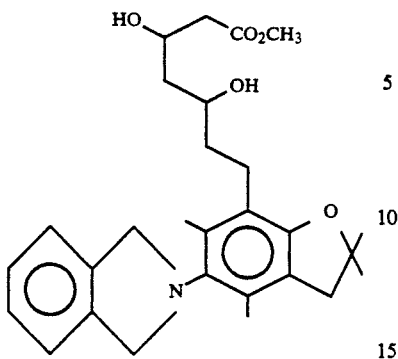

(11)

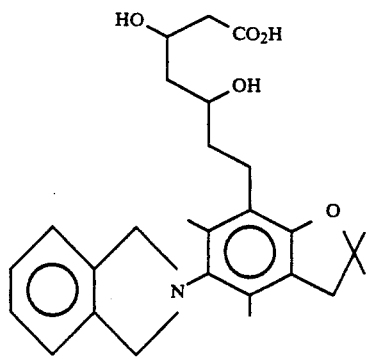

(12)

3.71 g (10.2 mmol) of the Compound No. 9 synthesized in Example 3 was dissolved in 100 ml of anhydrous DMF. To the thus obtained solution, 4.22 g (30.6 mmol) of potassium carbonate was added. After the addition of 4.04 g (15.3 mmol) of α,α'-dibromo-o-xylene, the reaction mixture was stirred in an atmosphere of argon gas at room temperature for 2 hours and 30 minutes. Then, the reaction mixture was poured into water, and extracted with ethyl acetate. The thus obtained extract layer was washed with a saturated aqueous solution of sodium chloride, dried over magnesium sulfate and concentrated. The thus obtained concentrated material was chromatographed on a silica gel column and eluted with a mixed solvent of ethyl acetate and hexane at a ratio of 2:1, whereby 2.67 g of methyl 7-[2,3-dihydro-5-(isoindolin-2-yl)-2,2,4,6-tetramethylbenzo[b]furan-7-yl]3,5-dihydroxyheptanoate (Compound No. 11) was obtained as a colorless oily material in a yield of 56.1%.

$^1$HNMR (300 MHz, CDCl$_3$): δ 1.50 (s, 3H), 1.52 (s, 3H), 1.50-1.75 (m, 2H), 2.08 (s, 3H), 2.17 (s, 3H), 2.40 (dd, J=15.5 and 5.8 Hz, 1H), 2.55 (dd, J=15.5 and 7.3 Hz, 1H), 2.58-2.67 (m, 1H), 2.72-2.86 (m, 1H), 2.96 (s, 2H), 3.68 (s, 3H), 3.62-3.78 (m, 1H), 4.17-4.29 (m, 1H), 4.30-4.36 (m, 1H), 4.50-4.58 (m, 1H), 4.55 (s, 4H), 7.28 (s, 4H) ppm IR (liquid film): 3476, 2972, 2932, 2852, 1740 cm$^{-1}$ Mass (m/z, %): 467 (M+, 100), 435 (10), 348 (13), 305 (23), 290 (12), 189 (6), 118 (8) 91 (7)

EXAMPLE 6

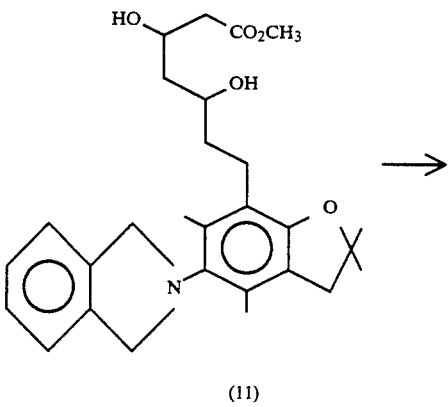

(11)

→

696 mg (1.49 mmol) of the Compound No. 11 synthesized in Example 5 was dissolved in 6 ml of methanol. To the thus obtained solution, 0.45 ml (2.24 mmol) of 5 N sodium hydroxide was added. The thus obtained mixture was stirred in an atmosphere of argon gas at room temperature for 1 hour. The thus obtained reaction mixture was poured into diluted hydrochloric acid and extracted with ethyl acetate. The thus obtained extract layer was washed successively with water and a saturated aqueous solution of sodium chloride, dried over magnesium sulfate and concentrated. The thus obtained concentrated material was crystallized from ethyl acetate and hexane, whereby 480 mg of 7-[2,3-dihydro-5-(isoindolin-2-yl)-2,2,4,6-tetramethylbenzo[b]furan-7-yl]3,5-dihydroxyheptoic acid (Compound No. 12) was obtained in a yield of 71.1%.

Melting Point (°C.): 130.0-131.5 (colorless fine particles, recrystallized from methanol and water)

$^1$HNMR (300 MHz, CDCl$_3$): δ 1.51 (s, 3H), 1.53 (s, 3H), 1.45-1.80 (m, 2H), 2.08 (s, 3H), 2.16 (s, 3H), 2.49 (dd, J=15.9 and 6.8 Hz, 1H), 2.56 (dd, J=15.9 and 4.7 Hz, 1H), 2.58-2.68 (m, 1H), 2.74-2.86 (m, 1H), 2.98 (s, 2H), 3.67-3.80 (m, 1H), 4.17-4.27 (M,1H), 4.52 (s, 4H), 7.28 (s, 4H) ppm IR (KBr): 3452, 2976, 2916, 2848, 1710 cm$^{-1}$ Mass (m/z, %): 453 (M+, 8), 435 (100), 417 (12), 305 (72), 288 (15), 118 (8), 91 (12)

EXAMPLE 7

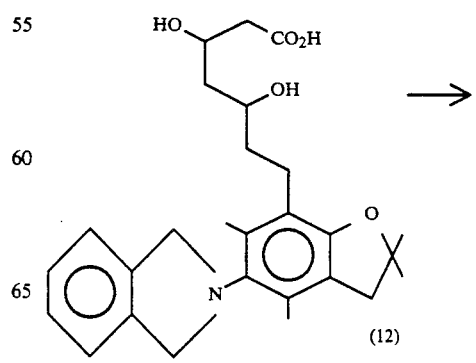

(12)

→

-continued

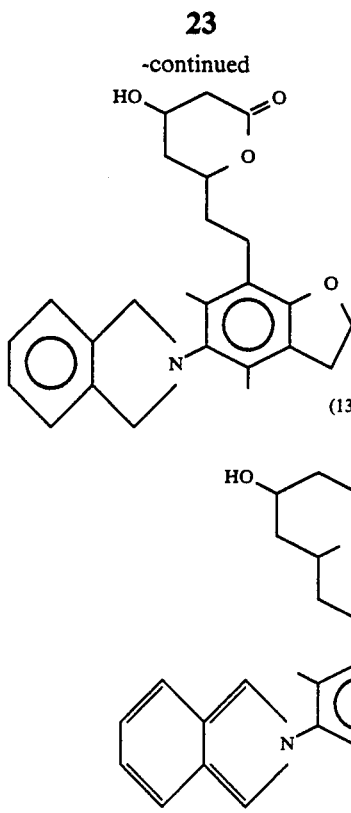

1.66 g of the crude compound no. 12 synthesized in Example 6 was dissolved in 20 ml of anhydrous toluene, and the thus obtained solution was refluxed in an atmosphere of argon gas for 4 hours and 40 minutes. The thus obtained reaction mixture was concentrated, chromatographed on a silica gel column and eluted with a mixed solvent of ethyl acetate and hexane at a ratio of 2:1, whereby 1.14 g of trans-(±)-6-[2,3-dihydro-5-(isoindolin-2-yl)-2,2,4,6-tetramethylbenzo[b]furan-7-yl]ethyl-4-hydroxytetrahydropyran-2-one (Compound No. 13) was obtained in a yield of 69.9%. Furthermore, 315 mg of trans-(±)-6-[2,3-dihydro-5-isoindolyl-2,2,4,6-tetramethylbenzo[b]furan-7-yl]ethyl-4-hydroxytetrahydropyran-2-one (Compound No. 14) was obtained in a yield of 19.3%.

(Compound No. 13)

Melting Point (°C.): 167.0–168.0 (colorless fine particles, recrystallized from ethyl acetate and hexane)

$^1$HNMR (300 MHz, CDCl$_3$): δ 1.46 (s, 3H), 1.47 (s, 3H), 1.72–2.00 (m, 4H), 2.00–2.10 (m, 1H), 2.07 (s, 3H), 2.19 (s, 3H), 2.62 (ddd, J=17.5, 4.2 and 1.5 Hz, 1H), 2.78 (dd, J=17.5 and 5.0 Hz, 1H), 2.67–2.84 (m, 2H), 2.91 (s, 2H), 4.37–4.46 (m, 1H), 4.55 (s, 4H), 4.68–4.80 (m, 1H), 7.27 (s, 4H) ppm IR (KBr): 3516, 2976, 2928, 2808, 1736 cm$^{-1}$ Mass (m/z, %): 435 (M$^+$, 22), 433 (15), 417 (59), 415 (100), 305 (64), 288 (24), 248 (8), 128 (8), 91 (10), 41 (14)

(Compound No. 14)

Melting Point (°C.): 193.0–194.0 (colorless particles, recrystallized from ethyl acetate and hexane)

$^1$HNMR (300 MHz, CDCl$_3$): δ 1.50 (s, 3H), 1.51 (s, 3H), 1.72 (s, 3H), 1.81 (s, 3H), 1.70–2.09 (m, 4H), 2.63 (ddd, J=17.5, 3.9 and 1.6 HZ, 1H), 2.65–2.90 (m, 2H), 2.78 (dd, J=17.5 and 5.0 Hz, 1H), 2.96 (s, 2H), 4.36–4.44 (m, 1H), 4.68–4.80 (m, 1H), 6.94–7.00 (m, 2H), 7.01 (s, 2H), 7.57–7.64 (m, 2H) ppm IR (KBr): 3476,, 2972, 2932, 1722 cm$^{-1}$ Mass (m/z, %): 433 (M$^+$, 26), 415 (100), 302 (31), 288 (18), 248 (5), 151 (4), 91 (3), 41 (4)

EXAMPLE 8

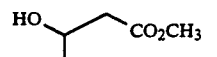

722 mg (1.55 mmol) of the Compound No. 11 synthesized in Example 5 was dissolved in 10 ml of acetone, followed by stirring in an atmosphere of argon gas at 0° C. To the thus obtained mixture, 1.55 ml (1.55 mmol) of 1N sodium hydroxide was added. The reaction mixture was then stirred for 1 hour and 30 minutes, and concentrated, whereby sodium 7-[2,3-dihydro-5-(isoindolin-2-yl)-2,2,4,6-tetramethylbenzo[b]furan-7-yl]-3,5-dihydroxyheptanoate (Compound No. 15) was obtained as a colorless amorphous solid in a yield of 100%.

$^1$HNMR (300 MHz, CD$_3$OD): δ 1.44 (s, 6H), 1.52–1.70 (m, 4H), 2.04 (s, 3H), 2.10–2.20 (m, 1H), 2.16 (s, 3H), 2.27 (dd, J=15.1 and 7.7 Hz, 1H), 2.37 (dd, J=15.1 and 4.9 Hz, 1H), 2.52–2.75 (m, 2H), 2.90 (s, 2H), 3.72–3.86 (m, 1H), 4.07–4.19 (m, 1H), 4.51 (s, 4H), 7.24 (s, 4H) ppm IR (KBr): 3432, 2972, 2932, 2852, 1580 cm$^{-1}$

EXAMPLE 9

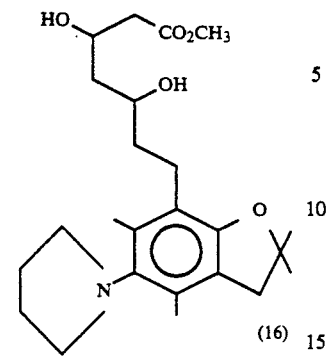

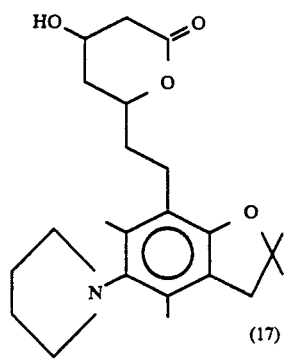

238 mg (0.652 mmol) of the Compound No. 9 synthesized in Example 3 was dissolved in 5 ml of DMF. To the thus obtained solution, 0.12 ml (0.980 mmol) of 1,4-dibromobutane was added in an atmosphere of argon gas, followed by stirring at room temperature for 2 hours. To the thus obtained reaction mixture, 0.47 ml (3.92 mmol) of 1,4-dibromobutane was added. The reaction mixture was then stirred for 2 days, poured into water and extracted with ethyl acetate. The thus obtained extract layer was diluted with hexane, washed successively with water and a saturated aqueous solution of sodium chloride, dried over magnesium sulfate, and concentrated. The thus obtained concentrated material was chromatographed on a silica gel column and eluted with a mixed solvent of ethyl acetate and hexane at a ratio of 2:1, whereby 243 mg of a crude methyl 7-[2,3-dihydro-2,2,4,6-tetramethyl-5-(pyrrolidin-1-yl)benzo[b]furan-7-yl]-3,5-dihydroxyheptanoate (Compound No. 16) was obtained as a yellow oily material.

$^1$HNMR (300 MHz, CDCl$_3$): δ 1.47 (s, 3H), 1.50 (s, 3H), 1.50–1.75 (m, 4H), 1.93–2.02 (m, 4H), 2.08 (s, 3H), 2.15 (s, 3H), 2.39 (dd, J=15.5 and 5.8 Hz, 1H), 2.48–2.66 (m, 2H), 2.70–2.84 (m, 1H), 2.94 (s, 2H), 3.10–3.20 (m, 4H), 3.67 (s, 3H), 3.67–3.77 (m, 1H), 4.15–4.27 (m, 1H), 4.35 (s with fine coupling, 1H), 4.54 (s, 1H) ppm IR (liquid film): 3488, 2956, 1742 cm$^{-1}$ Mass (m/z, %): 419 (M$^+$, 57), 369 (100), 301 (7), 257 (23), 214 (10), 200 (5), 173 (4), 129 (3)

EXAMPLE 10

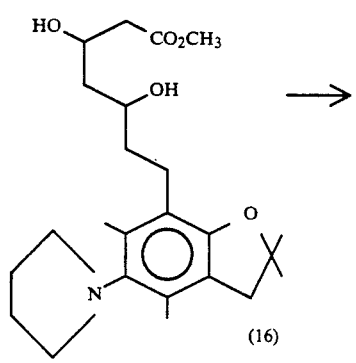

200 mg of the crude Compound No. 16 synthesized in Example 9 was dissolved in 5 ml of methanol. 0.2 ml (1.00 mmol) of 5N sodium hydroxide was then added to the above solution, followed by stirring overnight in an atmosphere of argon gas at room temperature. The thus obtained reaction mixture was poured into diluted hydrochloric acid so as to adjust to pH 7, and then extracted with ethyl acetate. The thus obtained extract layer was washed with a saturated aqueous solution of sodium chloride, dried over magnesium sulfate and concentrated. The thus obtained concentrated material was dissolved in 5 ml of anhydrous toluene and refluxed in an atmosphere of argon gas for 8 hours. The thus obtained reaction mixture was concentrated, chromatographed on a silica gel column, and eluted with ethyl acetate, whereby 102 mg of trans-(±)-6-[2,3-dihydro-2,2,4,6-tetramethyl-5-(pyrrolidin-1-yl)benzo[b]furan-7-yl]ethyl-4-hydroxytetrahydropyran-2-one (Compound No. 17) was Melting Point (°C.): 123.0–124.0 (colorless fine particles, recrystallized from diethyl ether)

$^1$HNMR (300 MHz, CDCl$_3$): δ 1.43 (s, 3H), 1.44 (s, 3H), 1.75–2.05 (m, 9H), 2.07 (s, 3H), 2.17 (s, 3H), 2.62 (ddd, J=17.4, 4.1 and 1.4 Hz, 1H), 2.60–2.80 (m, 2H), 2.77 (dd, J=17.4 and 5.1 Hz, 1H), 2.89 (s, 2H), 3.09–3.18 (m, 4H), 4.36–4.45 (m, 1H), 4.67–4.78 (m, 1H) ppm IR (KBr): 3452, 2968, 2872, 1700 cm$^{-1}$ Mass (m/z, %): 387 (M$^+$, 67), 369 (100), 301 (10), 257 (35), 214 (18), 187 (9), 144 (6), 129 (5)

EXAMPLE 11

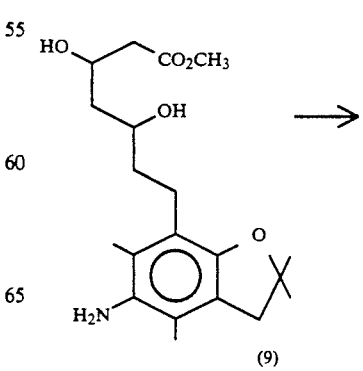

-continued

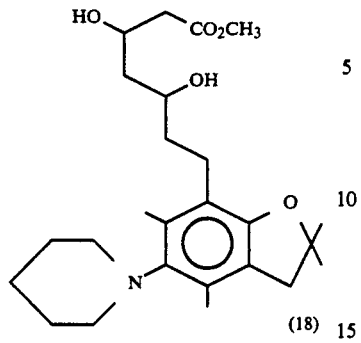

(18)

293 mg (0.80 mmol) of the Compound No. 9 synthesized in Example 3 was dissolved in 10 ml of DMF. To this solution, 333 mg (2.41 mmol) of potassium carbonate was added. 0.33 ml (2.41 mmol) of 1,5-dibromopentane was added, to the thus obtained mixture and stirred in an atmosphere of argon gas at room temperature for 4 days. The thus obtained reaction mixture was poured into water and extracted with a mixed solvent of hexane and ethyl acetate. The thus obtained extract layer was washed with a saturated aqueous solution of sodium chloride, dried over magnesium sulfate and concentrated. The thus obtained concentrated material was chromatographed on a silica gel column, and eluted with a mixed solvent of ethyl acetate and hexane at a ratio of 2:1, whereby 179 mg of a crude methyl 7-[2,3-dihydro-2,2,4,6-tetramethyl-5-piperidinobenzo[b]furan-7-yl]-3,5-dihydroxyheptanoate (Compound No. 18) was obtained as a yellow oily $^1$HNMR (300 MHz, CDCl$_3$): δ 1.46 (s, 3H), 1.48 (s, 3H), 1.40–1.70 (m, 10H), 2.15 (s, 3H), 2.21 (s, 3H), 2.38 (dd, J=15.4 and 5.8 Hz, 1H), 2.53 (dd, J=15.4 and 7.2 Hz, 1H), 2.55–2.64 (m, 1H), 2.70–2.81 (m, 1H), 2.93 (s, 2H), 2.93–3.06 (m, 4H), 3.60–3.73 (m, 1H), 3.67 (s, 3H), 4.18–4.24 (m, 1H), 4.36 (s with fine coupling 1H), 4.54 (s, 1H) ppm IR (liquid film): 3472, 2932, 1740 cm$^{-1}$ Mass (m/z, %): 433 (M$^+$, 100), 383 (11), 315 (4), 272 (7), 214 (3), 189 (3), 136 (3)

EXAMPLE 12

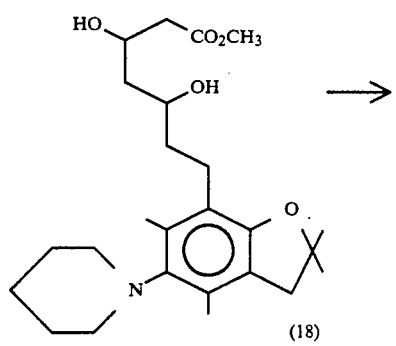

(18)

-continued

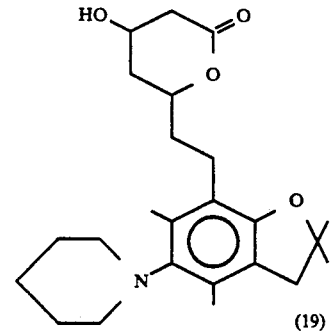

(19)

156 mg of the crude Compound No. 18 synthesized in Example 11 was dissolved in 3 ml of methanol. To this solution, 0.14 ml (0.72 mmol) of 5N sodium hydroxide was added. The thus obtained mixture was stirred in an atmosphere of argon gas at room temperature for 2 hours. The reaction mixture was poured into diluted hydrochloric acid so as to adjust to pH 4 and extracted with ethyl acetate. The thus obtained extract layer was washed with a saturated aqueous solution of sodium chloride, dried over magnesium sulfate and concentrated. To the thus obtained concentrated material, 5 ml of anhydrous toluene was added. The reaction mixture was then refluxed in an atmosphere of argon gas for 5 hours. The thus obtained reaction mixture was concentrated, chromatographed on a silica gel column, and eluted with a mixed solvent of ethyl acetate and hexane at a ratio of 4:1, whereby 108 mg of trans-(±)-6-[2,3-dihydro-2,2,4,6-tetramethyl-5-piperidinobenzo[b]furan-7-yl]ethyl-4-hydroxytetrahydropyran-2-one (Compound No. 19) was obtained.

Melting Point (°C.): 141.0–142.0 (colorless fine particles, recrystallized from diethyl ether)

$^1$HNMR (300 MHz, CDCl$_3$): δ 1.42 (s, 3H), 1.43 (s, 3H), 1.47–1.67 (m, 6H), 1.70–1.98 (m, 4H), 1.99–2.08 (m, 1H), 2.14 (s, 3H), 2.23 (s, 3H), 2.61 (ddd, J=17.4, 4.1 and 1.3 Hz, 1H), 2.59–2.77 (m, 2H), 2.77 (dd, J=17.4 and 5.1 Hz, 1H), 2.88 (s, 2H), 2.90–3.06 (m, 4H), 4.36–4.43 (m, 1H), 4.65–4.77 (m, 1H) ppm IR (KBr): 3484, 2932, 2848, 1712 cm$^{-1}$ Mass (m/z, %): 401 (M$^+$, 100), 383 (66), 271 (26), 214 (11), 200 (10), 173 (8), 159 (5), 43 (7), 41 (9)

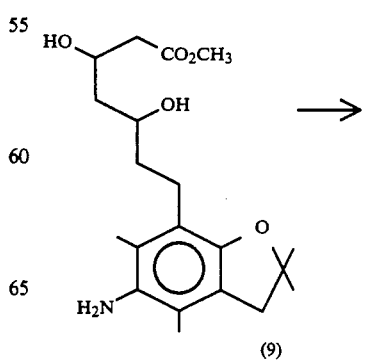

(9)

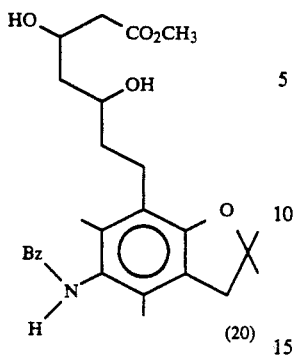

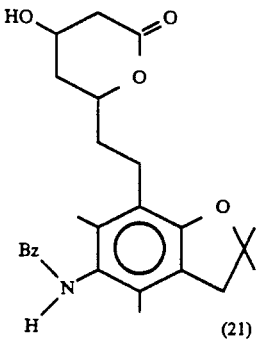

258 mg of the crude Compound No. 9 synthesized in Example 3 was dissolved in 2 ml of ethanol. To this solution, 0.11 ml (1.1 mmol) of benzaldehyde was added. The thus obtained mixture was stirred in an atmosphere of argon gas at room temperature for 1 hour and 30 minutes. This reaction mixture was concentrated and dissolved in 1 ml of methylene chloride. 16 mg (0.42 mmol) of sodium borohydride was added to 2 ml of methanol and 2 ml of methylene chloride, and the thus obtained mixture was stirred in an atmosphere of argon gas at $-78°$ C. To this mixture, the above obtained methylene chloride solution was added drop wise over a period of 5 minutes. After 2 hours and 15 minutes, the reaction mixture was poured into a saturated aqueous solution of ammonium chloride and extracted with ethyl acetate. The thus obtained extract layer was washed successively with water and a saturated aqueous solution of sodium chloride, dried over magnesium sulfate and concentrated. The thus obtained concentrated material was chromatographed on a silica gel column, and eluted with a mixed solvent of ethyl acetate and hexane at a ratio of 3:1, whereby 83 mg of a crude methyl 7-[5-benzylamino-2,3-dihydro-2,2,4,6-tetramethylbenzo[b]furan-7-yl]-3,5-dihydroxyheptanoate (Compound No. 20) was obtained.

$^1$HNMR (300 MHz, CDCl$_3$): δ 1.49 (s, 3H), 1.50 (s, 3H), 1.50–1.75 (m, 4H), 2.16 (s, 3H), 2.22 (s, 3H), 2.39 (dd, J=15.4 and 5.8 Hz, 1H), 2.53 (dd, J=15.4 and 7.3 Hz, 1H), 2.57–2.67 (m, 1H), 2.75–2.89 (m, 1H), 2.97 (s, 2H), 3.60–3.71 (m, 1H), 3.67 (s, 3H), 3.94 (s, 2H), 4.15–4.28 (m, 1H), 4.38 (s with fine coupling, 1H), 4.53 (s, 1H), 7.26 7.44 (m, 5H) ppm 82 mg of the crude Compound No. 20 synthesized in Example 13 was dissolved in 2 ml of methanol. To this solution, 0.27 ml (0.54 mmol) of 2N sodium hydroxide was added. The thus obtained mixture was stirred in an atmosphere of argon gas at room temperature for 3 hours and minutes. The reaction mixture was poured into a saturated aqueous solution of ammonium chloride and extracted with ethyl acetate. The thus obtained extract layer was washed successively with water and a saturated aqueous solution of sodium chloride, dried over magnesium sulfate and concentrated. The thus obtained concentrated material was dissolved in 3 ml of anhydrous toluene and refluxed in an atmosphere of argon gas for 5 hours. The thus obtained reaction mixture was further concentrated, chromatographed on a silica gel column, and eluted with a mixed solvent of ethyl acetate and hexane at a ratio of 4:1, whereby 70 mg of a crude trans-(±)-6-[5-benzylamino-2,3-dihydro-2,2,4,6-tetramethylbenzo[b]furan-7-yl]ethyl-4-hydroxytetrahydropyran-2-one (Compound No. 21) was obtained.

Furthermore, the thus obtained crude Compound No. 21 was chromatographed on a silica gel column, and eluted with a mixed solvent of ethyl acetate, hexane and acetic acid at a ratio of 40:20:1, whereby 30 mg of Compound No. 21 was obtained.

Melting Point (°C.): 99.5–101.0 (colorless particles, recrystallized from ethyl acetate and hexane)

$^1$HNMR (300 MHz, CDCl$_3$): δ 1.44 (s, 3H), 1.45 (s, 3H), 1.70–2.10 (m, 5H), 2.15 (s, 3H), 2.26 (s, 3H), 2.66 (dd with fine coupling, J=17.6 and 4.1 Hz, 1H), 2.67–2.84 (m, 2H), 2.77 (dd, J=17.6 and 5.0 Hz, 1H), 2.92 (s, 2H), 3.93 (s, 2H), 4.35–4.43 (m, 1H), 4.63–4.76 (m, 1H), 7.27–7.45 (m, 5H) ppm IR (KBr): 3524, 2972, 2932, 1732 cm$^{-1}$ Mass (m/z, %): 423 (M$^+$, 44), 405 (100), 333 (24), 314 (41), 202 (74), 189 (23), 174 (10), 91 (36), 41 (10)

EXAMPLE 14

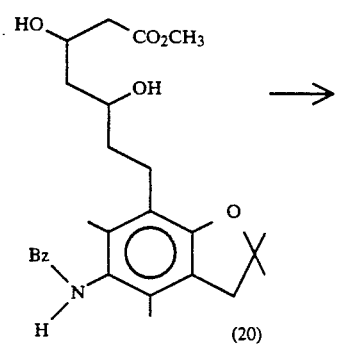

EXAMPLE 15

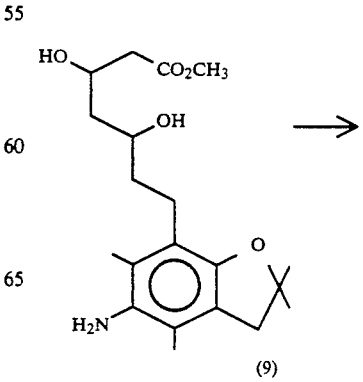

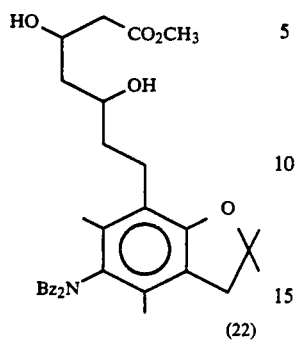

(22)

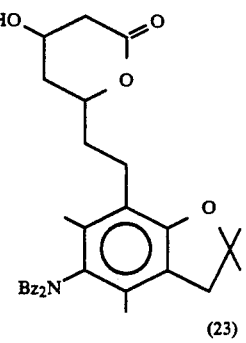

(23)

376 mg (1.03 mmol) of the Compound No. 9 synthesized in Example 3 was dissolved in 5 ml of DMF. To this solution, 0.18 ml (1.6 mmol) of benzyl bromide was added. Subsequently, 426 mg (3.09 mmol) of potassium carbonate was added to the above mixture, followed by stirring in an atmosphere of argon gas at room temperature for 1 hour and 10 minutes. The reaction mixture was poured into water and extracted with ethyl acetate. The thus obtained extract layer was washed with a saturated aqueous solution of sodium chloride, dried over magnesium sulfate and concentrated. The thus obtained concentrated material was chromatographed on a silica gel column and eluted with a mixed solvent of ethyl acetate and hexane at a ratio of 1:1, whereby 186 mg of a crude methyl 7-[5-dibenzylamino-2,3-dihydro-2,2,4,6-tetramethylbenzo[b]furan-7-yl]-3,5-dihydroxyheptanoate (Compound No. 22) was obtained.

1HNMR (300 MHz, CDCl$_3$): δ 1.48 (s, 3H), 1.50 (s, 3H), 1.40–1.70 (m, 4H), 2.01 (s, 6H), 2.37–2.45 (m, 1H), 2.50–2.60 (m, 2H), 2.70–2.83 (m, 1H), 2.92 (s, 2H), 3.53–3.65 (m, 1H), 3.68 (s, 3H), 4.08 (s, 4H), 4.18–4.30 (m, 1H), 4.32 (s with fine coupling, 1H), 4.55 (s, 1H), 7.11–7.30 (m, 10H) ppm

EXAMPLE 16

149 mg (0.273 mmol) of the Compound No. 22 synthesized in Example 15 was dissolved in 3 ml of methanol. To this solution, 0.16 ml (0.80 mmol) of 5N sodium hydroxide was added. The thus obtained mixture was stirred overnight in an atmosphere of argon gas at room temperature. The reaction mixture was poured into a saturated aqueous solution of ammonium chloride and extracted with ethyl acetate. The thus obtained extract layer was washed successively with water and a saturated aqueous solution of sodium chloride, dried over magnesium sulfate and concentrated. The thus obtained concentrated material was dissolved in 5 ml of anhydrous toluene and refluxed for 13 hours. The thus obtained reaction mixture was further concentrated, chromatographed on a silica gel column, and eluted with a mixed solvent of ethyl acetate and hexane at a ratio of 2:1, and then with an ethyl acetate, whereby 93 mg of trams-(±)-6-[5-dibenzylamino-2,3-dihydro-2,2,4,6-tetramethylbenzo[b]furan-7-yl]ethyl-4-hydroxytetrahydropyran-2-one (Compound No. 23) was obtained as a light yellow amorphous solid in a 1HNMR (300 MHz, CDCl$_3$): δ 1.44 (s, 3H), 1.45 (s, 3H), 1.70–1.92 (m, 4H), 1.98–2.08 (m, 1H), 1.98 (s, 3H), 2.07 (s, 3H), 2.56–2.77 (m, 3H), 2.77 (dd, J=17.5 and 5.0 Hz, 1H), 2.86 (s, 2H), 4.07 (s, 2H), 4.08 (s, 2H), 4.35–4.43 (m, 1H), 4.60–4.71 (m, 1H), 7.15–7.30 (m, 12H) ppm IR (KBr): 3464, 2968, 2928, 1712 cm$^{-1}$ Mass (m/z, %): 513 (M+, 56), 495 (76), 422 (55), 404 (100), 292 (62), 277 (19), 202 (11), 188 (10), 91 (98)

EXAMPLE 17

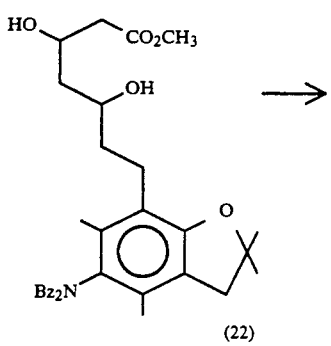

(22)

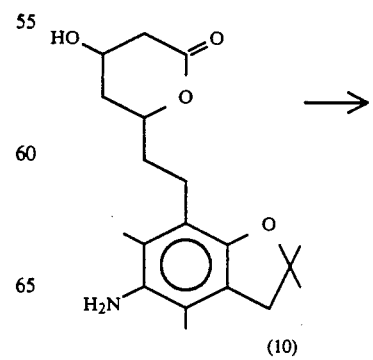

(10)

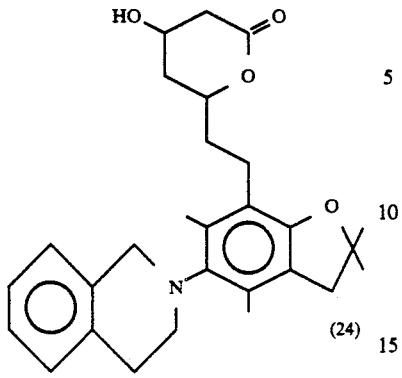

(24)

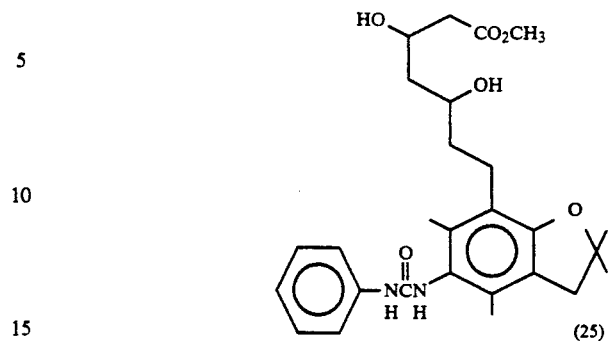

(25)

48 mg (0.14 mmol) of the Compound No. 10 synthesized in Example 4 was dissolved in 5 ml of DMF. To this solution, 60 mg (0.43 mmol) of potassium carbonate was added. 60 mg (0.22 mmol) of 1-(2-bromoethyl)-2-(bromomethyl)benzene was added to the thus obtained mixture in an atmosphere of argon gas at room temperature and stirred for 4 days. The reaction mixture was then poured into water and extracted with ethyl acetate. The thus obtained extract layer was washed with a saturated aqueous solution of sodium chloride, dried over magnesium sulfate and concentrated. The thus obtained concentrated material was chromatographed on a silica gel column, and eluted with a mixed solvent of ethyl acetate and hexane at a ratio of 2:1, whereby 23 mg of trans-($\pm$)-6-[2,3-dihydro-5-(1,2,3,4-tetrahydroisoquinolin-2-yl)-2,2,4,6-tetramethylbenzo[b]furan-7-yl]ethyl-4-hydroxytetrahydropyran-2-one (Compound No. 24) was obtained in a Melting Point (°C.): 138.0–139.0 (colorless fine particles, recrystallized from diethyl ether and hexane)

$^1$HNMR (300 MHz, CDCl$_3$): $\delta$ 1.45 (s, 3H), 1.45 (s, 3H), 1.72–2.00 (m, 4H), 2.00–2.08 (m, 1H), 2.13 (s, 3H), 2.22 (s, 3H), 2.62 (ddd, J=17.4, 4.3 and 1.6 Hz, 1H), 2.62–2.85 (m, 2H), 2.77 (dd, J=17.4 and 5.0 Hz, 1H), 2.90 (s, 2H), 2.85–3.03 (m, 2H), 3.28–3.40 (m, 2H), 4.17 (d, J=16.3 Hz, 1H), 4.25 (d, J=16.3 Hz, 1H), 4.37–4.43 (m, 1H), 4.68–4.80 (m, 1H), 7.00–7.07 (m, 1H), 7.10–7.21 (m, 3H) ppm IR (KBr): 3556, 2968, 2932, 1728 cm$^{-1}$ Mass (m/z, %): 449 (M$^+$, 13), 431 (66), 362 (9), 319 (100), 214 (10), 200 (10), 173 (7), 130 (7), 129 (7), 117 (10), 105 (16)

EXAMPLE 18

61 mg (0.17 mmol) of the Compound No. 9 synthesized in Example 3 was dissolved in 2 ml of ethanol. To this solution, 0.02 ml (0.17 mmol) of phenyl isocyanate was added, followed by stirring in an atmosphere of argon gas at room temperature for 30 minutes. The reaction mixture was concentrated, chromatographed on a silica gel column, and eluted with a mixed solvent of ethyl acetate and methanol at a ratio of 20:1, whereby 81 mg of methyl 7-[2,3-dihydro-2,2,4,6-tetramethyl-5-(N′-phenylcarbamoylamino)benzo[b]furan-7-yl]-3,5-dihydroxyheptanoate (Compound No. 25) was obtained in a yield of 100%.

Melting Point (°C.): 142.0–143.0 (colorless particles, recrystallized from ethyl acetate and hexane)

$^1$HNMR (300 MHz, CDCl$_3$): $\delta$ 1.53 (s, 6H), 2.18 (s, 3H), 2.24 (s, 3H), 2.41 (dd, J=15.8 and 5.4 Hz, 1H), 2.53 (dd, J=15.8 and 7.6 Hz, 1H), 2.60–2.71 (m, 1H), 2,71–2.88 (m, 1H), 3.00 (s, 2H), 3.60–3.78 (m, 1H), 3.68 (s, 3H), 3.95–4.15 (m, 1H), 4.18–4.35 (m, 2H), 5.70 (broad s, 1H), 6.10–6.18 (m, 1H), 7.00–7.10 (m, 1H), 7.26–7.48 (m, 4H) ppm IR (KBr): 3344, 2976, 2944, 1740, 1652, 1600 cm$^{-1}$ Mass (m/z, %): 484 (M$^+$, 10), 434 (19), 359 (48), 333 (47), 230 (100), 188 (46), 93 (50)

EXAMPLE 19

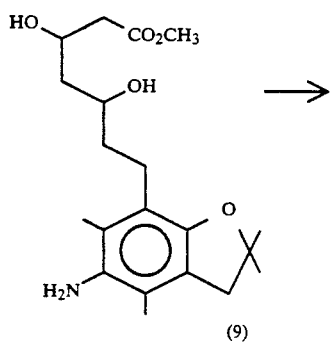

(9)

→

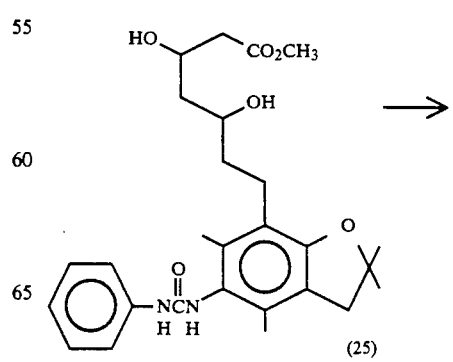

(25)

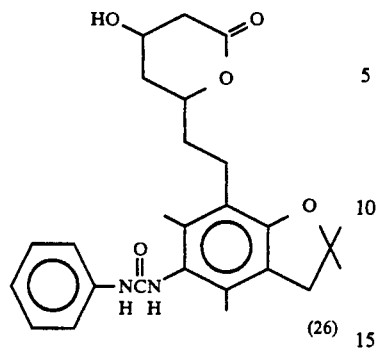

150 mg (0.31 mmol) of the Compound No. 25 synthesized in Example 18 was dissolved in 3 ml of methanol. 0.12 ml (0.60 mmol) of 5N sodium hydroxide was added to the above obtained solution, followed by stirring in an atmosphere of argon gas at room temperature for 1 hour. The reaction mixture was poured into diluted hydrochloric acid so as to adjust to pH 4, and extracted with ethyl acetate. The thus obtained extract layer was washed successively with water and a saturated aqueous solution of sodium chloride, dried over magnesium sulfate and concentrated. The thus obtained concentrated material was dissolved in 5 ml of anhydrous toluene, and refluxed for 1 hour and 50 minutes. The thus obtained reaction mixture was further concentrated and crystallized from ethyl acetate, whereby 75 mg of trans-(±)-6-[2,3-dihydro-2,2,4,6-tetramethyl-5-(N'-phenyl-carbamoylamino)benzo[b]furan-7-yl]ethyl-4-hydroxytetrahydropyran-2-one (Compound No. 26) was obtained in a yield of 53.5%.

Melting Point (°C.): 214.0–215.0 (colorless fine particles, recrystallized from methanol)

$^1$HNMR (300 MHz, CDCl$_3$): δ 1.48 (s, 6H), 1.72–2.10 (m, 5H), 2.16 (s, 3H), 2.25 (s, 3H), 2.56–2.66 (m, 1H), 2.67–2.85 (m, 2H), 2.76 (dd, J=17.5 and 5.0 Hz, 1H), 2.95 (s, 2H), 4.36–4.45 (m, 1H), 4.66–4.77 (m, 1H), 5.69–5.76 (m, 1H), 6.14–6.26 (m, 1H), 7.00–7.09 (m, 1H), 7.26–7.39 (m, 4H) ppm IR (KBr): 3308, 2976, 2932, 1694, 1646, 1602 cm$^{-1}$ Mass (m/z, %): 452 (M+, 8), 434 (92), 359 (55), 341 (73), 333 (47), 315 (100), 230 (61), 204 (38), 188 (21), 119 (20), 93 (46)

REFERENCE EXAMPLE 5

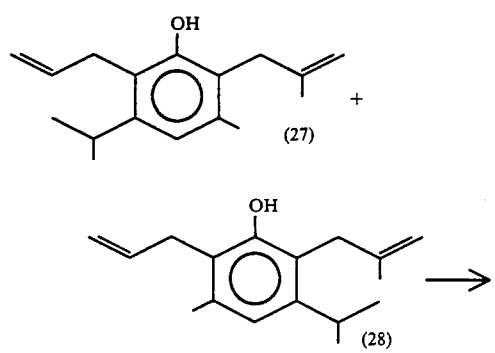

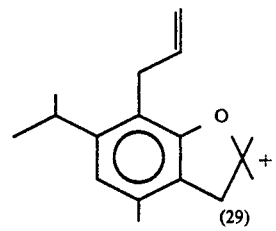

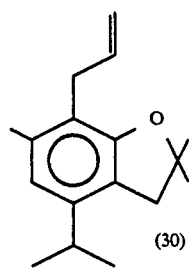

50.0 g (0.205 mmol) of a mixture of 3-methyl-2-(2-methyl-2-propen-1-yl)-5-(propan-2-yl)-6-(2-propen-1-yl)phenol (Compound No. 27) and 3-methyl-6-(2-methyl-2-propen-1-yl)-5-(propan-2-yl)-2-(2-propen-1-yl)phenol (Compound No. 28) at a ratio of 2:1, and 696 mg (3.66 mmol) of p-toluenesulfonic acid monohydrate were added to 150 ml of methylene chloride. The above reaction mixture was refluxed in an atmosphere of argon gas, poured into an aqueous solution of sodium hydrogencarbonate, and extracted with hexane. The thus obtained extract layer was washed with a saturated aqueous solution of sodium chloride, dried over magnesium sulfate and concentrated. The thus obtained concentrated material was chromatographed on a silica gel column, and eluted with a mixed solvent of hexane and ethyl acetate at a ratio of 20:1, whereby 39.7 g of a mixture of 2,3-dihydro-2,2,4-trimethyl-6-(propan-2-yl)-7-(2-propen-1-yl)benzo[b]furan (Compound No. 29) and 2,3-dihydro-2,2,6-trimethyl-4-(propan-2-yl)-7-(2-propen-1-yl)benzo[b]furan (Compound No. 30) at a ratio of 2:1 was obtained as a colorless oily material in a yield of 79.3%.

(A mixture of the Compound No. 29 and the Compound No. 30 at a ratio of 2:1)

$^1$HNMR (300 MHz, CDCl$_3$): δ 1.18 (d, J=6.8 Hz, 4H), 1.20 (d, J=6.8 Hz, 2H), 1.44 (s, 6H), 2.18 (s, 2H), 2.24 (s, 1H), 2.78 (hept, J=6.8 Hz, 0.33H), 2.89 (s, 1.33H), 2.24 (s, 0.67H), 3.08 (hept, J=6.8 Hz, 0.67H), 3.30 (broad d, J=6.2 Hz, 0.67H), 3.34 (broad d, J=5.9 Hz, 1.33H), 4.86–5.02 (m, 2H), 5.82–6.04 (m, 1H), 6.52 (s, 0.33H), 6.57 (s, 0.67H) ppm

REFERENCE EXAMPLE 6

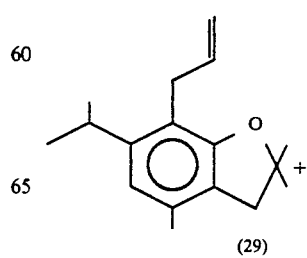

-continued

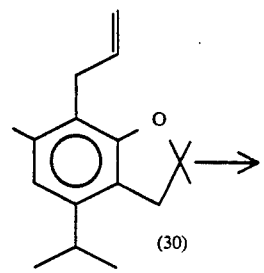
(30)

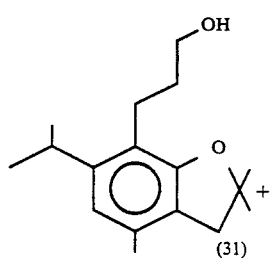
(31)

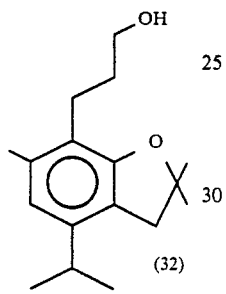
(32)

15.1 g (0.124 mol) of 9-BBN dimer was added to 100 ml of anhydrous THF, and stirred in an atmosphere of argon gas at 0° C. To this mixture, a solution of 20.0 g (82.0 mmol) of a 2:1 mixture of the Compounds No. 29 and No. 30 synthesized in Reference Example 5 in 20.0 ml of anhydrous THF was added, followed by stirring for 1 hour and 10 minutes. To this reaction mixture, 9.9 ml of ethanol was further added, followed by stirring for 30 minutes. Furthermore, 82.0 ml of 2N sodium hydroxide and then 45.0 ml of a 30% aqueous hydrogen peroxide were gradually added to the above reaction mixture. The reaction mixture was then stirred for 2 hours, poured into 1N hydrochloric acid, and extracted with ethyl acetate. The thus obtained extract layer was washed successively with an aqueous solution of sodium thiosulfate twice and an aqueous solution of sodium chloride, dried over magnesium sulfate and concentrated. The concentrated material was chromatographed on a silica gel column, and eluted with a mixed solvent of hexane and ethyl acetate at a ratio of 4:1, whereby 14.4 g of a mixture of 3-[2,3-dihydro-2,2,4-trimethyl-6-(propan-2-yl)benzo[b]furan-7-yl]propanol (Compound No. 31) and 3-[2,3-dihydro-4-(propan-2-yl)-2,2,6-trimethylbenzo[b]furan-7-yl]propanol (Compound No. 32) at a ratio of 4:1 was obtained in a yield of 67.1%.

Subsequently, 4.30 g of a mixture of the Compound No. and the Compound No. 32 at a ratio of 1:1 was obtained in a yield 20.0%, and the Compound No. 31 was isolated and purified by recrystallizing the mixture from hexane.

(A mixture of the Compound No. 31 and the Compound No. 32 at a ratio of 4:1)

¹HNMR (300 MHz, CDCl₃): δ 1.20 (d, J=6.8 Hz, 6H), 1.48 (s, 6H), 1.68-1.82 (m, 2H), 2.18 (s, 2.4H), 2.26 (s, 0.6H), 2.64-2.76 (m, 2H), 2.78 (hept, J=6.8 Hz, 0.2H), 2.82-2.90 (m, 1H), 2.93 (s, 1.6H), 2.98 (s, 0.4H), 3.09 (hept, J=6.8 Hz, 0.8H), 3.46-3.56 (m, 2H), 6.57 (s, 0.2H), 6.61 (s, 0.8H) ppm (Compound No. 31)

Melting Point (0C): 78.0-79.0 (colorless needles, recrystallized from hexane and ethyl acetate)

¹HNMR (300 MHz, CDCl₃): δ 1.20 (d, J=6.9 Hz, 6H), 1.48 (s, 6H), 1.68-1.80 (m, 2H), 2.18 (s, 3H), 2.72 (t, J=6.7 Hz, 2H), 2.86 (t, J=6.9 Hz, 1H), 2.93 (s, 2H), 3.10 (hept, J=6.9 Hz, 1H), 3.46-3.56 (m, 2H), 6.61 (s, 1H) ppm IR (KBr): 3472, 3424, 2972, 1590 cm⁻¹

Mass (m/z, %): 262 (M⁺, 100), 217 (91), 203 (29)

REFERENCE EXAMPLE 7

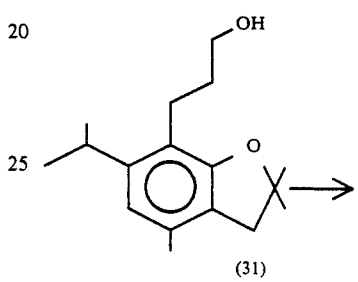
(31)

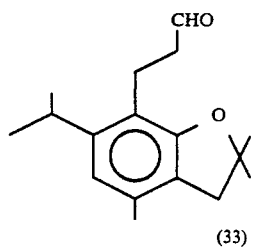
(33)

3.02 g (11.5 mmol) of the Compound No. 31 synthesized in Reference Example 6 was added to 35.0 ml of dimethyl sulfoxide, followed by stirring in an atmosphere of argon gas at room temperature. To the thus obtained mixture, 5.60 ml (40.2 mmol) of triethylamine, 10.0 ml of anhydrous THF and 5.50 g (34.6 mmol) of sulfur trioxide pyridine complex were successively added. The reaction mixture was then stirred for 1 hour, poured into diluted hydrochloric acid, and extracted with hexane. The thus obtained extract layer was washed with a saturated aqueous solution of sodium chloride three times, dried over magnesium sulfate and concentrated. The concentrated material was chromatographed on a silica gel column, and eluted with a mixed solvent of hexane and ethyl acetate at a ratio of 10:1, whereby 2.40 g of 3-[2,3-dihydro-2,2,4-trimethyl-6-(propan-2-yl)benzo[b]furan-7-yl]propanal (Compound No. 33) was obtained in a yield of 80.1%.

Melting Point (°C.): 53.0-53.5 (colorless columns, recrystallized from hexane)

¹HNMR (300 MHz, CDCl₃): δ 1.21 (d, J=6.8 Hz, 6H), 1.45 (s, 6H), 2.17 (s, 3H), 2.63 (td, J=8.0 and 1.7 Hz, 2H), 2.89 (s, 2H), 2.90 (t, J=8.0 Hz, 2H), 3.05 (hept, J=6.8 Hz, 1H), 6.57 (s, 1H), 9.83 (t, J=1.7 Hz, 1H) ppm IR (KBr): 2968, 1722, 1626, 1592 cm⁻¹

Mass (m/z, %): 260 (M⁺, 73), 217 (84), 204 (100)

REFERENCE EXAMPLE 8

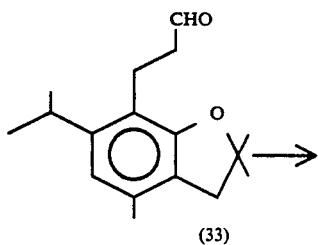

(33)

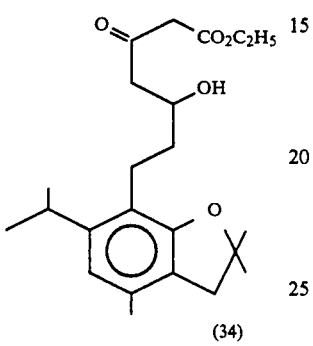

(34)

3.60 ml (28.2 mmol) of ethyl acetoacetate was added to a suspension of 1.12 g (28.0 mmol) of a 60% sodium hydride in 25.0 ml of anhydrous THF in a stream of argon gas at 0° C., followed by stirring for 15 minutes. To this mixture, 17.3 ml (27.0 mmol) of a 15% hexane solution of butyl lithium was further added. The reaction mixture was then stirred for 20 minutes, cooled to −78° C. To the thus obtained reaction mixture, a solution of 4.80 g (18.5 mmol) of the Compound No. 33 synthesized in Reference Example 7 in 20.0 ml of anhydrous THF was added over a 30-minutes period. Then, the reaction mixture was further stirred for 2 hours, poured into a saturated aqueous solution of sodium chloride, and extracted with ethyl acetate. The thus obtained extract layer was washed with a saturated aqueous solution of sodium chloride three times, dried over magnesium sulfate and concentrated. The concentrated material was chromatographed on a silica gel column, and eluted with a mixed solvent of hexane and ethyl acetate at a ratio of 3:1, whereby 5.74 g of ethyl 7-[2,3-dihydro-2,2,4-trimethyl-6-(propan-2-yl)benzo[b]furan-7-yl]-5-hydroxy-3-oxoheptanoate (Compound No. 34) was obtained as a colorless oily material in a yield of 80.0%.

$^1$HNMR (300 MHz, CDCl$_3$): δ 1.19 (d, J=6.7 Hz, 3H), 1.21 (d, J=6.7 Hz, 3H), 1.26 (t, J=7.2 Hz, 3H), 1.47 (s, 3H), 1.48 (s, 3H), 1.50–1.76 (m, 2H), 2.17 (s, 3H), 2.57 (dd, J=16.2 and 3.3 Hz, 1H), 2.62–2.81 (m, 3H), 2.92 (s, 2H), 3.07 (hept, J=6.7 Hz, 1H), 3.49 (s, 2H), 3.61 (d, J=3.3 Hz, 1H), 3.87–4.00 (m, 1H), 4.17 (q, J=7.2 Hz, 2H), 6.60 (s, 1H) ppm IR (liquid film): 3524, 2968, 2932, 1746, 1716, 1628, 1594 cm$^{-1}$ Mass (m/z, %): 390 (M$^+$, 100), 217 (86)

EXAMPLE 20

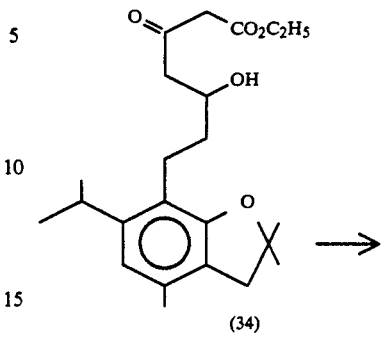

(34)

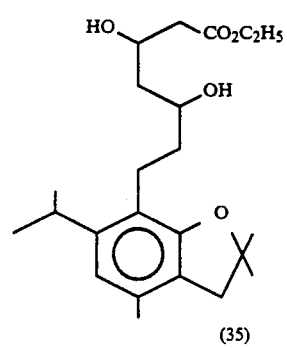

(35)

80 mg (0.78 mmol) of pivalic acid was added to 20.7 ml (20.7 mmol) of a 1.0M THF solution of triethylborane in an atmosphere of argon gas at room temperature, followed by stirring for 1 hour and 30 minutes. To the thus obtained mixture, a solution of 6.20 g (15.9 mmol) of the Compound No. 34 synthesized in Reference Example 8 in 50 ml of anhydrous THF was added. The reaction mixture was then stirred for 1 hour, and cooled to −78° C. 16.0 ml of methanol and 660 mg (17.6 mmol) of sodium borohydride were successively added to the above mixture by three installments, followed by stirring for 1 hour and 30 minutes. Then, the reaction mixture was gradually added to 90.0 g of a 30% aqueous hydrogen peroxide at 0° C., and stirred overnight.

The above reaction mixture was poured into diluted hydrochloric acid and extracted with ethyl acetate. The thus obtained extract layer was washed successively with a saturated aqueous solution of sodium chloride, an aqueous solution of sodium thiosulfate and a saturated aqueous solution of sodium chloride twice, dried over magnesium sulfate and concentrated. The thus obtained concentrated material was chromatographed on a silica gel column, and eluted with a mixed solvent of hexane and ethyl acetate at a ratio of 3:1, whereby 5.43 g of ethyl 7-[2,3-dihydro-2,2,4-trimethyl-6-(propan-2-yl)benzo[b]furan-7-yl]-3,5-dihydroxyheptanoate (Compound No. 35) was obtained as a colorless oily material in a yield of 87.2%.

$^1$HNMR (300 MHz, CDCl$_3$): δ 1.18 (d, J=6.8 Hz, 3H), 1.21 (d, J=6.8 Hz, 3H), 1.24 (t, J=7.1 Hz, 3H), 1.49 (s, 3H), 1.50 (s, 3H), 1.46–1.78 (m, 4H), 2.19 (s, 3H), 2.37 (dd, J=15.5 and 5.5 Hz, 1H), 2.50 (dd, 15.5 and 7.4 Hz, 1H), 2.60–2.83 (m, 2H), 2.94 (s, 2H), 3.06 (hept, J=6.8 Hz, 1H), 3.63–3.76 (m, 1H), 4.13 (q, J=7.1 Hz, 2H), 4.08–4.30 (m, 2H), 4.42 (broad s, 1H), 6.62 (s, 1H) ppm IR (liquid film): 3480, 2968, 2932, 1738, 1592 cm$^{-1}$ Mass (m/z, %): 392 (M+, 40), 217 (100), 201 (28), 175 (32)

EXAMPLE 21

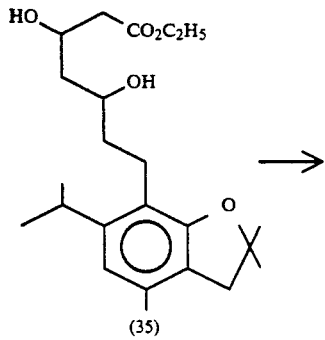

(35)

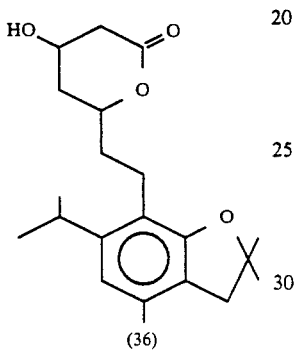

(36)

1.11 g (2.83 mmol) of the Compound No. 35 synthesized in Example 20 was added to 8.0 ml of methanol, followed by stirring in an atmosphere of argon gas at room temperature. To the thus obtained reaction mixture, 1.20 ml (6.00 mmol) of 5N sodium hydroxide was added. The reaction mixture was then stirred for 30 minutes, poured into 1N hydrochloric acid and extracted with ethyl acetate. The thus obtained extract layer was washed with a saturated aqueous solution of sodium chloride three times, dried over magnesium sulfate and concentrated. The concentrated material was dissolved in 12.0 ml of anhydrous toluene and refluxed in an atmosphere of argon gas for 4 hours. The thus obtained reaction mixture was further concentrated, chromatographed on a silica gel column, and eluted with a mixed solvent of hexane and ethyl acetate at a ratio of 1:1, whereby 794 mg of trans-(±)-6-(2,3-dihydro-2,2,4-trimethyl-6-(propan-2-yl)benzo[b]furan-7-yl]ethyl-4-hydroxytetrahydropyran-2-one (Compound No. 36) was obtained in a yield of 81.0%.

Melting Point (°C.): 109.5–110.0 (colorless needles, recrystallized from hexane and ethyl acetate)

¹HNMR (300 MHz, CDCl$_3$): δ 1.20 (d, J=6.8 Hz, 3H), 1.20 (d, J=6.8 Hz, 3H), 1.44 (s, 3H), 1.45 (s, 3H), 1.73–2.07 (m, 4H), 1.87 (d, J=3.2 Hz, 1H), 2.17 (s, 3H), 2.62 (ddd, J=17.4, 4.0 and 1.5 Hz, 1H), 2.61–2.84 (m, 2H), 2.77 (dd, J=17.4 and 5.2 Hz, 1H), 2.89 (s, 2H), 3.10 (hept, J=6.8 Hz, 1H), 4.34–4.46 (m, 1H), 4.66–4.80 (m, 1H), 6.57 (s, 1H) ppm IR (KBr): 3436, 2968, 1694, 1594 cm$^{-1}$ Mass (m/z, %): 346 (M+, 70), 328 (24), 217 (100), 216 (37), 215 (28), 204 (32), 201 (63), 173 (47), 159 (34)

EXAMPLE 22

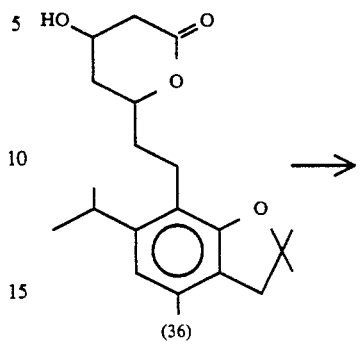

(36)

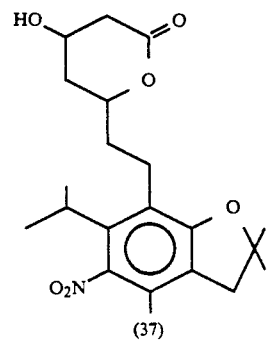

(37)

1.21 g (3.50 mmol) of the Compound No. 36 synthesized in Example 21 was added to 12.0 ml of acetic acid. In an atmosphere of argon gas, 3.50 ml (7.00 mmol) of a 2M nitric acid in acetic acid was further added to the above mixture on a water bath at 15° C., followed by stirring for 15 minutes. The reaction mixture was then poured into water and extracted with ethyl acetate. The thus obtained extract layer was washed successively with an aqueous solution of sodium chloride, an aqueous solution of sodium hydrogencarbonate and a saturated aqueous solution of sodium chloride twice, dried over magnesium sulfate and concentrated. The concentrated material was chromatographed on a silica gel column, and eluted with a mixed solvent of hexane and ethyl acetate at a ratio of 1:1, whereby 948 mg of trams-(±)-6-[2,3-dihydro-2,2,4-trimethyl-5-nitro-6-(propan-2-yl)benzo[b]furan-7-yl]ethyl-4-hydroxytetrahydropyran-2-one (Compound No. 37) was obtained in a yield of 69.9%.

Melting Point (°C.): 144.0–146.0 (light yellow fine particles, recrystallized from hexane and ethyl acetate)

¹HNMR (300 MHz, CDCl$_3$): δ 1.31 (d, J=7.2 Hz, 3H), 1.32 (d, J=7.2 Hz, 3H), 1.47 (s, 3H), 1.47 (s, 3H), 1.40–2.10 (m, 4H), 2.07 (s, 3H), 2.64 (ddd, J=17.6, 3.7 and 1.6 Hz, 1H), 2.64–2.95 (m, 2H), 2.78 (dd, J=17.6 and 5.0 Hz, 1H), 2.92 (s, 2H), 3.00–3.18 (m, 1H), 4.37–4.47 (m, 1H), 4.70–4.83 (m, 1H) ppm IR (KBr): 3456, 2976, 2936, 1706, 1592, 1528 cm$^{-1}$ Mass (m/z, %): 391 (M+, 100), 374 (60), 262 (33), 228 (33), 202 (37)

EXAMPLE 23

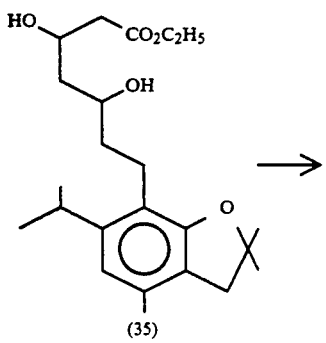

(35)

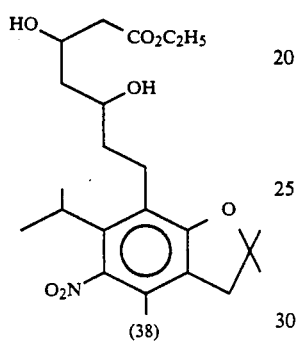

(38)

2.32 g (5.33 mmol) of the Compound No. 35 synthesized in Example 20 was added to 20.0 ml of acetic acid. In an atmosphere of argon gas, 5.90 ml (11.8 mmol) of a 2M nitric acid in acetic acid was further added to the above mixture at a temperature in the range of 14° C. to 13° C., while cooled with water, followed by stirring for 30 minutes. The above reaction mixture was poured into water and extracted with ethyl acetate. The thus obtained extract layer was washed successively with 0.5N sodium hydroxide and a saturated aqueous solution of sodium chloride twice, dried over magnesium sulfate and concentrated. The concentrated material was chromatographed on a silica gel column, and eluted with a mixed solvent of hexane and ethyl acetate at a ratio of 2:1, and then with a mixed solvent of hexane and ethyl acetate at a ratio of 4:3, whereby 1.62 g of ethyl 7-[2,3-dihydro-2,2,4-trimethyl-5-nitro-6-(propan-2-yl)benzo[b]furan-7-yl]-3,5-dihydroxyheptanoate (Compound No. 38) was obtained as a yellow viscosity material in a yield of 74.9%.

$^1$HNMR (300 MHz, CDCl$_3$): δ 1.27 (t, J=7.2 Hz, 3H), 1.28 (d, J=7.6 Hz, 3H), 1.31 (d, J=7.6 Hz, 3H), 1.49 (s, 3H), 1.50 (s, 3H), 1.40–1.80 (m, 4H), 2.07 (s, 3H), 2.44 (dd, J=16.1 and 4.9 Hz, 1H), 2.52 (dd, J=16.1 and 7.8 Hz, 1H), 2.67–2.80 (m, 2H), 2.96 (s, 2H), 3.04–3.24 (m, 1H), 3.74–3.90 (m, 2H), 4.06 (d, J=1.5 Hz, 1H), 4.16 (q, J=7.2 Hz, 2H), 4.20–4.32 (m, 1H) ppm IR (liquid film): 3472, 2976, 2936, 1734, 1592, 1524 cm$^{-1}$ Mass (m/z, %): 437 (M$^+$, 53), 420 (46), 402 (73), 384 (30), 346 (32), 230 (33), 228 (39), 81 (47), 69 (100)

EXAMPLE 24

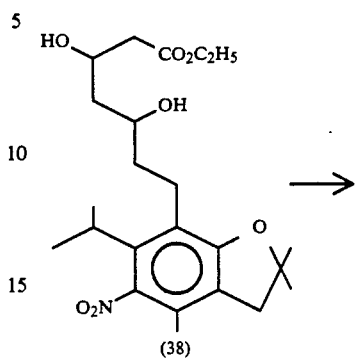

(38)

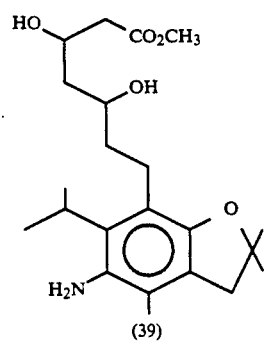

(39)

370 mg (0.85 mmol) of the Compound No. 38 synthesized in Example 23 and 150 mg (0.66 mmol) of platinum dioxide were added to 3.0 ml of methanol, followed by stirring in an atmosphere of hydrogen gas at room temperature for 4 hours and 30 minutes. After the addition of ethyl acetate, the above reaction mixture was filtered through a Celite and concentrated. The thus obtained concentrated material was chromatographed on a silica gel column, and eluted with a mixed solvent of hexane and ethyl acetate at a ratio of 2:3, whereby 210 mg of methyl 7-[5-amino-2,3-dihydro-2,2,4-trimethyl-6-(propan-2-yl)benzo[b]furan-7-yl]-3,5-dihydroxyheptanoate (Compound No. 39) was obtained as a colorless viscosity material in a yield of 63.1%.

$^1$HNMR (300 MHz, CDCl$_3$): δ 1.37 (d, J=7.3 Hz, 3H), 1.39 (d, J=7.3 Hz, 3H), 1.46 (s, 3H), 1.48 (s, 3H), 1.30–1.85 (m, 4H), 2.06 (s, 3H), 2.38 (dd, J=15.3 and 5.6 Hz, 1H), 2.52 (dd, J=15.3 and 7.4 Hz, 1H), 2.56–2.70 (m, 1H), 2.72–2.88 (m, 1H), 2.97 (m, 2H), 3.28–3.48 (m, 1H), 3.60–3.76 (m, 1H), 3.67 (s, 3H), 4.13–4.28 (m, 1H), 4.36–4.64 (m, 2H) ppm IR (liquid film): 3448, 2972, 1736, 1630 cm$^{-1}$ Mass (m/z, %): 393 (M$^+$, 100), 232 (11), 216 (13)

EXAMPLE 25

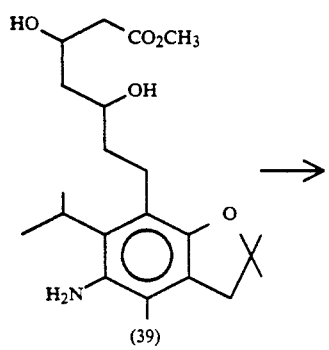

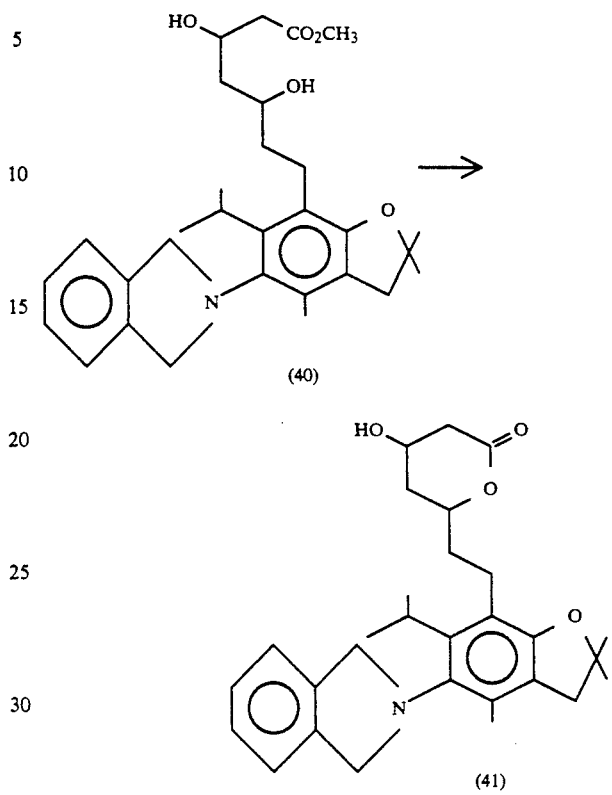

150 mg (0.382 mmol) of the Compound No. 39 synthesized in Example 24, 160 mg (1.16 mmol) of potassium carbonate and 150 mg (0.568 mmol) of α,α'-dibromo-o-xylene were added to 3.0 ml of DMF, followed by stirring in an atmosphere of argon gas for 20 hours. The reaction mixture was poured into a saturated aqueous solution of sodium chloride and extracted with ethyl acetate. The thus obtained extract layer was washed successively with a saturated aqueous solution of sodium chloride three times, dried over magnesium sulfate and concentrated. The concentrated material was chromatographed on a silica gel column, and eluted with a mixed solvent of hexane and ethyl acetate at a ratio of 2:1, whereby 130 mg of methyl 7-[2,3-dihydro-5-(isoindolin-2-yl)-2,2,4-trimethyl-6-(propan-2-yl)benzo[b]furan-7-yl]-3,5-dihydroxyheptanoate (Compound No. 40) was obtained in a yield of 68.8%.

Melting Point (°C.): 136.5–137.5 (colorless fine particles, recrystallized from hexane and ethyl acetate)

$^1$HNMR (300 MHz, CDCl$_3$): δ 1.35 (d, J=7.1 Hz, 6H), 1.49 (s, 3H), 1.50 (s, 3H), 1.42–1.80 (m, 4H), 1.82–1.98 (m, 3H), 2.42 (dd, J=15.5 and 5.4 Hz, 1H), 2.55 (dd, J=15.5 and 7.4 Hz, 1H), 2.64–2.86 (m, 2H), 2.93 (s, 2H), 3.02–3.38 (m, 1H), 3.69 (s, 3H), 3.70–3.86 (m, 1H), 4.16–4.70 (m, 6H), 7.27 (s, 4H) ppm IR (KBr): 3468, 2960, 2928, 1724, 1592 cm$^{-1}$ Mass (m/z, %): 495 (M$^+$, 89), 446 (33), 445 (100), 444 (30), 334 (29), 333 (67), 318 (28)

EXAMPLE 26

116 mg (0.234 mmol) of the Compound No. 40 synthesized in Example 25 was added to 2.0 ml of methanol, and the thus obtained mixture was stirred in an atmosphere of argon gas at 0° C. To the above mixture, 0.10 ml (0.500 mmol) of 5N sodium hydroxide was added. The reaction mixture was then stirred for 30 minutes and poured into diluted hydrochloric acid. Subsequently, an aqueous solution of sodium hydrogencarbonate was added to the above reaction mixture until the pH range thereof was adjusted to 5–6. The above reaction mixture was extracted with ethyl acetate. The thus obtained extract layer was washed with a saturated aqueous solution of sodium chloride twice, dried over magnesium sulfate and concentrated. The concentrated material was dissolved in 3.0 ml of anhydrous toluene and refluxed with the application of heat thereto in an atmosphere of argon gas for 4 hours. The thus obtained reaction mixture was further concentrated, chromatographed on a silica gel column, and eluted with a mixed solvent of hexane and ethyl acetate at a ratio of 4:3, whereby 38 mg of trams-(±)-6-[2,3-dihydro-5-(isoindolin-2-yl)-2,2,4-trimethyl-6-(propan-2-yl)benzo[b]furan-7-yl]ethyl-4-hydroxytetra-hydropyran-2-one (Compound No. 41) was obtained in a yield of 35.0%.

Decomposition Point (°C.): 212.0–214.0 (colorless fine particles, recrystallized from hexane and ethyl acetate)

$^1$HNMR (300 MHz, CDCl$_3$): δ 1.35 (broad d, J=7.1 Hz, 6H), 1.45 (s, 3H), 1.46 (s, 3H), 1.70–2.20 (m, 7H), 2.64 (dd with fine coupling, J=17.4 and 4.4 Hz, 1H), 2.79 (dd, J=17.4 and 5.3 Hz, 1H), 2.63–2.97 (m, 2H), 2.89 (s, 2H), 4.36–4.87 (m, 6H), 7.27 (s, 4H) ppm IR (KBr): 3464, 2974, 2926, 1716 cm$^{-1}$ Mass (m/z, %): 463 (M+, 30), 446 (31), 445 (100), 444 (35), 443 (32), 334 (27), 333 (80), 318 (27), 69 (29)

EXAMPLE 27

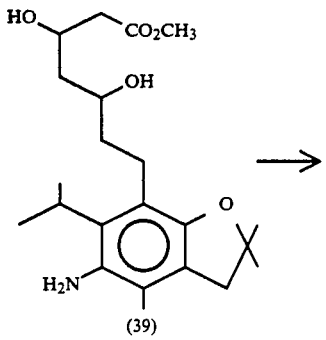

(39)

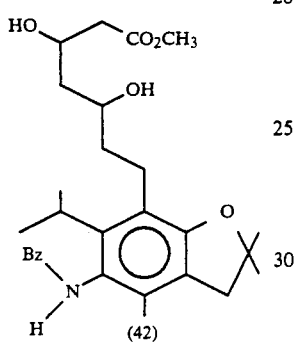

(42)

500 mg (1.27 mmol) of the Compound No. 39 synthesized in Example 24, 530 mg (3.83 mmol) of potassium carbonate and 0.29 ml (2.43 mmol) of benzyl bromide were added to 8.0 ml of DMF, followed by stirring in an atmosphere of argon gas at room temperature for 1 hour and 30 minutes. The thus obtained reaction mixture was poured into a saturated aqueous solution of sodium chloride and extracted with ethyl acetate. The thus obtained extract layer was washed with a saturated aqueous solution of sodium chloride three times, dried over magnesium sulfate and concentrated. The concentrated material was chromatographed on a silica gel column, eluted with a mixed solvent of hexane and ethyl acetate at a ratio of 1:1, whereby 421 mg of methyl 7-[5-benzylamino-2,3-dihydro-2,2,4-trimethyl-6-(propan-2-yl) benzo[b]furan-7-yl]-3,5-dihydroxyheptanoate (Compound No. 42) was obtained in a yield of 68.5%.

Melting Point (°C.): 94.0–94.5 (colorless needles, recrystallized from hexane and ethyl acetate)

$^1$HNMR (300 MHz, CDCl$_3$): δ 1.36 (d, J=7.3 Hz, 6H), 1.48 (s, 3H), 1.50 (s, 3H), 1.40–1.80 (m, 4H), 2.22 (s, 3H), 2.41 (dd, J=15.5 and 5.4 Hz, 1H), 2.53 (dd, J=15.5 and 7.5 Hz, 1H), 2.57–2.90 (m, 2H), 2.97 (s, 2H), 3.00–3.18 (m, 1H), 3.24–3.48 (m, 1H), 3.68 (s, 3H), 3.58–3.73 (m, 1H), 4.00 (broad s, 2H), 4.16–4.60 (m, 3H), 7.24–7.54 (m, 5H) ppm IR (KBr): 3456, 2964, 2936, 1744 cm$^{-1}$ Mass (m/z, %): 483 (M+, 100), 433 (53), 349 (35), 230 (66), 91 (40)

EXAMPLE 28

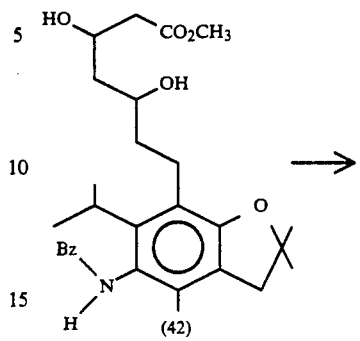

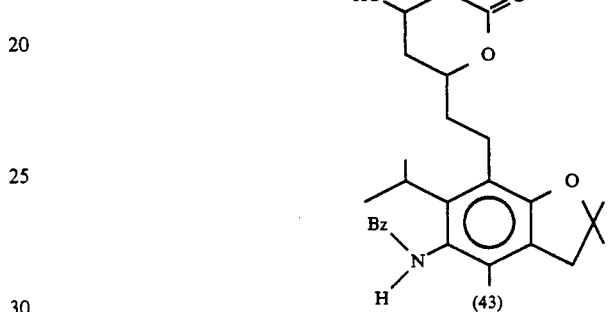

612 mg (1.27 mmol) of the Compound No. 42 synthesized in Example 27 was added to 8.0 ml of methanol, followed by stirring in an atmosphere of argon gas at 0° C. To the thus obtained mixture, 0.5 ml (2.50 mmol) of 5N sodium hydroxide was further added. The reaction mixture was stirred for 15 minutes and poured into diluted hydrochloric acid. Subsequently, an aqueous solution of sodium hydrogencarbonate was added to the above reaction mixture until the pH range thereof was adjusted to 4–5. Then, the reaction mixture was extracted with ethyl acetate. The thus obtained extract layer was washed with a saturated aqueous solution of sodium chloride twice, dried over magnesium sulfate and concentrated. The concentrated material was dissolved in 10.0 ml of anhydrous toluene and refluxed in an atmosphere of argon gas for 4 hours. The thus obtained reaction mixture was further concentrated, chromatographed on a silica gel column, and eluted with a mixed solvent of hexane and ethyl acetate at a ratio of 1:1, whereby 450 mg of trans-(±)-6-[5-benzylamino-2,3-dihydro-2,2,4-trimethyl-6-(propan-2-yl)benzo[b]furan-7-yl]ethyl-4-hydroxytetrahydropyran-2-one (Compound No. 43) was obtained in a yield of Melting Point (°C.): 161.5–163.0 (colorless columns, recrystallized from hexane and ethyl acetate)

$^1$HNMR (300 MHz, CDCl$_3$): δ 1.37 (d, J=7.3 Hz, 3H), 1.38 (d, J=7.3 Hz, 3H), 1.44 (s, 3H), 1.45 (s, 3H), 1.74–2.10 (m, 4H), 2.19 (s. 3H), 2.63 (d with fine coupling, J=17.5, 1H), 2.78 (dd, J=17.5 and 5.1 Hz, 1H), 2.60–3.00 (m, 2H), 2.92 (s, 2H), 3.95 (broad s, 2H), 4.36–4.48 (m, 1H), 4.68–4.86 (m, 1H), 7.28–7.51 (m, 5H) ppm IR (KBr): 3548, 2972, 2928, 1718 cm$^{-1}$ Mass (m/z, %): 451 (M+, 58), 433 (49), 361 (21), 230 (100), 91 (74)

EXAMPLE 29

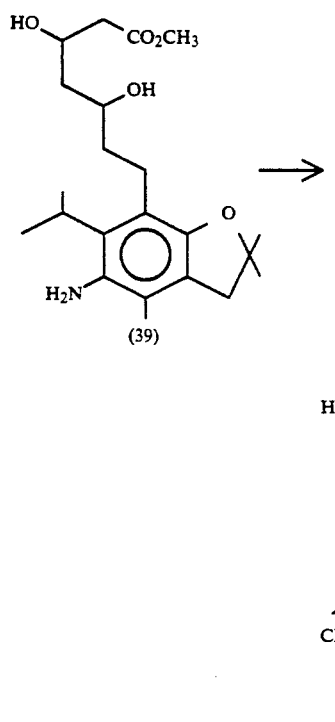

143 mg (0.364 mmol) of the Compound No. 39 synthesized in Example 24, 115 mg (0.832 mmol) of potassium carbonate and 0.10 ml (1.61 mmol) of methyl iodide were added to 2.0 ml of DMF, followed by stirring in an atmosphere of argon gas for 30 minutes at room temperature. The thus obtained reaction mixture was poured into water and extracted with ethyl acetate. The thus obtained extract layer was washed with a saturated aqueous solution of sodium chloride twice, dried over magnesium sulfate and concentrated. The concentrated material was chromatographed on a silica gel column, and eluted with a mixed solvent of hexane and ethyl acetate at a ratio of 1:1, whereby 61 mg of methyl 7-[2,3-dihydro-2,2,4-trimethyl-5-methylamino-6-(propan-2-yl)benzo[b]furan-7-yl]-3,5-dihydroxyheptanoate (Compound No. 44) was obtained in a yield of 41.2%.

Melting Point (°C.): 79.5–81.0 (colorless needles, recrystallized from hexane and ethyl acetate)

$^1$HNMR (300 MHz, CDCl$_3$): δ 1.34 (d, J=7.3 Hz, 6H), 1.47 (s, 3H), 1.49 (s, 3H), 1.40–1.78 (m, 4H), 2.16 (s, 3H), 2.39 (dd, J=15.5 and 5.4 Hz, 1H), 2.52 (dd, J=15.5 and 7.5 Hz, 1H), 2.67 (s, 3H), 2.60–2.86 (m, 2H), 2.95 (s, 2H), 3.20–3.50 (m, 1H), 3.68 (s, 3H), 3.58–3.82 (m, 1H), 4.16–4.30 (m, 1H), 4.30–4.62 (m, 2H) ppm IR (KBr): 3440, 2932, 1745 cm$^{-1}$ Mass (m/z, %): 407 (M+, 100), 375 (25), 357 (14)

Example 30

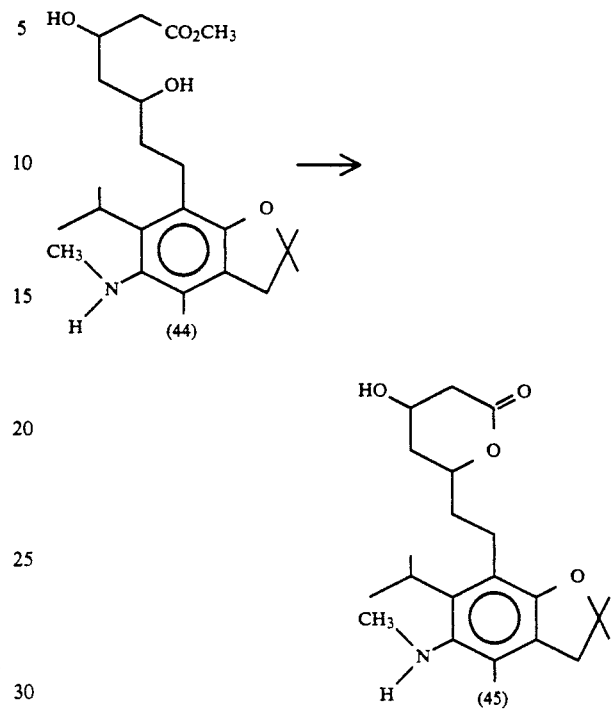

105 mg (0.258 mmol) of the Compound No. 44 synthesized in Example 29 was added to 2.0 ml of methanol, followed by stirring in an atmosphere of argon gas at 0° C. To the thus obtained mixture, 0.15 ml (0.750 mmol) of 5N sodium hydroxide was further added. The reaction mixture was then stirred for 40 minutes and poured into diluted hydrochloric acid. Subsequently, an aqueous solution of sodium hydrogencarbonate was added to the above reaction mixture until the pH range thereof was adjusted to 4–5. Then, the reaction mixture was extracted with ethyl acetate. The thus obtained extract layer was washed with a saturated aqueous solution of sodium chloride twice, dried over magnesium sulfate and concentrated. The concentrated material was dissolved in 3.0 ml of anhydrous toluene and refluxed in an atmosphere of argon gas for 5 hours and 30 minutes. The thus obtained reaction mixture was further concentrated, chromatographed on a silica gel column, and eluted with a mixed solvent of hexane and ethyl acetate at a ratio of 1:1, whereby 78 mg of trans-(±)-6-[2,3-dihydro-2,2,4-trimethyl-5-methylamino-6-(propan-2-yl)benzo[b]furan-7-yl]ethyl-4-hydroxytetrahydropyran-2-one (Compound No. 45) was obtained as a colorless amorphous solid in a yield of 80.6%.

$^1$HNMR (300 MHz, CDCl$_3$): δ 1.35 (d, J=7.3 Hz, 3H), 1.36 (d, J=7.3 Hz, 3H), 1.43 (s, 3H), 1.44 (s, 3H), 1.74–2.10 (m, 4H), 2.15 (s, 3H), 2.56–2.94 (m, 4H), 2.65 (s, 3H), 2.90 (s, 2H), 3.25–3.75 (m, 1H), 4.36–4.44 (m, 1H), 4.66–4.84 (m, 1H) ppm IR (KBr): 3464, 2970, 2934, 1728, 1596 cm$^{-1}$ Mass (m/z, %): 375 (M+, 100), 357 (15), 231 (23), 230 (28)

REFERENCE EXAMPLE 9

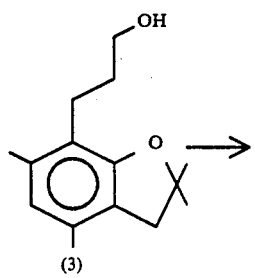

(3)

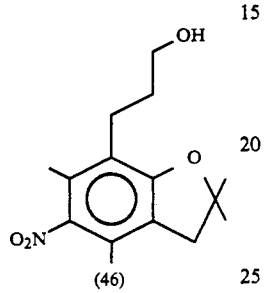

(46)

5.36 g (22.9 mmol) of the Compound No. 3 synthesized in Reference Example 2 was dissolved in 25 ml of acetic acid, and 17.2 ml (34.4 mmol) of a 2M nitric acid in acetic acid was added dropwise thereto in an atmosphere of argon gas at 10° C. over a 20-minutes period. The thus obtained mixture was stirred for 1 hour and 30 minutes, poured into water, and extracted with ethyl acetate. The thus obtained extract layer was washed successively with a saturated aqueous solution of sodium hydrogencarbonate, 0.5N sodium hydroxide, water and a saturated aqueous solution of sodium chloride, dried over magnesium sulfate, and concentrated. The concentrated material was dissolved in 40 ml of methanol. After the addition of 20 ml of 5N sodium hydroxide, the reaction mixture was stirred at 0° C. for 30 minutes, and then at room temperature for 1 day. The obtained reaction mixture was poured into 1N hydrochloric acid and extracted with ethyl acetate. The thus obtained extract layer was washed successively with water and a saturated aqueous solution of sodium chloride, dried over magnesium sulfate and concentrated. The concentrated material was chromatographed on a silica gel column, and eluted with a mixed solvent of ethyl acetate and hexane at a ratio of 1:1, whereby 3.42 g of 3-[2,3-dihydro-2,2,4,6-tetramethyl-5-nitrobenzo[b]furan-7-yl]propanol (Compound No. 46) was obtained as a yellow oily material in a yield of 53.5%.

$^1$HNMR (300 MHz, CDCl$_3$): δ 1.50 (s, 6H), 1.70–1.80 (m, 2H), 2.13 (s, 3H), 2.19 (s, 3H), 2.70 (t, J=7.0 Hz, 2H), 2.97 (s, 2H), 3.53 (t, J=6.0 Hz, 2H) ppm IR (liquid film): 3396, 2972, 2936 cm$^{-1}$ Mass (m/z, %): 279 (M$^+$, 100), 262 (63), 234 (62), 216 (67), 173 (38), 128 (54), 115 (60), 91 (66), 77 (39)

REFERENCE EXAMPLE 10

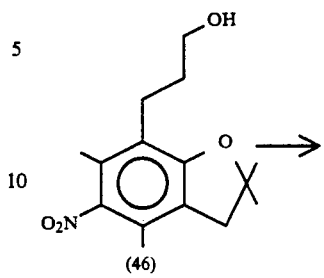

(46)

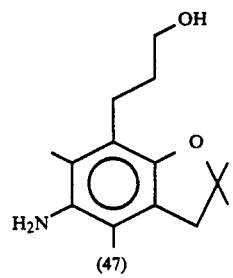

(47)

1.88 g (6.75 mmol) of the Compound No. 46 synthesized in Reference Example 9 was dissolved in a mixed solvent containing 25 ml of methanol and 12.5 ml of water. 90 mg of a 10% Pd/C was added to the above solution. Thereafter, 510 mg (13.5 mmol) of sodium borohydride was added to the above obtained mixture in an atmosphere of argon gas at room temperature over a 10-minutes period, followed by stirring for 3 hours and 30 minutes. After the addition of ethyl acetate, the reaction mixture was filtered through a Celite. The filtrate was dissolved in a saturated aqueous solution of ammonium chloride and extracted with ethyl acetate. The thus obtained extract layer was washed with a saturated aqueous solution of sodium chloride, dried over magnesium sulfate and concentrated. The concentrated material was chromatographed on a silica gel column, and eluted with ethyl acetate, whereby 1.36 g of 3-[5-amino-2,3-dihydro-2,2,4,6-tetramethylbenzo[b]furan-7-yl]propanol (Compound No. 47) was obtained in a yield of 80.9%.

Melting Point (°C.): 102.0–103.0 (colorless columns, recrystallized from ethyl acetate and hexane)

$^1$HNMR (300 MHz, CDCl$_3$): δ 1.46 (s, 6H), 1.67–1.79 (m, 2fi), 2.06 (s, 3H), 2.10 (s, 3H), 2.69–2.77 (m, 2H), 2.96 (s, 2H), 3.02–3.15 (m, 1H), 3.20–3.38 (m, 2H), 3.45–3.53 (m, 2H) ppm IR (KBr): 3394, 3196, 2976, 2922, 2866, 1628 cm$^{-1}$ Mass (m/z, %): 249 (M$^+$, 100), 204 (19), 189 (15), 174 (7), 146 (3), 130 (2), 91 (2)

REFERENCE EXAMPLE 11

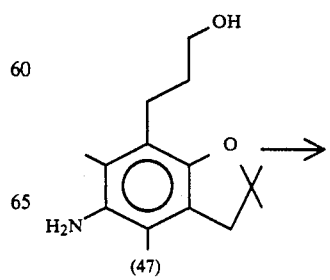

(47)

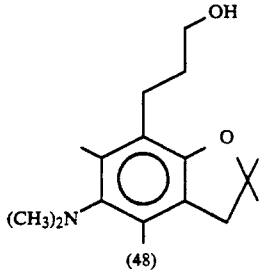

1.00 g (4.0 mmol) of the Compound No. 47 synthesized in Reference Example 10 was dissolved in 10 ml of DMF. 2.21 g (16.0 mmol) of potassium carbonate and 1.0 ml (16.0 mmol) of methyl iodide were successively added to the above solution, followed by stirring overnight in an atmosphere of argon gas at room temperature. The above reaction mixture was poured into water and extracted with hexane. The thus obtained extract layer was washed with a saturated aqueous solution of sodium chloride, dried over magnesium sulfate and concentrated. The concentrated material was chromatographed on a silica gel column, and eluted with a mixed solvent of ethyl acetate and hexane at a ratio of 1:2, whereby 917 mg of 3-[2,3-dihydro-2,2,4,6-tetramethyl-5-dimethylaminobenzo[b]furan-7-yl]propanol (Compound No. 48) was obtained as a colorless oily material in a yield of 82.8%.

$^1$HNMR (300 MHz, CDCl$_3$): δ 1.47 (s, 6H), 1.70-1.80 (m, 2H), 2.12 (s, 3H), 2.19 (s, 3H), 2.68 (t, J=6.7 Hz, 2H), 2.79 (s, 6H), 2.87-2.94 (m, 2H), 2.92 (s, 2H), 3.46-3.55 (m, 2H) ppm IR (liquid film): 3460, 2972, 2928 cm$^{-1}$ Mass (m/z, %): 277 (M+, 100), 262 (11), 232 (15), 218 (13), 189 (7), 147 (5), 91 (4)

REFERENCE EXAMPLE 12

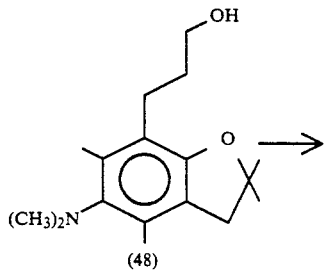

861 mg (3.11 mmol) of the Compound No. 48 synthesized in Example 11 was dissolved in a mixed solvent containing 10 ml of dimethyl sulfoxide and 2.5 ml of anhydrous THF. 2.42 ml (17.4 mmol) of triethylamine and 2.21 g (13.9 mmol) of sulfur trioxide pyridine complex were successively added to the above mixture, followed by stirring in an atmosphere of argon gas at room temperature for 1 hour. The reaction mixture was then poured into 0.5N hydrochloric acid and extracted with ethyl acetate. An aqueous layer was neutralized to have the pH range of 5-6, and further extracted with ethyl acetate. A mixture of the thus obtained extract layers was washed successively with water and a saturated aqueous solution of sodium chloride, dried over magnesium sulfate and concentrated. The concentrated material was chromatographed on a silica gel column, and eluted with a mixed solvent of ethyl acetate and hexane at a ratio of 1:6, whereby 652 mg of 3-[2,3-dihydro-2,2,4,6-tetramethyl-5-dimethylaminobenzo[b]furan-7-yl]propanal (Compound No. 49) was obtained as a colorless oily material in a yield of 76.2%.

$^1$HNMR (300 MHz, CDCl$_3$): δ 1.43 (s, 6H), 2.11 (s, 3H), 2.19 (s, 3H), 2.61 (dd, J=7.8 and 1.8 Hz, 1H), 2.78 (s, 6H), 2.85-2.90 (m, 2H), 2.88 (s, 2H), 9.82 (t, J=1.8 Hz, 1H) ppm IR (KBr): 2972, 2928, 1728 cm$^{-1}$ Mass (m/z, %): 275 (M+, 100), 260 (13), 232 (36), 219 (13), 218 (12), 188 (9), 173 (7), 91 (7)

REFERENCE EXAMPLE 13

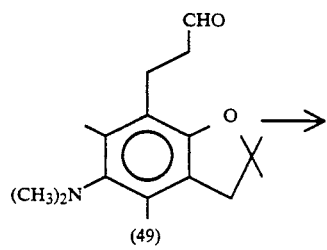

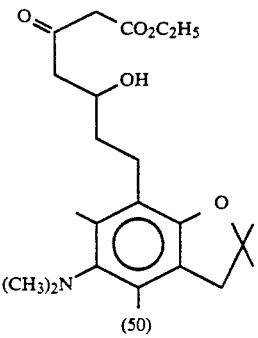

129 mg (3.22 mmol) of a 60% sodium hydride was suspended in 5 ml of anhydrous THF in an atmosphere of argon gas at 0° C. After the addition of 0.41 ml (3.22 mmol) of ethyl acetoacetate, the thus obtained mixture was stirred for 40 minutes. Then, 2.06 ml (3.22 mmol) of a 15% hexane solution of butyl lithium was further added to the above mixture. The reaction mixture was then stirred for 30 minutes and cooled to −78° C. A solution of 590 mg (2.15 mmol) of the Compound No. 49 synthesized in Reference Example 12 in 3 ml of anhydrous THF was added to the above reaction mixture, followed by stirring for 2 hours. The above obtained reaction mixture was poured into a saturated aqueous solution of ammonium chloride and extracted with ethyl acetate. The thus obtained extract layer was washed successively with water and a saturated aqueous solution of sodium chloride, dried over magnesium sulfate and concentrated. The concentrated material was chromatographed on a silica gel column, and eluted with a mixed solvent of ethyl acetate and hexane at a ratio of 1:3, whereby 445 mg of ethyl 7-[2,3-dihydro- 2,2,4,6-tetramethyl-5-dimethylaminobenzo[b]furan-7-yl]-5-hydroxy-3-oxoheptanoate (Compound No. 50) was obtained as a light yellow oily material in a yield of 51.1%.

$^1$HNMR (300 MHz, CDCl$_3$): δ 1.26 (t, J=7.2 Hz, 3H), 1.45 (s, 3H), 1.46 (s, 3H), 1.55-1.75 (m, 2H), 2.11 (s, 3H), 2.18 (s, 3H), 2.50-2.80 (m, 4H), 2.78 (s, 3H), 2.79 (s, 3H), 2.90 (s, 2H), 3.50 (s, 2H), 3.67 (d, J=3.6 Hz, 1H), 3.85-3.96 (m, 1H), 4.17 (q, J=7.2 Hz, 1H) ppm IR (liquid film): 3520, 2912, 2784, 1744 cm$^{-1}$ Mass (m/z, %): 405 (M$^+$, 100), 359 (24), 275 (34), 232 (49), 217 (21), 202 (16), 188 (17), 173 (13), 159 (12), 115 (12), 43 (21)

EXAMPLE 31

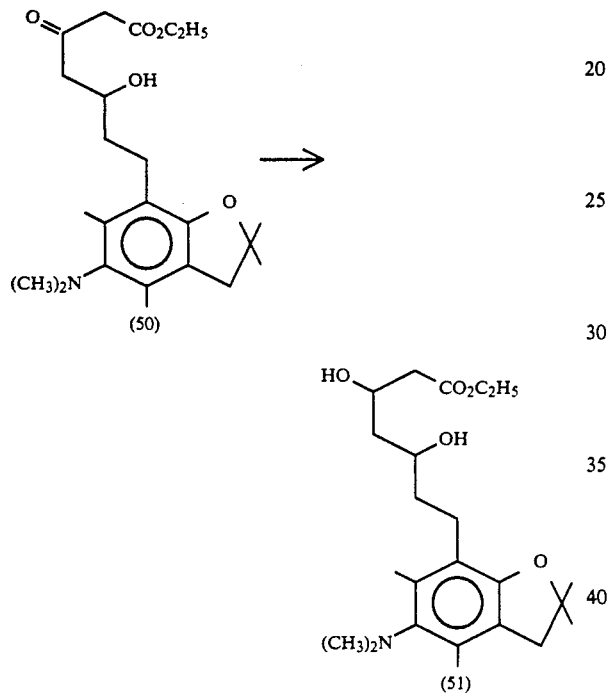

1.49 ml (1.49 mmol) of a 1.0M THF solution of triethylborane was added to 10 mg (0.1 mmol) of pivalic acid, followed by stirring in an atmosphere of argon gas at room temperature for 1 hour. Subsequently, a solution of 401 mg (0.1 mmol) of the Compound No. 50 synthesized in Reference Example 13 in 4 ml of anhydrous THF was added to the above mixture. The thus obtained mixture was stirred for 50 minutes and cooled to −78° C. After the addition of 1.5 ml of methanol and 45 mg (1.2 mmol) of sodium borohydride, the reaction mixture was stirred for 1 hour and 35 minutes and allowed to warm the mixture to 0° C. After the addition of 4 ml of a 30% aqueous hydrogen peroxide, the reaction mixture was further stirred overnight, poured into a saturated aqueous solution of ammonium chloride and extracted with ethyl acetate. The thus obtained extract layer was washed successively with water, a saturated solution of sodium thiosulfate, water and a saturated aqueous solution of sodium chloride, dried over magnesium sulfate, and concentrated. The concentrated material was chromatographed on a silica gel column, and eluted with a mixed solvent of ethyl acetate and hexane at a ratio of 1:1, whereby 241 mg of ethyl 7-[2,3-dihydro-2,2,4,6-tetramethyl-5-dimethylaminobenzo[b]furan-7-yl]-3,5-dihydroxyheptanoate (compound No. 51) was obtained as a yellow oily material in a yield of 59.8%.

$^1$HNMR (300 MHz, CDCl$_3$): δ 1.24 (t, J=7.1 Hz, 3H), 1.47 (s, 3H), 1.49 (s, 3H), 1.50-1.75 (m, 4H), 2.12 (s, 3H), 2.18 (s, 3H), 2.37 (dd, J=15.6 and 5.9 Hz, 1H), 2.52 (dd, J=15.6 and 7.2 Hz, 1H), 2.54-2.63 (m, 1H), 2.70-2.80 (m, 1H), 2.78 (s, 3H), 2.80 (s, 3H), 2.93 (s, 2H), 3.61-3.75 (m, 1H), 4.13 (q, J=7.1 Hz, 2H), 4.15-4.28 (m, 1H), 4.32 (s with fine coupling, 1H), 4.48 (s, 1H) ppm IR (liquid film): 3468, 2976, 2932, 2784, 1738 cm$^{-1}$ Mass (m/z, %): 407 (M$^+$, 100), 362 (7), 335 (4), 232 (23), 217 (9), 202 (6), 188 (7), 173 (3), 117 (3), 43 (5)

EXAMPLE 32

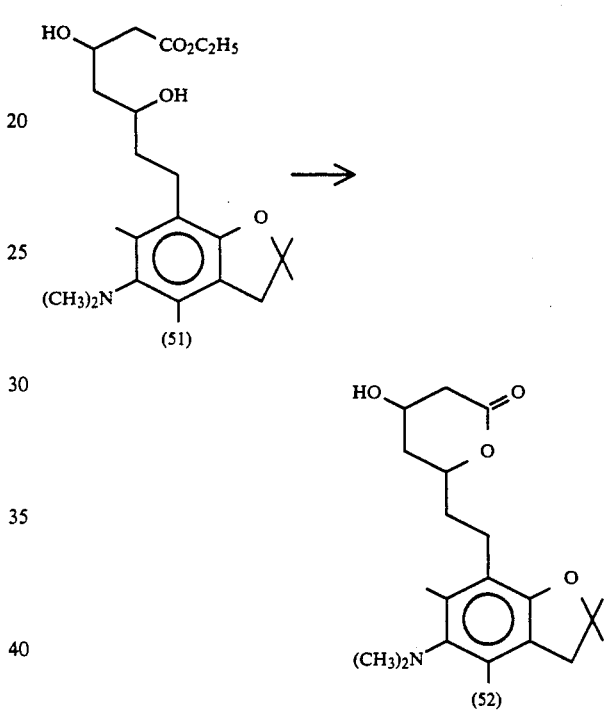

233 mg (0.572 mmol) of the Compound No. 51 synthesized in Example 31 was dissolved in 3 ml of methanol. 0.34 ml (1.7 mmol) of 5N sodium hydroxide was added to the above mixture, followed by stirring overnight in an atmosphere of argon gas at room temperature. The thus obtained reaction mixture was poured into a saturated aqueous solution of ammonium chloride and extracted with ethyl acetate. The thus obtained extract layer was washed successively water and a saturated aqueous solution of sodium chloride, dried over magnesium sulfate and concentrated. The concentrated material was dissolved in 5 ml of anhydrous toluene and refluxed in an atmosphere of argon gas for 6 hours. The thus obtained reaction mixture was concentrated, chromatographed on a silica gel column, and eluted with ethyl acetate, whereby 43 mg of trans-(±)-6-[2,3-dihydro-2,2,4,6-tetramethyl-5-dimethylaminobenzo[b]furan-7-yl]ethyl-4-hydroxytetrahydropyran-2-one (Compound No. 52) was obtained as a light yellow oily material in a yield of 20.8%.

$^1$HNMR (300 MHz, CDCl$_3$): δ 1.43 (s, 3H), 1.44 (s, 3H), 1.70-1.98 (m, 4H), 1.99-2.07 (m, 1H), 2.11 (s, 3H), 2.20 (s, 3H), 2.56-2.80 (m, 4H), 2.78 (s, 6H), 2.88 (s, 2H), 4.35-4.44 (m, 1H), 4.65-4.76 (m, 1H) ppm IR (liquid film): 3456, 2928, 2784, 1730 cm$^{-1}$ Mass (m/z, %): 361 (M+, 100), 343 (18), 232 (19), 216 (15), 202 (9), 188 (9), 173 (7), 91 (6), 43 (7)

REFERENCE EXAMPLE 14

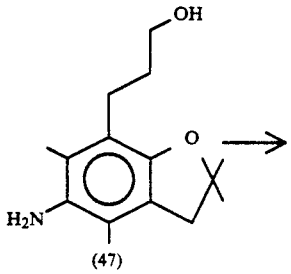

(47)

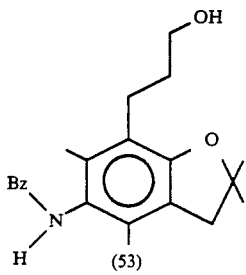

(53)

1.36 g (5.46 mmol) of the Compound No. 47 synthesized in Reference Example 10 was dissolved in 10 ml of ethanol, and 1.39 ml (13.7 mmol) of benzaldehyde was added thereto. The above reaction mixture was stirred overnight in an atmosphere of argon gas at room temperature, concentrated, and dissolved in a mixed solvent of 7 ml of methanol and 15 ml of methylene chloride. 619 mg (16.4 mmol) of sodium borohydride was then added to the above reaction mixture in an atmosphere of argon gas at 0° C. 10 minutes later, the reaction mixture was allowed to warm to room temperature, and stirred for 1 hour and 30 minutes. After the addition of a small amount of acetone, the reaction mixture was stirred to quench excess NaBH₄, poured into a saturated aqueous solution of ammonium chloride, and extracted with ethyl acetate. The thus obtained extract layer was washed successively with water and a saturated aqueous solution of sodium chloride, dried over magnesium sulfate and concentrated. The concentrated material was chromatographed on a silica gel column, and eluted with a mixed solvent of ethyl acetate and hexane at a ratio of 1:2, whereby 1.27 g of 3-[5-benzylamino-2,3-dihydro-2,2,4,6-tetramethylbenzo-[b]furan-7-yl]propanol (Compound No. 53) was obtained in a yield of 79.9%.

Melting Point (°C.): 38.0-39.0 (colorless needles, recrystallized from ethyl acetate and hexane)

¹HNMR (300 MHz, CDCl₃): δ 1.49 (s, 6H), 1.70-1.80 (m, 2H), 2.15 (s, 3H), 2.23 (s, 3H), 2.68-2.76 (m, 2H), 2.88-3.03 (m, 1H), 2.96 (s, 2H), 3.46-3.54 (m, 2H), 3.94 (s, 2H), 7.27-7.44 (m, 5H) ppm IR (KBr): 3460, 2936 cm⁻¹

Mass (m/z, %): 339 (M+, 30), 248 (40), 233 (40), 204 (37), 189 (27), 174 (22), 91 (100)

REFERENCE EXAMPLE 15

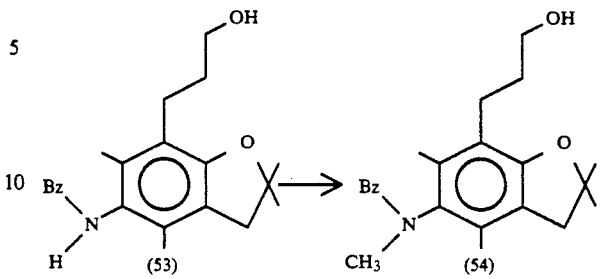

1.27 g (3.75 mmol) of the Compound No. 53 synthesized in Reference Example 14 was dissolved in 20 ml of DMF. To this solution, 2.59 g (18.8 mmol) of potassium carbonate was added. Subsequently, with the addition of 1.40 ml (22.5 mmol) of methyl iodide, the reaction mixture was stirred overnight in an atmosphere of argon gas at room temperature, poured into water and extracted with hexane. The thus obtained extract layer was washed successively with water and a saturated aqueous solution of sodium chloride, dried over magnesium sulfate and concentrated. The concentrated material was chromatographed on a silica gel column, and eluted with a mixed solvent of ethyl acetate and hexane at a ratio of 1:6, and then with a mixed solvent of ethyl acetate and hexane at a ratio of 1:3, whereby 1.10 g of 3-[5-(N-benzyl-N-methylamino)-2,3-dihydro-2,2,4,6-tetramethylbenzo[b]furan-7-yl]propanol (Compound No. 54) was obtained as a colorless oily material in a yield of 68.4%.

¹HNMR (300 MHz, CDCl₃): δ 1.49 (s, 3H), 1.49 (s, 3H), 1.67-1.83 (m, 2H), 2.20 (s, 3H), 2.27 (s, 3H), 2.66 (s, 3H), 2.71 (t, J=6.7 Hz, 2H), 2.90 (t, J=7.0 Hz, 1H), 2.94 (s, 2H), 3.44-3.58 (m, 2H), 4.14 (s, 2H), 7.20-7.43 (m, 5H) ppm IR (liquid film): 3464, 2972, 2932, 1592 cm⁻¹

Mass (m/z, %): 353 (M+, 81), 262 (100), 218 (42), 91 (44)

REFERENCE EXAMPLE 16

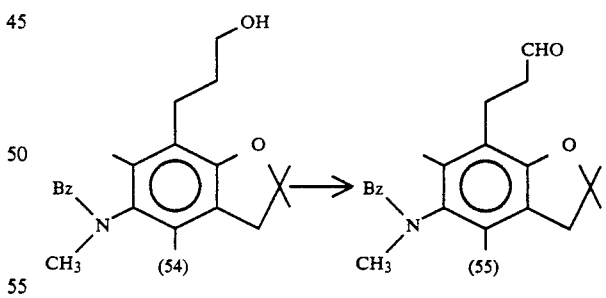

962 mg (2.73 mmol) of the Compound No. 54 synthesized in Reference Example 15 was added to 10.0 ml of dimethyl sulfoxide, followed by stirring in an atmosphere of argon gas at room temperature. To this mixture, 1.33 ml (9.54 mmol) of triethylamine, 3.0 ml of anhydrous THF and 1.30 g (8.17 mmol) of sulfur trioxide pyridine complex were successively added. The mixture was stirred for 20 minutes, poured into diluted hydrochloric acid, and extracted with ethyl acetate. The thus obtained extract layer was washed with a saturated aqueous solution of sodium chloride three times, dried over magnesium sulfate and concentrated. The concentrated material was chromatographed on a silica gel column and eluted with a mixed solvent of hexane and ethyl acetate at a ratio of 15:1, whereby 800 mg of 3-[5-(N-benzyl-N-methylamino)-2,3-dihydro-2,2,4,6-tetramethylbenzo[b]furan-7-yl]propanal (Compound No. 55) was obtained as a colorless amorphous solid in a yield of 83.6%.

$^1$HNMR (300 MHz, CDCl$_3$): δ 1.45 (s, 6H), 2.19 (s, 3H), 2.27 (s, 3H), 2.57–2.67 (m, 2H), 2.65 (s, 3H), 2.84–2.94 (m, 2H), 2.90 (s, 2H), 4.13 (s, 2H), 7.20–7.42 (m, 5H), 9.82 (t, J=1.8 Hz, 1H) ppm IR (KBr): 3488, 2972, 2932, 1726, 1592 cm$^{-1}$ Mass (m/z, %): 351 (M+, 70), 260 (100), 218 (38), 91 (42)

REFERENCE EXAMPLE 17

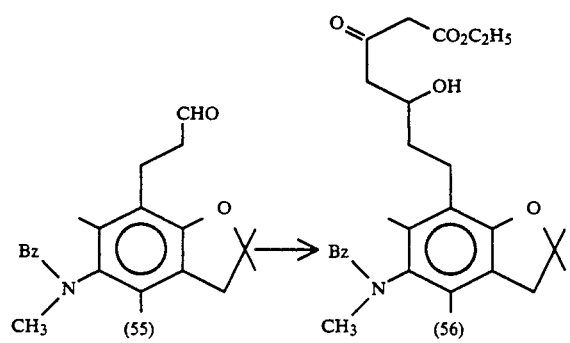

128 mg (3.20 mmol) of a 60% sodium hydride was suspended in 5.0 ml of anhydrous THF. To this suspension, 0.41 ml (3.22 mmol) of ethyl acetoacetate was added in a stream of argon gas at room temperature, followed by stirring for 20 minutes. The thus obtained mixture was cooled to 0° C., and 2.0 ml (3.13 mmol) of a 15% hexane solution of butyl lithium was added thereto. Furthermore, this mixture was stirred for 25 minutes, and cooled to −78° C. 728 mg (2.07 mmol) of the Compound No. 55 synthesized in Reference Example 16 was dissolved in 12.0 ml of anhydrous THF. This solution was added to the above obtained mixture over a period of 20 minutes. The thus obtained reaction mixture was further stirred for 1 hour, poured into a saturated aqueous solution of sodium chloride, and extracted with ethyl acetate. The thus obtained extract layer was washed with a saturated aqueous solution of sodium chloride three times, dried over magnesium sulfate and concentrated. The concentrated material was chromatographed on a silica gel column, and eluted with a mixed solvent of hexane and ethyl acetate at a ratio of 4:1, whereby 738 mg of ethyl 7-15-(N-benzyl-N-methylamino)-2,3-dihydro-2,2,4,6-tetramethylbenzo[b-]furan-7-yl]-5-hydroxy-3-oxoheptanoate (Compound No. 56) was obtained as a colorless oily material in a yield of 74.0%.

$^1$HNMR (300 MHz, CDCl$_3$): δ 1.26 (t, J=7.2 Hz, 3H), 1.47 (s, 6H), 1.50–1.75 (m, 2H), 2.19 (s with fine coupling, 3H), 2.26 (s, 3H), 2.50–2.84 (m, 4H), 2.66 (d, J=2.1 Hz, 3H), 2.93 (s, 2H), 3.50 (s, 2H), 3.66 (t, J=3.9 Hz, 1H), 3.83–3.98 (m, 1H), 4.13 (d, J=5.7 Hz, 2H), 4.17 (q, J=7.2 Hz, 2H), 7.20–7.42 (m, 5H) ppm IR (liquid film): 3524, 2976, 2932, 1742, 1716, 1648 cm$^{-1}$ Mass (m/z, %): 481 (100, M+), 390 (24), 260 (23), 218 (38), 216 (52), 91 (53)

EXAMPLE 33

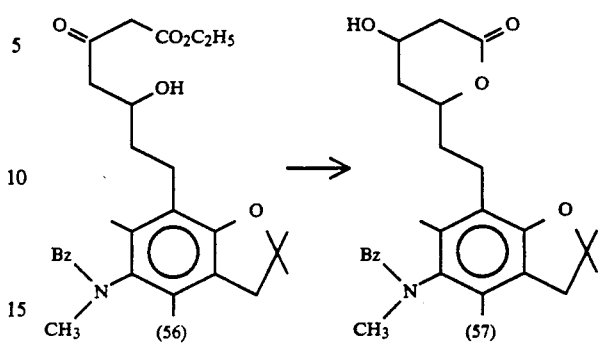

10 mg (0.098 mmol) of pivalic acid was added to 2.20 ml (2.20 mmol) of a 1.0M THF solution of triethylborane in an atmosphere of argon gas at room temperature, followed by stirring for 1 hour and 20 minutes. 721 mg (1.50 mmol) of the Compound No. 56 synthesized in Reference Example 17 was dissolved in 10.0 ml of anhydrous THF. This solution was added to the above obtained mixture, stirred for 1 hour and 25 minutes, and cooled to −78° C. Then, 2.0 ml of methanol and 62 mg (1.64 mmol) of sodium borohydride were successively added to the above mixture. The reaction mixture was stirred for 1 hour and 30 minutes, and gradually added to 10.0 g of a 30% aqueous hydrogen peroxide at 0° C. The reaction mixture was further stirred for 2 hours, poured into water and extracted with ethyl acetate. The thus obtained extract layer was washed successively with a saturated aqueous solution of sodium chloride, an aqueous solution of sodium thiosulfate and a saturated aqueous solution of sodium chloride three times, dried over magnesium sulfate, and concentrated. To the concentrated material 7.0 ml of methanol was added and stirred in an atmosphere of argon gas at room temperature. After the addition of 0.60 ml (3.00 mmol) of 5N sodium hydroxide, the thus obtained mixture was further stirred for 45 minutes and poured into diluted hydrochloric acid. Subsequently, an aqueous solution of sodium hydrogencarbonate was added to the above mixture until the pH range thereof was adjusted to 4–5, and this reaction mixture was extracted with ethyl acetate. The thus obtained extract layer was washed with a saturated aqueous solution of sodium chloride twice, dried over magnesium sulfate, and concentrated. The concentrated material was dissolved in 5.0 ml of anhydrous toluene and refluxed in an atmosphere of argon gas for 3 hours and 15 minutes. The thus obtained reaction mixture was further concentrated, chromatographed on a silica gel column and eluted with a mixed solvent of hexane and ethyl acetate at a ratio of 1:1, whereby 505 mg of trans-(±)-6-[5-(N-benzyl-N-methylamino)-2,3-dihydro-2,2,4,6-tetramethylbenzo[b-]furan-7-yl]ethyl-4-hydroxytetrahydropyran-2-one (Compound No. 57) was obtained as a colorless oily material in a yield of 77.1%.

$^1$HNMR (300 MHz, CDCl$_3$): δ 1.45 (s, 6H), 1.60–2.10 (m, 4H), 2.19 (s, 3H), 2.29 (s, 3H), 2.56–2.84 (m, 4H), 2.65 (s, 3H), 2.90 (s, 2H), 4.13 (s, 2H), 4.33–4.46 (m, 1H), 4.64–4.78 (m, 1H), 7.20–7.47 (m, 5H) ppm IR (liquid film): 3450, 2970, 2930, 1723, 1709, 1590 cm$^{-1}$ Mass (m/z, %): 437 (M+, 100), 419 (37), 346 (33), 216 (87), 91 (56)

REFERENCE EXAMPLE 18

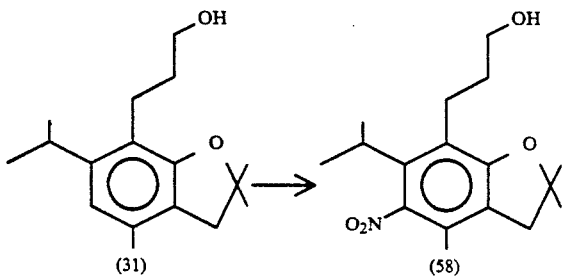

3.00 g (11.5 mmol) of the Compound No. 31 synthesized in Reference Example 6 was added to 30.0 ml of acetic acid. In an atmosphere of argon gas, 12.0 ml (24.0 mmol) of a 2M nitric acid in acetic acid was further added to the above mixture on a water bath at 14° to 13° C., followed by stirring for 1 hour and 20 minutes. The thus obtained reaction mixture was poured into water and extracted with ethyl acetate. The thus obtained extract layer was washed successively with 0.5N sodium hydroxide and a saturated aqueous solution of sodium chloride twice, dried over magnesium sulfate, and concentrated. The concentrated material was chromatographed on a silica gel column, and eluted with a mixed solvent of hexane and ethyl acetate at a ratio of 4:1, whereby 2.21 g of 3-[2,3-dihydro-2,2,4-trimethyl-5-nitro-6-(propan-2-yl)benzo[b]furan-7-yl]propanol (Compound No. 58) was obtained in a yield of 62.9%.

Melting Point (°C.): 75.0–76.0 (yellow needles, recrystallized from hexane and ethyl acetate)

$^1$HNMR (300 MHz, CDCl$_3$): δ 1.30 (d, J=7.2 Hz, 6H), 1.50 (s, 6H), 1.72–1.84 (m, 2H), 2.07 (s, 3H), 2.10–2.25 (m, 1H), 2.73 (t, J=7.3 Hz, 2H), 2.95 (s, 2H), 3.05–3.25 (m, 1H), 3.53–3.68 (m, 2H) ppm IR (KBr): 3328, 2976, 2936, 1590, 1520 cm$^{-1}$ Mass (m/z, %): 307 (M+, 100), 290 (75), 264 (32), 262 (25)

REFERENCE EXAMPLE 19

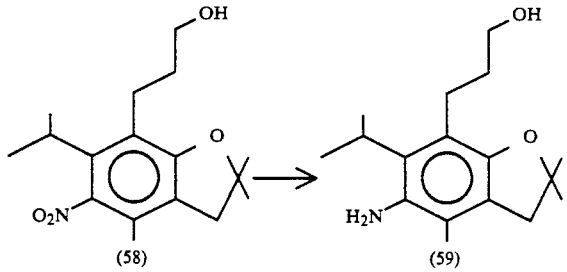

2.41 g (7.85 mmol) of the Compound No. 58 synthesized in Reference Example 18 and 630 mg of a 10% Pd/C were added to a mixed solvent containing 36.0 ml of methanol and 18.0 ml of water, followed by stirring in an atmosphere of argon gas, while cooled with water. To the thus obtained mixture, 640 mg (16.9 mmol) of sodium borohydride was added over a period of 20 minutes by four installments, followed by stirring for 30 minutes. After the addition of ethyl acetate, the reaction mixture was filtered through a Celite. After the thus obtained filtrate was transferred into a separatory funnel, the pH of an aqueous layer was made acid with the addition of 1N hydrochloric acid. An aqueous solution of sodium hydrogencarbonate was added to the aqueous layer until the pH range thereof was adjusted to 8–9, and then an organic layer was separated. The thus obtained organic layer was washed with a saturated aqueous solution of sodium chloride twice, dried over magnesium sulfate and concentrated. The concentrated material was chromatographed on a silica gel column and eluted with a mixed solvent of hexane and ethyl acetate at a ratio of 4:1, whereby 2.00 g of 3-[5-amino-2,3-dihydro-2,2,4-trimethyl-6-(propan-2-yl)benzo[b]furan-7-yl]propanol (Compound No. 59) was obtained in a yield of 92.0%.

Melting Point (°C.): 67.5–68.0 (colorless columns, recrystallized from hexane and ethyl acetate)

$^1$HNMR (300 MHz, CDCl$_3$): δ 1.38 (d, J=7.3 Hz, 6H), 1.46 (s, 6H), 1.66–1.80 (m, 2H), 2.04 (s, 3H), 2.72 (t, J=6.6 Hz, 2H), 2.96 (s, 2H), 3.08–3.28 (m, 1H), 3.30–3.55 (m, 4H) ppm IR (KBr): 3508, 3424, 3332, 2972, 2936, 1632 cm$^{-1}$ Mass (m/z, %): 277 (M+, 100), 232 (9), 218 (16)

REFERENCE EXAMPLE 20

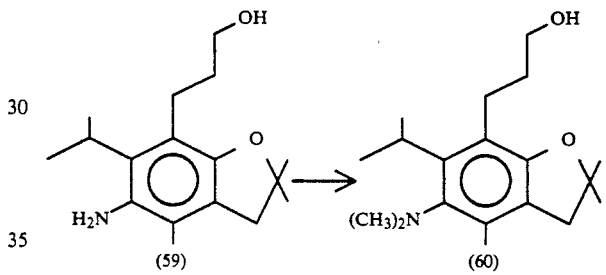

546 mg (1.97 mmol) of the Compound No. 59 synthesized in Reference Example 19, 600 mg (4.34 mmol) of potassium carbonate and 0.40 ml (6.43 mmol) of methyl iodide were added to 6.0 ml of DMF, followed by stirring in an atmosphere of argon gas at room temperature for 3 hours.

The above obtained reaction mixture was poured into water and extracted with ethyl acetate. The thus obtained extract layer was washed with a saturated aqueous solution of sodium chloride twice, dried over magnesium sulfate and concentrated. The concentrated material was chromatographed on a silica gel column and eluted with a mixed solvent of hexane and ethyl acetate at a ratio of 4:1, whereby 530 mg of 3-[2,3-dihydro-2,2,4-trimethyl-5-dimethylamino-6-(propan-2-yl)benzo[b]furan-7-yl]propanol (Compound No. 60) was obtained in a yield of 88.2%.

Melting Point (°C.): 79.5–81.0 (colorless columns, recrystallized from hexane and ethyl acetate)

$^1$HNMR (300 MHz, CDCl$_3$): δ 1.31 (d, J=7.1 Hz, 6H), 1.47 (s, 6H), 1.66–1.84 (m, 2H), 2.12 (s, 3H), 2.70 (t, J=6.8 Hz, 2H), 2.76 (s, 6H), 2.90 (s, 2H), 3.04–3.36 (m, 1H), 3.42–3.64 (m, 2H) ppm IR (KBr): 3372, 2968, 2924, 2876, 1590 cm$^{-1}$ Mass (m/z, %): 305(M+, 100), 290 (33), 275 (25), 262 (30), 261 (32)

REFERENCE EXAMPLE 21

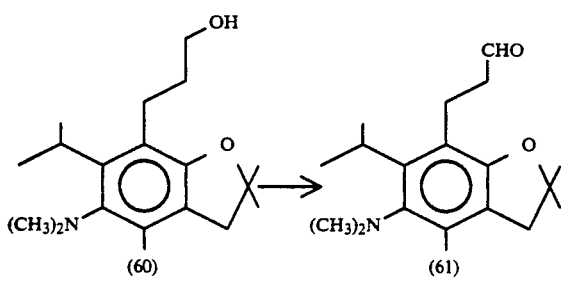

500 mg (1.64 mmol) of the Compound No. 60 synthesized in Reference Example 20 was added to 6.0 ml of dimethyl sulfoxide, followed by stirring in an atmosphere of argon gas at room temperature. To this mixture, 0.95 ml (6.82 mmol) of triethylamine, 2.0 ml of anhydrous THF and 930 mg (5.84 mmol) of sulfur trioxide pyridine complex were successively added, and the thus obtained mixture was stirred for 20 minutes.

The above reaction mixture was poured into diluted hydrochloric acid and extracted with hexane. The thus obtained extract layer was washed with a saturated aqueous solution of sodium chloride three times, dried over magnesium sulfate and concentrated. The concentrated material was chromatographed on a silica gel column and eluted with a mixed solvent of hexane and ethyl acetate at a ratio of 10:1, whereby 415 mg of 3-[2,3-dihydro-2,2,4-trimethyl-5-dimethylamino-6-(propan-2-yl)benzo[b]furan-7-yl]propanal (Compound No. 61) was obtained as a colorless amorphous solid in a yield of 83.5%.

1HNMR (300 MHz, CDCl3): δ 1.31 (d, J=7.2 Hz, 6H), 1.43 (s, 6H), 2.11 (s 3H), 2.59-2.73 (m, 2H), 2.77 (s, 6H), 2.87 (s, 2H), 2.89-2.99 (m, 2H), 3.25-3.65 (m, 1H), 9.84 (broad s, 1H) ppm IR (KBr): 2968, 2908, 1724, 1590 cm$^{-1}$ Mass (m/z, %): 303 (M$^+$, 100), 274 (29), 260 (26)

REFERENCE EXAMPLE 22

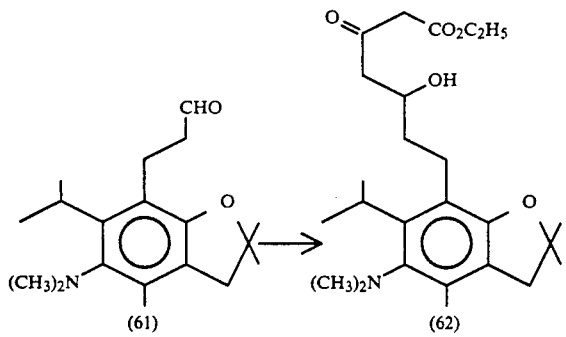

92 mg (2.30 mmol) of a 60% sodium hydride was suspended in 3.0 ml of anhydrous THF. To this suspension, 0.29 ml (2.28 mmol) of ethyl acetoacetate was added in an atmosphere of argon gas at 0° C., followed by stirring for 20 minutes. After the addition of 1.45 ml (2.27 mmol) of a 15% hexane solution of butyl lithium, the thus obtained mixture was stirred for 25 minutes and cooled to −78° C. 381 mg (1.26 mmol) of a the Compound No. 61 synthesized in Reference Example 21 was dissolved in 3.0 ml of anhydrous THF. This solution was added to the above mixture over a period of 10 minutes, followed by stirring for 35 minutes. After the completion of the reaction, the reaction mixture was poured into a saturated aqueous solution of sodium chloride and extracted with ethyl acetate. The thus obtained extract layer was washed with a saturated aqueous solution of sodium chloride three times, dried over magnesium sulfate and concentrated. The concentrated material was chromatographed on a silica gel column and eluted with a mixed solvent of hexane and ethyl acetate at a ratio of 5:1, whereby 412 mg of ethyl 7-[2,3-dihydro-2,2,4-trimethyl-5-dimethylamino-6-(propan-2-yl)benzo[b]furan-7-yl]-5-hydroxy-3-oxoheptanoate (Compound No. 62) was obtained as a colorless oily material in a yield of 75.7%.

1HNMR (300 MHz, CDCl3): δ 1.26 (t, J=7.2 Hz, 3H), 1.32 (broad d, J=6.9 Hz, 6H), 1.46 (s, 6H), 1.56-1.76 (m, 2H), 2.11 (s, 3H), 2.50-2.84 (m, 11H), 2.89 (s, 2H), 3.50 (s, 2H), 3.84-4.05 (m, 1H), 4.18 (q, J=7.2 Hz, 2H) ppm IR (liquid film): 3536, 2972, 2928, 1748, 1718, 1648 cm$^{-1}$ Mass (m/z, %): 433 (M$^+$, 100), 387 (20)

EXAMPLE 34

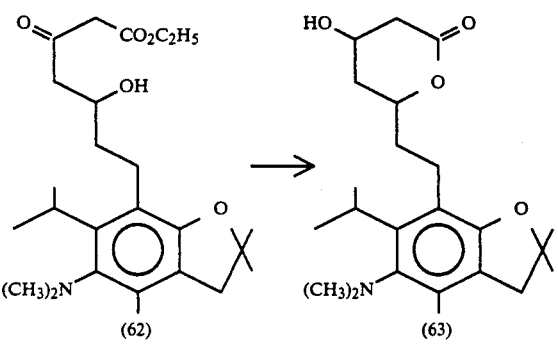

5 mg (0.05 mmol) of pivalic acid was added to 1.35 ml (1.35 mmol) of a 1.0M THF solution of triethylborane in an atmosphere of argon gas at room temperature, followed by stirring for 1 hour and 30 minutes. 396 mg (0.91 mmol) of the Compound No. 62 synthesized in Reference Example 22 was dissolved in 4.0 ml of anhydrous THF. This solution was added to the above mixture, stirred for 1 hour and 10 minutes and cooled to −78° C. 1.0 ml of methanol and 43 mg (1.14 mmol) of sodium borohydride were successively added to the above mixture. The reaction mixture was further stirred for 1 hour, gradually added to 6.0 g of a 30% aqueous hydrogen peroxide at 0° C., and stirred for 3 hours.

The above reaction mixture was poured into water and extracted with ethyl acetate. The thus obtained extract layer was washed successively with a saturated aqueous solution of sodium chloride, an aqueous solution of sodium thiosulfate and a saturated aqueous solution of sodium chloride three times, dried over magnesium sulfate, and concentrated. Then, 3.0 ml of methanol was added to the concentrated material, followed by stirring in an atmosphere of argon gas at room temperature. After the addition of 0.40 ml (2.00 mmol) of 5N sodium hydroxide, the thus obtained mixture was stirred for 25 minutes, and poured into diluted hydrochloric acid. Subsequently, an aqueous solution of sodium hydrogencarbonate was added to the above reaction mixture until the pH range thereof was adjusted to 4-5. This reaction mixture was extracted with ethyl acetate. The thus obtained extract layer was washed with a saturated aqueous solution of sodium chloride twice, dried over magnesium sulfate and concentrated. The concentrated material was dissolved in 5.0 ml of anhydrous toluene and refluxed in an atmosphere of argon gas for 6 hours. The reaction mixture was concentrated, chromatographed on a silica gel column, and eluted with a mixed solvent of hexane and ethyl acetate at a ratio of 1:1, whereby 230 mg of trans-(±)-6-[2,3-dihydro-2,2,4-trimethyl-5-dimethylamino-6-(propan-2-yl)benzo[b]furan-7-yl]ethyl-4-hydroxytetrahydropyran-2-one (Compound No. 63) was obtained in a yield of Melting Point (°C.): 136.0–137.5 (colorless fine particles, recrystallized from hexane and ethyl acetate)

$^1$HNMR (300 MHz, CDCl$_3$): δ 1.32 (d, J=7.2 Hz, 3H), 1.33 (d, J=7.2 Hz, 3H), 1.43 (s, 3H), 1.44 (s, 3H), 1.70–2.15 (m, 4H), 2.11 (s, 3H), 2.57–2.90 (m, 4H), 2.77 (s, 6H), 2.87 (s, 2H), 3.20–3.80 (m, 1H), 4.35–4.46 (m, 1H), 4.67–4.84 (m, 1H) ppm IR (KBr): 3463, 2968, 2932, 1714, 1590 cm$^{-1}$ Mass (m/z, %): 389 (M+, 100), 371 (26)

REFERENCE EXAMPLE 23

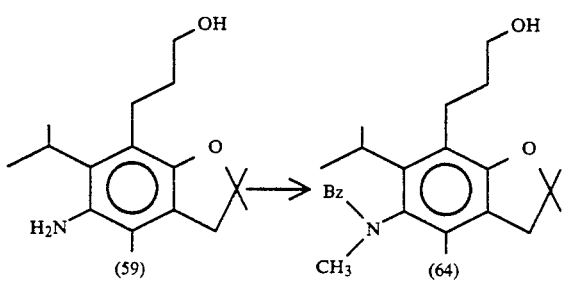

1.16 g (4.19 mmol) of the Compound No. 59 synthesized in Reference Example 19 and 0.60 ml (5.90 mmol) of benzaldehyde were added to 10.0 ml of ethanol. The thus obtained mixture was then stirred in an atmosphere of argon gas at room temperature for 35 minutes. After the addition of 0.10 ml (0.984 mol) of benzaldehyde, the reaction mixture was further stirred for 1 hour. After the addition of 350 mg (9.25 mmol) of sodium borohydride and 1.0 ml of methanol, the reaction mixture was stirred for 2 hours and 30 minutes and poured into 1N hydrochloric acid. Subsequently, an aqueous solution of sodium hydrogencarbonate was added to the reaction mixture until the pH range thereof was adjusted to 8–9, and the above reaction mixture was then extracted with ethyl acetate. The thus obtained extract layer was washed with a saturated aqueous solution of sodium chloride twice, dried over magnesium sulfate and concentrated. The concentrated material was chromatographed on a silica gel column, and eluted with a mixed solvent of hexane and methylene chloride at the ratio of 5:1, whereby 1.47 g of 3-[5-benzylamino-2,3-dihydro-2,2,4-trimethyl-6-(propan-2-yl) benzo[b]furan-7-yl]propanol was obtained in a yield of 95.8%.

674 mg (1.84 mmol) of 3-[5-benzylamino-2,3-dihydro-2,2,4-trimethyl-6-(propan-2-yl)benzo(b]furan-7-yl]propanol, 522 mg (3.78 mmol) of potassium carbonate and 0.35 ml (5.62 mmol) of methyl iodide were added to 5.0 ml of DMF, followed by stirring in an atmosphere of argon gas at room temperature for 11 hours and 30 minutes. After the addition of 0.35 ml (5.62 mmol) of methyl iodide, the reaction mixture was further stirred for 19 hours and 30 minutes, poured into a saturated aqueous solution of sodium chloride and extracted with ethyl acetate. The thus obtained extract layer was washed with a saturated aqueous solution of sodium chloride three times, dried over magnesium sulfate and concentrated. The concentrated material was chromatographed on a silica gel column and eluted with a mixed solvent of hexane and ethyl acetate at a ratio of 2:1, whereby 477 mg of 3-[5-(N-benzyl-N-methylamino)-2,3-dihydro-2,2,4-trimethyl-6-(propan-2-yl)benzo[b]furan-7-yl]propanol (Compound No. 64) was obtained as a colorless oily material in a yield of 68.2%.

$^1$HNMR (300 MHz, CDCl$_3$): δ 1.33 (d, J=7.3 Hz, 3H), 1.30–1.48 (m, 3H), 1.48 (s, 6H), 1.74–1.92 (m, 2H), 2.20 (s, 3H), 2.66 (s, 3H), 2.76 (t, J=7.4 Hz, 2H), 2.92 (s, 2H), 3.54–3.76 (m, 2H), 3.82–4.34 (m, 3H), 7.22–7.46 (m, 5H) ppm

REFERENCE EXAMPLE 24

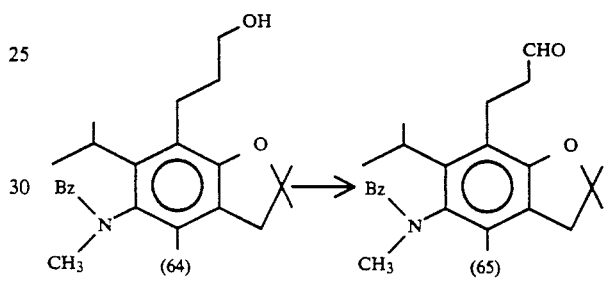

472 mg (1.24 mmol) of the Compound No. 64 synthesized in Reference Example 23 was added to 6.0 ml of dimethyl sulfoxide, followed by stirring in an atmosphere of argon gas at room temperature. To the thus obtained mixture, 0.60 ml (4.30 mmol) of triethylamine, 2.0 ml of anhydrous THF and 595 mg (3.74 mmol) of sulfur trioxide pyridine complex were successively added. The above mixture was then stirred for 30 minutes, poured into diluted hydrochloric acid, and extracted with ethyl acetate. The thus obtained extract layer was washed with a saturated aqueous solution of sodium chloride, dried over magnesium sulfate and concentrated. The concentrated material was chromatographed on a silica gel column and eluted with a mixed solvent of hexane and ethyl acetate at a ratio of 15:1, whereby 378 mg of 3-[2,3-dihydro-5-(N-benzyl-N-methylamino)-2,2,4-trimethyl-6-(propan-2-yl)benzo[b]furan-7-yl]propanal (Compound No. 65) was obtained as a colorless amorphous solid in a yield of 80.3%.

$^1$HNMR (300 MHz, CDCl$_3$): δ 1.31 (d, J=7.3 Hz, 3H), 1.32 (broad d, J=7.3 Hz, 3H), 1.45 (s, 6H), 2.20 (s, 3H), 2.65 (s, 3H), 2.68–2.80 (m, 2H), 2.90 (s, 2H), 2.94–3.04 (m, 2H), 3.86–4.26 (m, 3H), 7.21–7.41 (m, 5H), 9.88 (broad s, 1H) ppm IR (KBr): 2968, 2932, 1722, 1588 cm$^{-1}$ Mass (m/z, %): 379 (M+, 100), 288 (95), 273 (59), 91 (28)

REFERENCE EXAMPLE 25

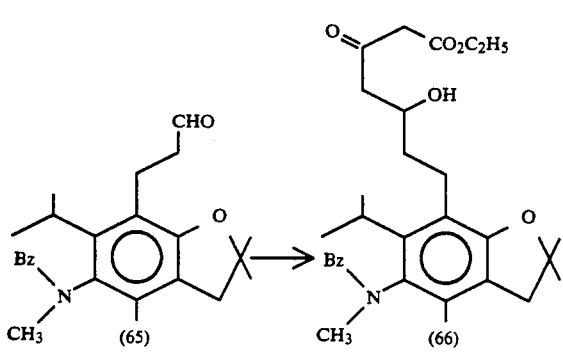

58 mg (1.45 mmol) of a 60% sodium hydride was suspended in 2.5 ml of anhydrous THF. To the thus obtained suspension, 0.185 ml (1.45 mmol) of ethyl acetoacetate was added in a stream of argon gas at room temperature. The above mixture was then stirred for 20 minutes and cooled to 0° C. After the addition of 0.93 ml (1.45 mmol) of a 15% hexane solution of butyl lithium, the above mixture was stirred for 20 minutes. The above reaction mixture was further cooled to −78° C., and 369 mg (0.97 mmol) of a solution of the Compound No. 65 synthesized in Reference Example 24 in 4.0 ml of anhydrous THF was added thereto over a period of 10 minutes, followed by stirring for 1 hour.

The thus obtained reaction mixture was poured into a saturated aqueous solution of sodium chloride and extracted with ethyl acetate. The thus obtained extract layer was washed with a saturated aqueous solution of sodium chloride three times, dried over magnesium sulfate and concentrated. The concentrated material was chromatographed on a silica gel column, and eluted with a mixed solvent of hexane and ethyl acetate at a ratio of 5:1, whereby 395 mg of ethyl 7-[2,3-dihydro-5-(N-benzyl-N-methylamino)-2,2,4-trimethyl6-(propan-2-yl)benzo[b]furan-7-yl]-5-hydroxy-3-oxoheptanoate was obtained as a colorless oily material in a yield of $^1$HNMR (300 MHz, CDCl$_3$): δ 1.20–1.43 (m, 9H), 1.47 (s, 6H), 1.65–1.80 (m, 2H), 2.20 (s, 3H), 2.75–2.96 (m, 4H), 2.66 (s, 3H), 2.91 (s, 2H), 3.15–3.38 (m, 1H), 3.51 (s, 2H), 3.85–4.30 (m, 3H), 4.19 (q, J=7.2 Hz, 2H), 7.20–7.45 (m, 5H) ppm IR (liquid film): 3492, 2972, 2932, 1746, 1714, 1650 cm$^{-1}$ Mass (m/z, %): 509 (M$^+$, 85), 418 (28), 379 (45), 288 (68), 273 (61), 245 (28), 244 (75), 230 (34), 229 (39), 228 (36), 214 (35), 91 (100)

EXAMPLE 35

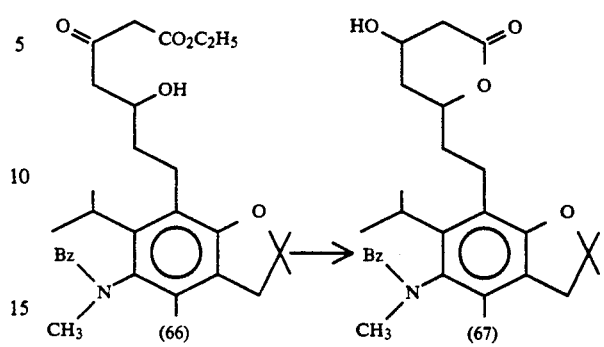

5 mg (0.049 mmol) of pivalic acid was added to 1.10 ml (1.10 mmol) of a 1.0M THF solution of triethylborane in an atmosphere of argon gas at room temperature, followed by stirring for 1 hour and 20 minutes. After the addition of 380 mg (0.747 mmol) of a solution of the Compound No. 66 synthesized in Reference Example 25 in 5.0 ml of anhydrous THF, the reaction mixture was stirred for 1 hour and 30 minutes, and cooled to −78° C. 0.8 ml of methanol and 32 mg (0.846 mmol) of sodium borohydride were successively added to the reaction mixture. The reaction mixture was stirred for 1 hour, gradually added to a solution of 5.0 g of a 30% aqueous hydrogen peroxide at 0° C., and further stirred for 2 hours and 30 minutes.

The above reaction mixture was poured into water and extracted with ethyl acetate. The thus obtained extract layer was washed successively with a saturated aqueous solution of sodium chloride, an aqueous solution of sodium thiosulfate and a saturated aqueous solution of sodium chloride three times, dried over magnesium sulfate, and concentrated. After the addition of 5.0 ml of methanol, the thus obtained mixture was stirred in an atmosphere of argon gas at room temperature. After the addition of 0.30 ml (1.50 mmol) of 5N sodium hydroxide, the reaction mixture was then stirred for 30 minutes and poured into diluted hydrochloric acid. Subsequently, an aqueous solution of sodium hydrogencarbonate was added to the above mixture until the pH range thereof was adjusted to 4–5, and the above mixture was extracted with ethyl acetate. The thus obtained extract layer was washed with a saturated aqueous solution of sodium chloride twice, dried over magnesium sulfate and concentrated. The thus obtained concentrated material was dissolved in 6.0 ml of anhydrous toluene and refluxed in an atmosphere of argon gas for 6 hours. The thus obtained reaction mixture was further concentrated, chromatographed on a silica gel column and eluted with a mixed solvent of hexane and ethyl acetate at the ratio of 1:1, whereby 266 mg of trans-(±)-6-[5-(N-benzyl-N-methylamino)-2,3-dihydro-2,2,4-trimethyl-6-(propan-2-yl)benzo[b]furan-7-yl]ethyl-4-hydroxytetrahydropyran-2-one (Compound No. 67) was obtained as an colorless amorphous solid in a yield of 76.6%.

$^1$HNMR (300 MHz, CDCl$_3$): δ 1.30–1.40 (m, 6H), 1.45 (s, 6H), 1.78–2.12 (m, 4H), 2.19 (s, 3H), 2.57–3.02 (m, 3H), 2.65 (s, 3H), 2.79 (dd, J=17.5 and 5.1 Hz, 1H), 2.90 (s, 2H), 3.83–4.25 (m, 3H), 4.38–4.47 (m, 1H), 4.74–4.87 (m, 1H), 7.22–7.42 (m, 5H) ppm IR (KBr): 3462, 2968, 2928, 1714, 1589 cm$^{-1}$ Mass (m/z, %): 465 (M+, 54), 374 (41), 244 (64), 230 (27), 229 (43), 228 (32), 214 (30), 91 (100)

REFERENCE EXAMPLE 26

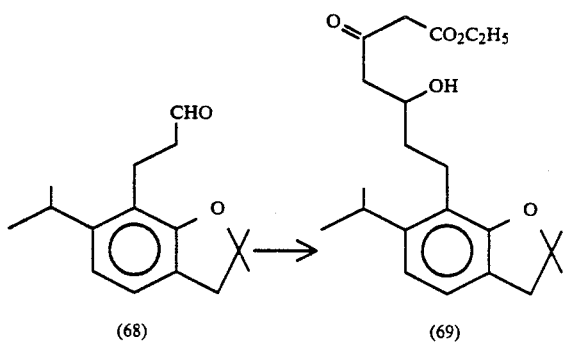

952 mg (23.8 mmol) of a 60% sodium hydride was suspended in 25 ml of anhydrous THF. After the addition of 3.03 ml (23.8 mmol) of ethyl acetoacetate in a stream of argon gas at 0° C., the thus obtained mixture was stirred for 30 minutes. After the addition of 15.2 ml (23.8 mmol) of a 15% hexane solution of butyl lithium, the reaction mixture was further stirred for 30 minutes, and cooled to −78° C. To the above mixture, a solution of 4.55 g (18.5 mmol) of 3-[2,3-dihydro-2,2-dimethyl-6-(propan-2-yl)benzo[b]furan-7-yl]propanol (Compound No. 68) synthesized by use of 2-(2-methyl-2-propen-1-yl)-5-(propan-2-yl)phenol as a material in accordance with the methods in Reference Examples 1 to 3 in 15 ml of anhydrous THF was added. After 1 hour and 55 minutes, the above reaction mixture was poured into water, and extracted with ethyl acetate. The thus obtained extract layer was washed successively with water, a saturated aqueous solution of ammonium chloride and a saturated aqueous solution of sodium chloride, dried over magnesium sulfate, and then concentrated. The concentrated material was chromatographed on a silica gel column, and eluted with a mixed solvent of ethyl acetate and hexane at a ratio of 1:3, whereby 4.50 g of ethyl 7-[2,3-dihydro-2,2-dimethyl-6-(propan-2-yl)benzo[b]furan-7-yl]-5-hydroxy-3-oxoheptanoate (Compound No. 69) was obtained as a colorless oily material in a yield of 64.7%.

$^1$HNMR (300 MHz, CDCl$_3$): δ 1.19 (d, J=6.8 Hz, 3H), 1.22 (d, J=6.8 Hz, 3H), 1.26 (t, J=7.2 Hz, 3H), 1.47 (s, 3H), 1.47 (s, 3H), 1.54–1.78 (m, 2H), 2.58 (dd, J=16.3 and 3.3 Hz, 1H), 2.66–2.84 (m, 3H), 2.99 (s, 2H), 3.09 (hept, J=6.8 Hz, 1H), 3.49 (s, 2H), 3.59 (d, J=3.7 Hz, 1H), 3.89–4.00 (m, 1H), 4.17 (q, J=7.2 Hz, 2H), 6.78 (d, J=7.8 Hz, 1H), 6.98 (d, J=7.8 Hz, 1H) ppm IR (liquid film): 3524, 2972, 1740, 1714 cm$^{-1}$ Mass (m/z, %): 376 (M+, 49), 358 (14), 330 (10), 246 (20), 203 (100), 189 (20), 159 (22), 43 (15)

EXAMPLE 36

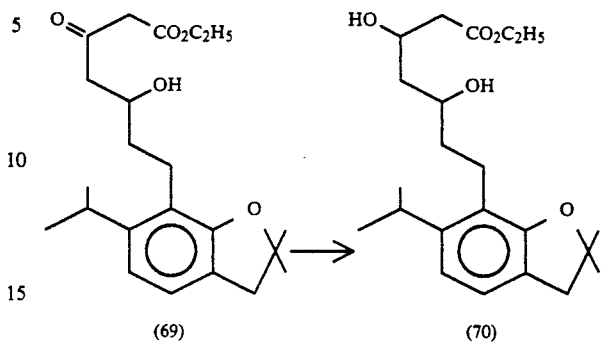

14.2 ml (14.2 mmol) of a 1.0M THF solution of triethylborane was added to 50 mg (0.49 mmol) of pivalic acid in a stream of argon gas, at room temperature followed by stirring for 1 hour. To the above mixture, a solution of 4.44 g (11.8 mmol) of the Compound No. 69 synthesized in Reference Example 26 in 50 ml of anhydrous THF was added. After 55 minutes, the above reaction mixture was cooled to −78° C. and 17.7 ml of methanol was added thereto. Subsequently, 669 mg (17.7 mmol) of sodium borohydride was gradually added to the above mixture over a period of 10 minutes. This reaction mixture was stirred for 45 minutes, poured into a solvent containing 50 ml of a 30% aqueous hydrogen peroxide and 100 ml of water at 0° C., and further stirred overnight at room temperature. The thus obtained reaction mixture was then poured into a saturated aqueous solution of ammonium chloride, and extracted with ethyl acetate. The thus obtained extract layer was washed successively with water, a saturated aqueous solution of sodium chloride, a saturated aqueous solution of sodium thiosulfate and a saturated aqueous solution of sodium chloride, dried over magnesium sulfate, and concentrated. The thus obtained concentrated material was chromatographed on a silica gel column, and eluted with a mixed solvent of ethyl acetate and hexane at a ratio of 1:2, whereby 3.91 g of ethyl 7-[2,3-dihydro-2,2-dimethyl-6-(propan-2-yl)benzo[b]furan-7-yl]-3,5-dihydroxyheptanoate (Compound No. 70) was obtained as a colorless oily material in a yield of 87.7%.

$^1$HNMR (300 MHz, CDCl$_3$): δ 1.19 (d, J=6.8 Hz, 3H), 1.22 (d, J=6.8 Hz, 3H), 1.24 (t, J=7.1 Hz, 3H), 1.48 (s, 3H), 1.49 (s, 3H), 1.50–1.65 (m, 3H), 1.65–1.80 (m, 1H), 2.38 (dd, J=15.5 and 5.4 Hz, 1H), 2.51 (dd, J=15.5 and 7.4 Hz, 1H), 2.63–2.87 (m, 2H), 3.02 (s with fine coupling, 1H), 3.09 (hept, J=6.8 Hz, 1H), 3.65–3.77 (m, 1H), 4.13 (q, J=7.1 Hz, 2H), 4.15–4.27 (m, 1H), 4.24 (s with fine coupling, 1H), 4.40 (s with fine coupling, 1H), 6.81 (d, J=7.8 Hz, 1H), 7.00 (d, J=7.8 Hz, 1H) ppm IR (KBr): 3456, 3044, 2976, 2872, 1730 cm$^{-1}$ Mass (m/z, %): 378 (M+, 100), 360 (49), 203 (88), 189 (35), 161 (32), 69 (18)

EXAMPLE 37

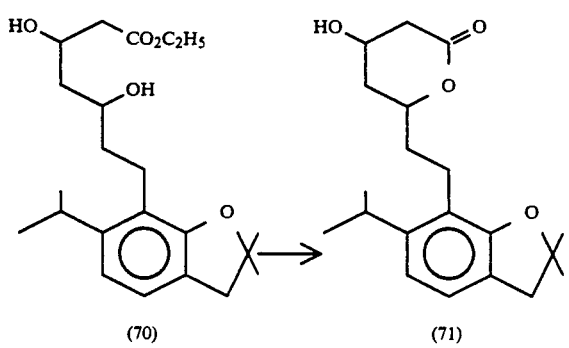

3.70 g (9.79 mmol) of the Compound No. 70 synthesized in Example 36 was dissolved in 20 ml of methanol. After the addition of 14.7 ml (14.7 mmol) of 1N sodium hydroxide at 0° C., the thus obtained mixture was stirred in an atmosphere of argon gas at room temperature for 40 minutes. This reaction mixture was poured into 1N hydrochloric acid, and extracted with ethyl acetate. The thus obtained extract layer was washed successively with water and a saturated aqueous solution of sodium chloride, dried over magnesium sulfate and concentrated. The thus obtained concentrated material was dissolved in 20 ml of ethyl acetate. 2.89 ml (37.5 mmol) of trifluoroacetic acid was added to the thus obtained mixture, followed by stirring overnight at room temperature. The reaction mixture was poured into a saturated aqueous solution of sodium hydrogencarbonate, and extracted with ethyl acetate. The thus obtained extract layer was washed successively with water and a saturated aqueous solution of sodium chloride, dried over magnesium sulfate, and concentrated. The thus obtained concentrated material was chromatographed on a silica gel column, and eluted with a mixed solvent of ethyl acetate and hexane at a ratio of 2:1, whereby 2.66 g of trans-($\pm$)-6-[2,3-dihydro-2,2-dimethyl-6-(propan-2-yl)benzo[b]furan-7-yl]ethyl-4-hydroxytetrahydropyran-2-one (compound No. 71) was obtained in a yield of 81.8%.

Melting Point (°C.): 82.5–84.0 (colorless fine particles, recrystallized from ethyl acetate and hexane)

$^1$HNMR (300 MHz, CDCl$_3$): $\delta$ 1.20 (d, J=6.8Hz, 3H), 1.21 (d, J=6.8 Hz, 3H), 1.44 (s, 3H), 1.44 (s, 3H), 1.73–2.08 (m, 5H), 2.62 (ddd, J=17.4, 4.0 and 1.5 Hz, 1H), 2.78 (dd, J=17.4 and 5.1 Hz, 1H), 2.67–2.88 (m, 2H), 2.96 (s, 2H), 3.12 (hept, J=6.8 Hz, 1H), 4.38–4.45 (m, 1H), 4.71–4.80 (m, 1H), 6.60 (d, J=7.8 Hz, 1H), 9.97 (d, J=7.8 Hz, 1H) ppm IR (KBr): 3416, 2968, 2928, 1732 cm$^{-1}$ Mass (m/z, %): 332 (M$^+$, 100), 314 (11), 203 (32), 187 (22), 159 (17), 145 (7), 129 (6), 43 (5)

EXAMPLE 38

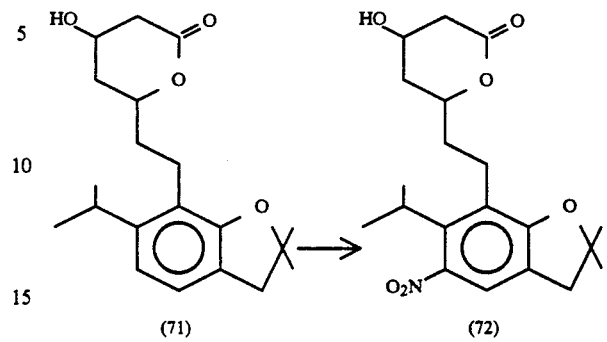

1.21 g (3.64 mmol) of the Compound No. 71 synthesized in Example 37 was dissolved in 20 ml of acetic acid. To this solution, 2.52 ml (5.04 mmol) of a 2M nitric acid in acetic acid and 13 mg (0.182 mmol) of sodium nitrite were successively added. The thus obtained mixture was stirred in an atmosphere of argon gas at room temperature for 3 hours and 40 minutes. The reaction mixture was poured into water, and extracted with ethyl acetate. The thus obtained extract layer was washed successively with a saturated aqueous solution of sodium hydrogencarbonate and a saturated aqueous solution of sodium chloride, dried over magnesium sulfate, and concentrated. The thus obtained concentrated material was chromatographed on a silica gel column, and eluted with a mixed solvent of ethyl acetate and hexane at a ratio of 2:1, whereby 1.17 g of trans-($\pm$)-6-[2,3-dihydro-2,2-dimethyl-5-nitro-6-(propan-2-yl)benzo[b]furan-7-yl]ethyl-4-hydroxytetrahydropyran-2-one (Compound No. 72) was obtained as a red amorphous solid in a yield of 85.3%.

$^1$HNMR (300 MHz, CDCl$_3$): $\delta$ 1.36 (d, J=7.2 Hz, 6H), 1.48 (s, 3H), 1.48 (s, 3H), 1.68–1.96 (m, 4H), 1.97–2.05 (m, 1H), 2.65 (ddd, J=17.6, 3.9 and 1.6 Hz, 1H), 2.50–2.81 (m, 1H), 2.78 (dd, J=17.6 and 4.9 Hz, 1H), 2.87–2.99 (m, 1H), 3.00 (s with fine coupling, 2H), 3.31 (hept, J=7.2 Hz, 1H), 4.39–4.47 (m, 1H), 4.72–4.83 (m, 1H), 7.26 (s, 1H) ppm IR (KBr): 3486, 2970, 2936, 1735, 1518 cm$^{-1}$ Mass (m/z, %): 377 (M$^+$, 97), 360 (100), 347 (63), 230 (43), 214 (38), 212 (32), 202 (29), 200 (22), 188 (22), 129 (17), 43 (29)

EXAMPLE 39

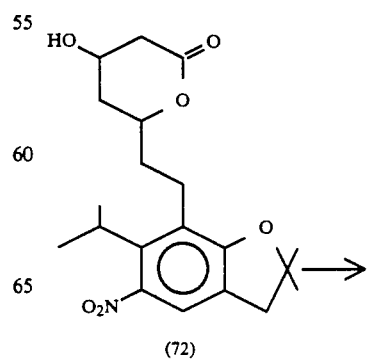

-continued

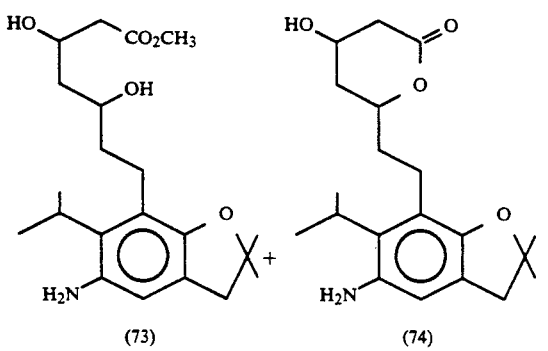

1.11 g (2.94 mmol) of the Compound No. 72 synthesized in Example 38 was dissolved in 10 ml of methanol. After the addition of 420 mg of platinum oxide, the thus obtained mixture was stirred in an atmosphere of hydrogen at room temperature for 3 hours and 50 minutes. The thus obtained reaction mixture was diluted with ethyl acetate, and filtered through a Celite. The filtrate was then concentrated, chromatographed on a silica gel column, and eluted with a mixed solvent of ethyl acetate and hexane at a ratio of 2:1, and then with ethyl acetate, whereby 772 mg of methyl 7-[5-amino-2,3-dihydro-2,2-dimethyl-6-(propan-2-yl)benzo[b]furan-7-yl]-3,5-dihydroxyheptanoate (Compound No. 73) was obtained in a yield of 75.7%. Subsequently, 108 mg of trans-(±)-6-[5-amino-2,3-dihydro-2,2-dimethyl-6-(propan-2-yl)benzo[b]furan-7-yl]ethyl-4-hydroxytetrahydropyran-2-one (Compound No. 74) was obtained as a yellow oily material in a yield of 11.7%.

(Compound No. 73)

Melting Point (°C.): 94.0–96.0 (colorless particles, recrystallized from ethyl acetate and hexane)

$^1$HNMR (300 MHz, CDCl$_3$): δ 1.35 (d, J=7.3 Hz, 3H), 1.37 (d, J=7.3 Hz, 3H), 1.45 (s, 3H), 1.46 (s, 3H), 1.50–1.62 (m, 3H), 1.64–1.77 (m, 1H), 2.38 (dd, J=15.4 and 5.6 Hz, 1H), 2.52 (dd, J=15.4 and 7.3 Hz, 1H), 2.58–2.70 (m, 1H), 2.75–2.86 (m, 1H), 2.95 (s, 2H), 3.32 (hept, J=7.3 Hz, 1H), 3.43 (broad s, 2H), 3.67 (s, 3H), 3.60–3.71 (m, 1H), 4.15–4.26 (m, 1H), 4.44 (broad s, 1H), 4.53 (broad s, 1H), 6.40 (s, 1H) ppm IR (KBr): 3496, 3416, 2960, 2928, 1736, 1630 cm$^{-1}$ Mass (m/z, %): 379 (M$^+$, 100), 361 (31), 347 (17), 329 (23), 218 (28), 202 (42), 176 (16), 149 (11), 44 (11)

(Compound No. 74)

$^1$HNMR (300 MHz, CDCl$_3$): δ 1.36 (d, J=7.2 Hz, 3H), 1.37 (d, J=7.2 Hz, 3H), 1.40 (s, 3H), 1.41 (s, 3H), 1.70–2.07 (m, 5H), 2.62 (ddd, J=17.5, 4.0 and 1.4 Hz, 1H), 2.77 (dd, J=17.5 and 5.1 Hz, 1H), 2.67–2.82 (m, 2H), 2.90 (s, 2H), 3.29–3.42 (m, 3H), 4.36–4.45 (m, 1H), 4.68–4.80 (m, 1H), 6.39 (s, 1H) ppm IR (KBr): 3476, 2976, 1742, 1632 cm$^{-1}$ Mass (m/z, %): 347 (M$^+$, 100), 329 (17), 218 (13), 202 (24), 174 (6), 160 (4), 43 (4)

EXAMPLE 40

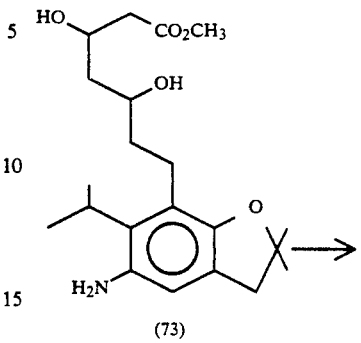

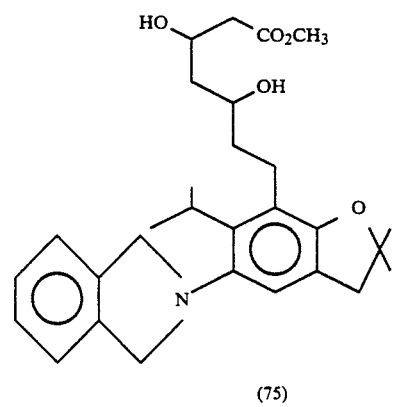

620 mg (2.35 mmol) of α,α'-dibromo-o-xylene and 778 mg (5.64 mmol) of potassium carbonate were added to 10 ml of anhydrous DMF, and then stirred. To the thus obtained mixture, a solution of 712 mg (1.88 mmol) of the Compound No. 73 synthesized in Example 39 in 5 ml of anhydrous DMF was added dropwise in an atmosphere of argon gas at room temperature over a period of 40 minutes.

The above mixture was further stirred for 1 hour and 10 minutes, poured into water and extracted with ethyl acetate. The thus obtained extract layer was washed with a saturated aqueous solution of sodium chloride, dried over magnesium sulfate and concentrated. The thus obtained concentrated material was chromatographed on a silica gel column, and eluted with a mixed solvent of ethyl acetate and hexane at a ratio of 2:1, whereby 730 mg of methyl 7-[2,3-dihydro-5-(isoindolin-2-yl)-2,2-dimethyl-6-(propan-2-yl)benzo[b]furan-7-yl]-3,5-dihydroxyheptanoate (Compound No. 75) was obtained in a yield of 80.7%.

Melting Point (°C.): 182.0–183.5 (colorless fine particles, recrystallized from ethyl acetate and hexane)

$^1$HNMR (300 MHz, CDCl$_3$): δ 1.38 (d, J=7.0 Hz, 6H), 1.48 (s, 3H), 1.49 (s, 3H), 1.51–1.65 (m, 3H), 1.67–1.80 (m, 1H), 2.42 (dd, J=15.6 and 5.4 Hz, 1H), 2.54 (dd, J=15.6 and 7.6 Hz, 1H), 2.64–2.88 (m, 2H), 2.98 (s, 2H), 3.69 (s, 3H), 3.69–3.80 (m, 1H), 4.18–4.32 (m, 2H), 4.42 (s, 4H), 4.46 (broad s, 1H), 7.11 (s, 1H), 7.20–7.30 (m, 4H) ppm IR (KBr): 3490, 2954, 2820, 2794, 1717 cm$^{-1}$ Mass (m/z, %): 481 (M$^+$, 100), 449 (22), 321 (23), 304 (22), 278 (14), 214 (8), 118 (16)

EXAMPLE 41

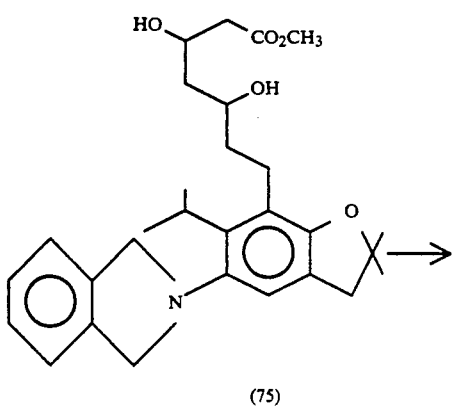

(75)

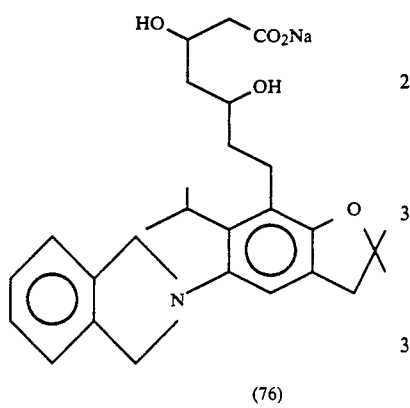

(76)

415 mg (0.987 mmol) of the Compound No. 75 synthesized in Example 40 was dissolved in 8 ml of ethanol. After the addition of 0.987 ml (0.987 mmol) of 1N sodium hydroxide, the thus obtained mixture was stirred in an atmosphere of argon gas at room temperature for 55 minutes. The reaction mixture was concentrated, dissolved in water, and lyophilized, whereby 473 mg of sodium 7-[2,3-dihydro-5-(isoindolin-2-yl)-2,2-dimethyl-6-(propan-2-yl)benzo[b]furan-7-yl]-3,5-dihydroxyheptanoate (Compound No. 76) was obtained as a colorless amorphous solid in a yield of 98.0%.

$^1$HNMR (300 MHz, CD$_3$OD): δ 1.38 (d, J=7.1 Hz, 6H), 1.44 (s, 6H), 1.59–1.74 (m, 4H), 2.29 (dd, J=15.2 and 7.6 Hz, 1H), 2.40 (dd, J=15.2 and 5.0 Hz, 1H), 2.58–2.70 (m, 1H), 2.73–2.85 (m, 1H), 2.94 (s with fine coupling, 2H), 3.80–3.90 (m, 1H), 4.11–4.20 (m, 1H), 4.35 (s, 4H), 7.09 (s, 1H), 7.22 (s, 4H) ppm IR (KBr): 3424, 2928, 1572 cm$^{-1}$ Mass (FAB-neg, m/z, %): 488 ([M-H]$^-$, 33), 466 (100), 384 (13), 362 (14), 332 (7), 318 (6), 116 (23), 85 (18)

EXAMPLE 42

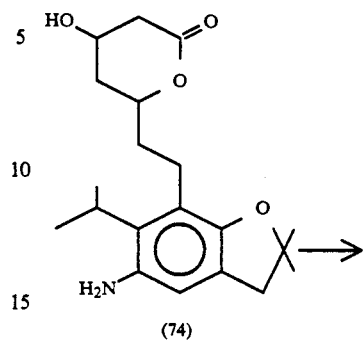

(74)

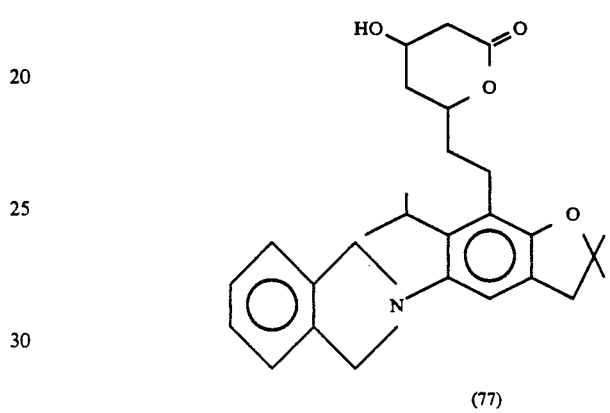

(77)

3.39 g (12.8 mmol) of α-α'-dibromo-o-xylene and 4.08 g (29.6 mmol) of potassium carbonate were added to 10 ml of anhydrous DMF and then stirred. To this mixture, a solution of 3.42 g (9.86 mmol) of the Compound No. 74 synthesized in Example 39 in 15 ml of anhydrous DMF was added dropwise over a period of 2 hours. The thus obtained reaction mixture was further stirred for 55 minutes, poured into water, and extracted with ethyl acetate. The thus obtained extract layer was washed with a saturated aqueous solution of sodium chloride, dried over magnesium sulfate, and concentrated, whereby 3.13 g of crystals of trans-(±)-6-[2,3-dihydro-5-(isoindolin-2-yl)-2,2-dimethyl-6-(propan-2-yl)benzo[b]furan-7-yl]ethyl-4-hydroxytetrahydropyran-2-one (Compound No. 77) was obtained in a yield of 70.8%. The filtrate was concentrated, chromatographed on a silica gel column, and eluted with a mixed solvent of ethyl acetate and hexane at a ratio of 2:1, whereby 615 mg of the Compound No. 77 was further obtained in a yield of 13.9%.

Melting Point (°C.): 197.0–198.0 (colorless fine particles, recrystallized from ethyl acetate and hexane, partially decomposed near 191° C.)

$^1$HNMR (300 MHz, CDCl$_3$): δ 1.37 (d, J=7.1 Hz, 3H), 1.38 (d, J=7.1 Hz, 3H), 1.44 (s, 3H), 1.45 (s, 3H), 1.72–1.99 (m, 4H), 2.00–2.11 (m, 1H), 2.64 (ddd, J=17.3, 4.0 and 1.4 Hz, 1H), 2.79 (dd, J=17.3 and 5.2 Hz, 1H), 2.68–2.90 (m, 2H), 2.94 (s, 2H), 4.41 (s, 4H), 4.40–4.48 (m, 1H), 4.72–4.82 (m, 1H), 7.09 (s, 1H), 7.25 (s, 4H) ppm IR (KBr): 3548, 2980, 2956, 2896, 2780, 1746 cm$^{-1}$ Mass (m/z, %): 449 (M$^+$, 100), 431 (81), 319 (28), 304 (26), 302 (35), 214(8), 118 (18)

EXAMPLE 43

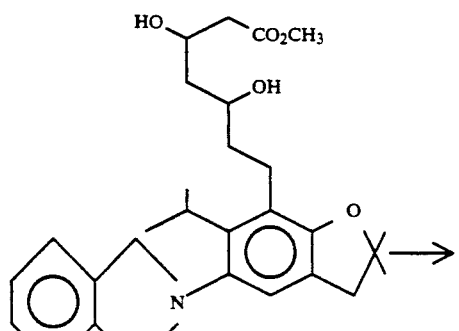

(75)

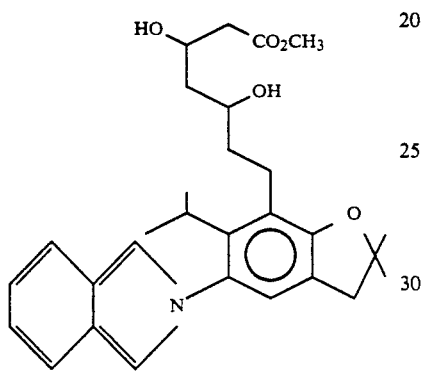

(78)

125 mg (0.260 mmol) of the Compound No. 75 synthesized in Example 40 was dissolved in 3 ml of anhydrous DMF. After the addition of 29 mg of salcomine (34% w/w), the thus obtained mixture was stirred in an atmosphere of oxygen overnight at room temperature. Furthermore, with the addition of 25 mg of salcomine (29% w/w), the reaction mixture was stirred for 3 days, diluted with water and ethyl acetate, and filtered through a Celite.

The thus obtained ethyl acetate layer was washed successively with water and a saturated aqueous solution of sodium chloride, dried over magnesium sulfate and concentrated. The thus obtained concentrated material was chromatographed on a silica gel column, and eluted with a mixed solvent of ethyl acetate and hexane at a ratio of 1:1, whereby 16 mg of methyl 7-[2,3-dihydro-5-isoindolyl-2,2-dimethyl-6-(propan-2-yl)benzo[b]furan-7-yl]-3,5-dihydroxyheptanoate (Compound No. 78) was obtained in a yield of 12.8%. Furthermore, 78 mg of the Compound No. 77 was recovered in a yield of 62.4%.

Melting Point (°C.): 182.0–183.5 (light yellow fine particles, recrystallized from ethyl acetate and hexane)

$^1$HNMR (300 MHz, CDCl$_3$): δ 1.00–1.09 (m, 2H), 1.12–1.18 (m, 2H), 1.35–1.40 (m, 1H), 1.48–1.55 (m, 7H), 1.62–1.84 (m, 4H), 2.47 (dd, J=16.0 and 5.0 Hz, 1H), 2.56 (dd, J=16.0 and 5.4 Hz, 1H), 2.75–2.88 (m, 3H), 3.03 (s, 2H), 3.71 (s, 3H), 3.85–3.94 (m, 1H), 4.16–4.18 (m, 1H), 4.25–4.36 (m, 1H), 4.40–4.42 (m, 1H), 6.86 (s, 1H), 6.94–6.99 (m, 2H), 7.13 (broad s, 2H), 7.54 7.61 (m, 2H) ppm IR (KBr): 3504, 2980, 2932, 1732 cm$^{-1}$ Mass (m/z, %): 479 (M+, 77), 429 (100), 302 (58), 288 (10), 69 (7), 44 (9)

EXAMPLE 44

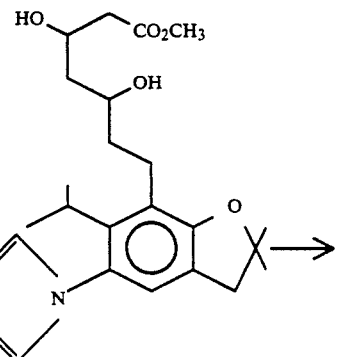

(78)

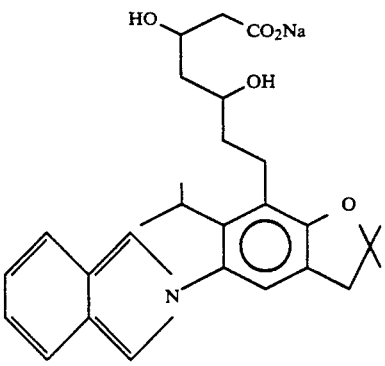

(79)

14 mg (0.029 mmol) of the Compound No. 78 synthesized in Example 43 was dissolved in 2 ml of ethanol. After the addition of 0.29 ml (0.029 mmol) of 0.1N sodium hydroxide, the thus obtained mixture was stirred in an atmosphere of argon gas at room temperature for 40 minutes. This reaction mixture was then concentrated, dissolved in water, and lyophilized, whereby sodium 7-[2,3-dihydro-5-isoindolyl-2,2-dimethyl-6-(propan-2-yl)benzo[b]furan-7-yl]-3,5-dihydroxyheptanoate (Compound No. 79) was obtained as a colorless amorphous solid in a yield of 100%.

$^1$HNMR (300 MHz, CD$_3$OD): δ 1.10–1.20 (m, 6H), 1.50 (s, 6H), 1.66–1.88 (m, 4H), 2.31 (dd, J=15.1 and 7.7 Hz, 1H), 2.41 (dd, J=15.1 and 5.0 Hz, 1H), 2.60–2.82 (m, 2H), 2.87–2.98 (m, 1H), 3.02 (s with fine coupling, 2H), 3.87–3.96 (m, 1H), 4.12–4.22 (m, 1H), 6.82–6.91 (m, 3H), 7.12 (s, 2H), 7.46–7.53 (m, 2H) ppm IR (KBr): 3448, 2968, 1574 cm$^{-1}$ Mass (FAB-neg, m/z, %): 486 ([M-H]$^-$, 14), 464 (100), 360 (18), 330 (8), 316 (11), 304 (5), 116 (76), 85 (15)

REFERENCE EXAMPLE 27

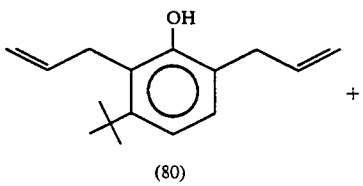

(80)

+

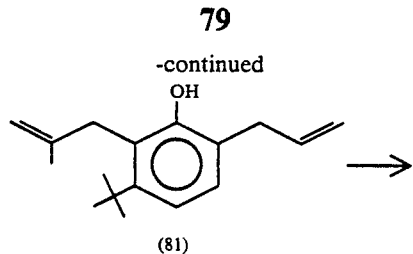

(81)

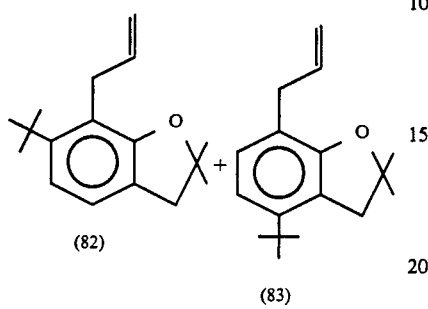

(82) (83)

32.9 g (135 mmol) of a mixture of 3-(t-butyl)-6-(2-methyl-2-propen-1-yl)-2-(2-propen-1-yl)phenol (Compound No. 80) and 3-(t-butyl)-2-(2-methyl-2-propen-1-yl)-6-(2-propen-1-yl)phenol (Compound No. 81) at a ratio of 9:1 was added to 180 ml of 1,2-dichloroethane, and stirred in an atmosphere of argon gas at 0° C. After the addition of 5.0 ml (39.2 mmol) of boron trifluoride etherate, the thus obtained mixture was further stirred for 1 hour and 35 minutes. 5.0 ml (39.2 mmol) of boron trifluoride etherate was further added to the above mixture. The reaction mixture was then stirred for 1 hour and 25 minutes, poured into an aqueous solution of potassium carbonate, and extracted with ethyl acetate. The thus obtained extract layer was washed with a saturated aqueous solution of sodium chloride three times, dried over magnesium sulfate and concentrated. The thus obtained concentrated material was chromatographed on a silica gel column, and eluted with a mixed solvent of hexane and methylene chloride at a ratio of 20:1, whereby 19.9 g of a mixture of 6-(t-butyl)-2,3-dihydro-2,2-dimethyl-7-(2-propen-1-yl)benzo[b]furan (Compound No. 82) and 4-(t-butyl)-2,3-dihydro-2,2-dimethyl-7-(2-propen-1-yl)benzo[b]furan (Compound No. 83) at a ratio of 13:1 was obtained as a colorless oily material in a yield of 60.5%. Subsequently, 8.80 g of a mixture of the same Compounds as mentioned above at a ratio of 5:1 was obtained in a yield of 26.8%.

(A mixture of the Compound No. 82 and the Compound No. 83 at a ratio of 13:1)

$^1$HNMR (CDCl$_3$, 300 MHz): δ 1.31 (s, 0.64H), 1.38 (s, 8.36H), 1.43 (s, 5.57H), 1.45 (s, 0.43H), 2.97 (s with fine coupling, 1.86H), 3.17 (s, 0.14H), 3.29 (broad d, J=6.7 Hz, 0.14H), 3.59 (ddd, J=5.6, 1.8 and 1.7 Hz, 1.86H), 4.93 (ddd, J=17.2, 3.6 and 1.8 Hz, 0.93H), 4.98 (ddd, J=10.3, 3.6 and 1.7 Hz, 0.93H), 4.98-5.12 (m, 0.14H), 6.00 (ddt, J=17.2, 10.3 and 5.6 Hz, 0.93H), 5.92-6.08 (m, 0.07H), 6.78 (d, J=8.0 Hz, 0.07H), 6.86 (d, J=7.9 Hz, 0.93H), 6.93 (d, J=7.9 Hz, 0.93H), 6.83 6.96 (m, 0.07H) ppm

REFERENCE EXAMPLE 28

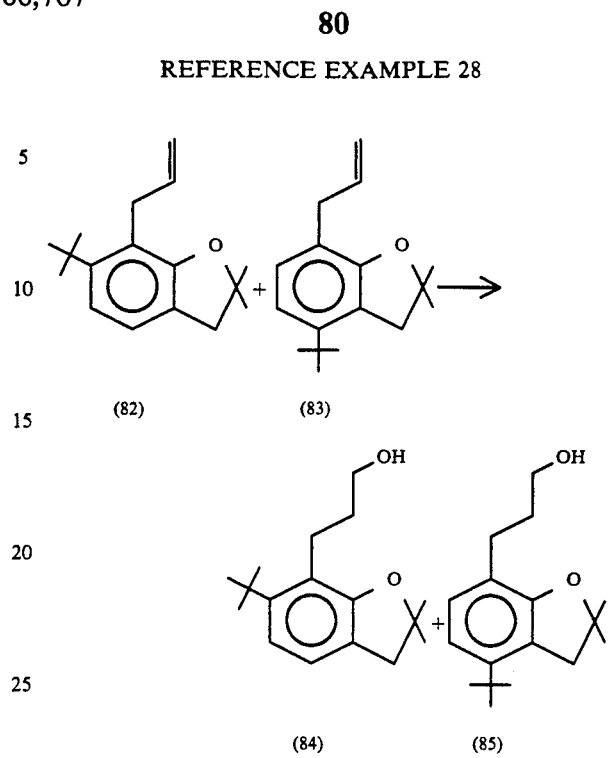

5.00 g (20.5 mmol) of the mixture of the Compound No. 82 and the Compound No. 83 synthesized in Reference Example 27 at a ratio of 13:1 was added to 30.0 ml of anhydrous THF and then stirred in an atmosphere of argon gas at 0° C. After the addition of 3.75 g (15.4 mmol) of 9-BBN-dimer, the thus obtained mixture was further stirred at room temperature for 2 hours and 15 minutes, and cooled to 0° C. 26.0 ml of ethanol, 45.0 ml of 2N sodium hydroxide and 32.0 ml (282 mmol) of a 30% aqueous hydrogen peroxide were successively added to the above mixture and stirred at room temperature for 1 hour and 50 minutes.

The reaction mixture was poured into 1N hydrochloric acid and extracted with ethyl acetate. The thus obtained extract layer was washed successively with a saturated aqueous solution of sodium chloride, an aqueous solution of sodium thiosulfate and a saturated aqueous solution of sodium chloride twice, dried over magnesium sulfate, and concentrated. The thus obtained concentrated material was chromatographed on a silica gel column, and eluted with a mixed solvent of hexane and ethyl acetate at a ratio of 2:3, whereby 3.44 g of 3-[6-(t-butyl)-2,3-dihydro-2,2-dimethylbenzo[b]furan-7-yl]propanol (Compound No. 84) was obtained as a colorless oily material in a yield of 64.1%. Furthermore, 929 mg of a mixture of Compound No. 84 and 3-[4-(t-butyl)-2,3-dihydro-2,2-dimethylbenzo[b]furan-7-yl]propanol (Compound No. 85) at a ratio of 5:1 was obtained in a yield of 17.3%.

$^1$HNMR (CDCl$_3$, 300 MHz): δ 1.40 (s, 9H), 1.47 (s, 6H), 1.80-1.95 (m, 2H), 2.08 (t, J=6.0 Hz, 1H), 2.83-2.94 (m, 2H), 2.98 (s with fine coupling, 2H), 3.71 (td, J=6.1 and 6.0 Hz, 2H), 6.87 (d, J=8.0 Hz, 1H), 6.92 (d, J=8.0 Hz, 1H) ppm IR (liquid film): 3356, 2972 cm$^{-1}$ Mass (m/z, %): 262 (M$^+$, 100), 217 (30), 203 (58), 161 (27)

REFERENCE EXAMPLE 29

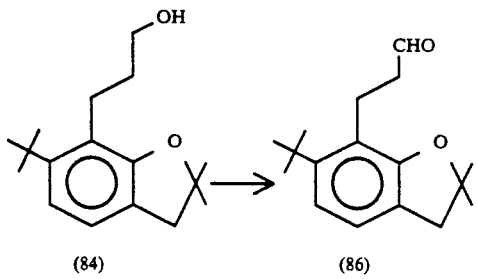

3.06 g (11.7 mmol) of a mixture of the Compound No. 84 and the Compound No. 85 synthesized in Reference Example 28 at a ratio of 13:1 was dissolved in a solvent containing 38.0 ml of dimethyl sulfoxide and 8.0 ml of anhydrous THF. To this mixture, 5.7 ml (41.0 mmol) of triethylamine was added. After the addition of 5.50 g (34.6 mmol) of sulfur trioxide pyridine complex, the thus obtained mixture was stirred in an atmosphere of argon gas at room temperature for 1 hour. The reaction mixture was poured into 1N hydrochloric acid and extracted with ethyl acetate. The thus obtained extract layer was washed successively with a saturated aqueous solution of sodium chloride, a saturated aqueous solution of sodium hydrogencarbonate and a saturated aqueous solution of sodium chloride twice, dried over magnesium sulfate, and concentrated. The thus obtained concentrated material was crystallized from hexane, whereby 1.10 g of 3-[6-(t-butyl)-2,3-dihydro-2,2-dimethylbenzo[b]furan-7-yl]propanal (Compound No. 86) was obtained in a yield of 39.0%. Furthermore, the filtrate was concentrated, chromatographed on a silica gel column, and eluted with a mixed solvent of hexane and ethyl acetate at a ratio of 100:7, whereby 715 mg of the Compound No. 86 was obtained in a yield of 25.3%.

Melting Point (°C.): 79.5–80.0 (colorless fine particles, recrystallized from hexane)

$^1$HNMR (300 MHz, CDCl$_3$): δ 1.38 (s, 9H), 1.45 (s, 6H), 2.73–2.83 (m, 2H), 2.97 (s with fine coupling, 2H), 3.06–3.16 (m, 2H), 6.85 (d, J=7.9 Hz, 1H), 6.93 (d, J=8.0 Hz, 1H), 9.89 (t, J=1.3 Hz, 1H) ppm IR (KBr): 2968, 2928, 1722 cm$^{-1}$ Mass (m/z, %): 260 (M+, 100), 217 (38), 204 (60), 203 (59), 161 (45), 159 (35), 149 (35), 57 (32)

REFERENCE EXAMPLE 30

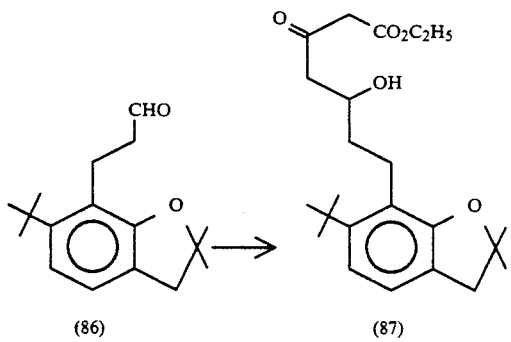

101 mg (2.53 mmol) of a 60% sodium hydride was suspended in 5.0 ml of anhydrous THF in an atmosphere of argon gas at 0° C. After the addition of 0.32 ml (2.53 mmol) of ethyl acetoacetate, the thus obtained mixture was stirred for 30 minutes. Subsequently, 1.59 ml (2.48 mmol) of a 15% hexane solution of butyl lithium was added to the above mixture. This mixture was stirred for 15 minutes and cooled to −78° C. After the addition of 496 mg (19.0 mmol) of the Compound No. 86 synthesized in Reference Example 29, the thus obtained reaction mixture was stirred for 1 hour and 20 minutes.

After the completion of the reaction, the above reaction mixture was poured into 1N hydrochloric acid and extracted with ethyl acetate. The thus obtained extract layer was washed successively with water, a saturated aqueous solution of sodium hydrogencarbonate and a saturated aqueous solution of sodium chloride twice, dried over magnesium sulfate, and concentrated. The thus obtained concentrated material was chromatographed on a silica gel column, and eluted with a mixed solvent of hexane and ethyl acetate at a ratio of 10:3, whereby 492 mg of ethyl 7-[6-(t-butyl)-2,3-dihydro-2,2-dimethylbenzo[b]furan-7-yl]-5-hydroxy-3-oxoheptanoate (Compound No. 87) was obtained as a colorless amorphous solid in a yield of 66.6%.

$^1$HNMR (CDCl$_3$m 300 MHz): δ 1.28 (t, J=7.1 Hz, 3H), 1.39 (s, 9H), 1.46 (s, 6H), 1.66–1.88 (m, 2H), 2.74 (d, J=6.0 Hz, 2H), 2.72–2.88 (m, 1H), 2.92–3.07 (m, 1H), 2.97 (s with fine coupling, 2H), 3.14 (d, J=3.8 Hz, 1H), 3.51 (s, 2H), 4.12–4.25 (m, 1H), 4.20 (q, J=7.1 Hz, 2H), 6.86 (d, J=8.0 Hz, 1H), 6.91 (d, J=8.0 Hz, 1H) ppm IR (KBr): 3540, 2976, 1746, 1714 cm$^{-1}$ Mass (m/z, %): 390 (M+, 67), 372 (26), 260 (37), 217 (100), 204 (32), 203 (33), 201 (36), 175 (31), 161 (39), 159 (29)

EXAMPLE 45

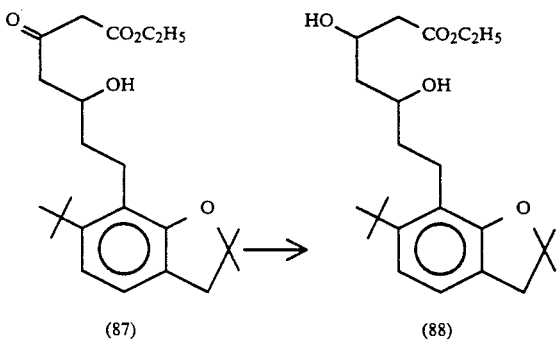

10.2 ml (10.2 mmol) of a 1.0M THF solution of triethylborane was added to 39 mg (0.38 mmol) of pivalic acid in an atmosphere of argon gas, at room temperature followed by stirring for 1 hour. To this mixture, a solution of 3.00 g (7.69 mmol) of the Compound No. 87 synthesized in Reference Example 30 in 30 ml of anhydrous THF was added. The reaction mixture was then stirred for 1 hour and cooled to −78° C. Furthermore, 15.0 ml of methanol and 300 mg (7.93 mmol) of sodium borohydride were successively added to the above reaction mixture, followed by stirring for 2 hours.

The thus obtained reaction mixture was gradually added to a solution of 45.0 ml of a 30% aqueous hydrogen peroxide at 0° C., and stirred at room temperature for 2 hours and 30 minutes. The reaction mixture was poured into 1N hydrochloric acid and extracted with ethyl acetate. The thus obtained extract layer was washed successively with a saturated aqueous solution of sodium chloride, a saturated aqueous solution of sodium hydrogencarbonate and a saturated aqueous solution of sodium chloride twice, dried over magnesium sulfate, and concentrated. The thus obtained concentrated material was chromatographed on a silica gel column, and eluted with a mixed solvent of hexane and ethyl acetate at a ratio of 2:1, whereby 2.91 g of ethyl 7-[6-(t-butyl)-2,3-dihydro-2,2-dimethylbenzo[b]furan-7-yl]-3,5-dihydroxyheptanoate (Compound No. 88) was obtained as a colorless oily material in a yield of 96.4%.

¹HNMR (CDCl₃, 300 MHz): δ 1.27 (t, J=7.2 Hz, 3H), 1.40 (s, 9H), 1.46 (s, 3H), 1.48 (s, 3H), 1.59–1.67 (m, 2H), 1.68–1.85 (m, 2H), 2.45 (dd, J=16.0 and 5.0 Hz, 1H), 2.53 (dd, J=16.0 and 7.6 Hz, 1H), 2.76–3.04 (m, 2H), 2.99 (s, 2H), 3.77 (d, J=2.9 Hz, 1H), 3.88–4.02 (m, 1H), 4.16 (q, J=7.2 Hz, 2H), 4.23–4.37 (m, 1H), 6.88 (d, J=8.0 Hz, 1H), 6.92 (d, J=8.0 Hz, 1H) ppm IR (liquid film): 3452, 2976, 1738 cm⁻¹

Mass (m/z, %): 392 (M⁺, 100), 374 (65), 328 (97.4), 295 (30), 217 (78), 201 (45), 187 (31), 161 (49), 57 (38)

EXAMPLE 46

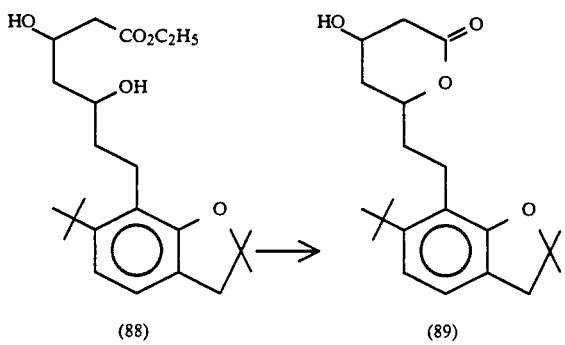

(88) → (89)

5.99 g (15.3 mmol) of the Compound No. 88 synthesized in Example 45 was dissolved in 30 ml of methanol. To this solution, 22.9 ml (22.9 mmol) of 1N sodium hydroxide was added. The thus obtained mixture was stirred in an atmosphere of argon gas at 0° C. for 2 hours, and further stirred overnight at room temperature. The reaction mixture was then poured into 1N hydrochloric acid and extracted with ethyl acetate. The thus obtained extract layer was washed successively with water and a saturated aqueous solution of sodium chloride, dried over magnesium sulfate and concentrated. The thus obtained concentrated material was dissolved in 50 ml of ethyl acetate. To this solution, 4.80 ml (62.3 mmol) of trifluoroacetic acid was added and stirred at room temperature for 30 minutes. The reaction mixture was poured into an aqueous solution of diluted sodium hydrogencarbonate, and extracted with ethyl acetate. The thus obtained extract layer was washed successively with water and a saturated aqueous solution of sodium chloride, dried over magnesium sulfate, and concentrated. The thus obtained concentrated material was chromatographed on a silica gel column, and eluted with a mixed solvent of ethyl acetate and hexane at a ratio of 2:1, whereby 961 mg of trans-(±)-6-[6-(t-butyl)-2,3-dihydro-2,2-dimethylbenzo[b]furan-7-yl]ethyl-4-hydroxytetrahydropyran-2-one (Compound No. 89) was obtained in a yield of 87.9%.

Melting Point (0C): 128.5–129.0 (colorless fine particles, recrystallized from ethyl acetate and hexane)

¹HNMR (300 MHz, CDCl₃): δ 1.40 (s, 9H), 1.44 (s, 3H), 1.45 (s, 3H), 1.80–2.11 (m, 5H), 2.65 (ddd, J=17.6, 4.0 and 1.6 Hz, 1H), 2.79 (dd, J=17.6 and 5.1 Hz, 1H), 2.78–2.87 (m, 1H), 2.96 (s with fine coupling, 2H), 3.02–3.13 (m, 1H), 4.40–4.48 (m, 1H), 4.78–4.89 (m, 1H), 6.85 (d, J=8.0 Hz, 1H), 6.92 (d, J=8.0 Hz, 1H) ppm IR (KBr): 3448, 3032, 2972, 1714 cm⁻¹

Mass (m/z, %): 346 (M⁺, 100), 328 (84), 217 (62), 201 (64), 159 (37), 57 (27)

EXAMPLE 47

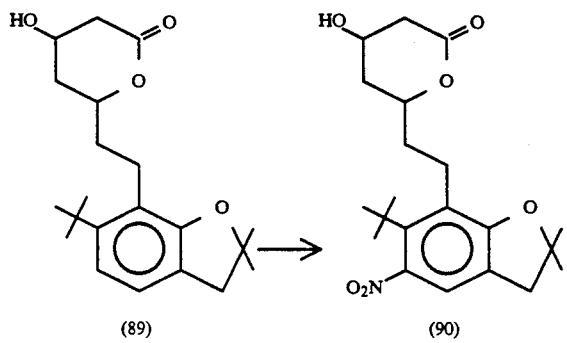

(89) → (90)

258 mg (0.746 mmol) of the Compound No. 89 synthesized in Example 46 was dissolved in 5 ml of acetic acid. To this solution, 0.56 ml (1.12 mmol) of a 2M nitric acid in acetic acid was added. Subsequently, with the addition of 5 mg (0.075 mmol) of sodium nitrite, the thus obtained mixture was stirred at room temperature for 1 hour and 20 minutes. After the addition of 0.2 ml (0.40 mmol) of a 2M nitric acid in acetic acid, the reaction mixture was further stirred for 1 hour and 40 minutes, poured into water, and extracted with ethyl acetate. The thus obtained extract layer was washed successively with a saturated aqueous solution of sodium hydrogencarbonate and a saturated aqueous solution of sodium chloride, dried over magnesium sulfate, and concentrated. The thus obtained concentrated material was chromatographed on a silica gel column, and eluted with a mixed solvent of ethyl acetate and hexane at a ratio of 2:1, whereby 251 mg of trans-(±)-6-[6-(t-butyl)-2,3-dihydro-2,2-dimethyl-5-nitrobenzo[b]furan-7-yl]ethyl-4-hydroxytetrahydropyran-2-one (Compound No. 90) was obtained in a yield of 86.1%.

Melting Point (°C.): 130.0–131.0 (yellow fine particles, recrystallized from ethyl acetate and hexane)

¹HNMR (300 MHz, CDCl₃): δ 1.46 (s, 15H), 1.78–2.09 (m, 5H), 2.66 (ddd, J=17.6, 3.8 and 1.6 Hz, 1H), 2.75–2.89 (m, 2H), 2.98 (s with fine coupling, 2H), 3.09–3.21 (m, 1H), 4.40–4.49 (m, 1H), 4.77–4.88 (m, 1H), 6.98 (s, 1H) ppm IR (KBr): 3464, 2968, 1740, 1716, 1522 cm⁻¹

Mass (m/z, %): 391 (M⁺, 100), 374 (63), 361 (32), 344 (29), 230 (28), 214 (33), 199 (33), 129 (24), 57 (29)

EXAMPLE 48

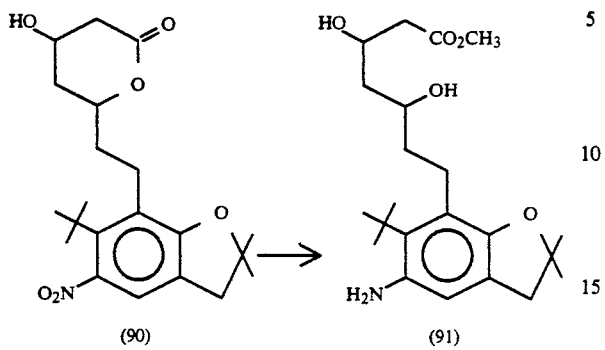

1.11 g of the Compound No. 90 synthesized in Example 47 was dissolved in 10 ml of methanol. After the addition of 420 mg of platinum oxide, the thus obtained mixture was stirred in an atmosphere of hydrogen at room temperature for 3 hours and 50 minutes. The reaction mixture was diluted with ethyl acetate and filtered through a Celite. The thus obtained filtrate was concentrated, chromatographed on a silica gel column, and eluted with a mixed solvent of ethyl acetate and hexane at a ratio of 1:1, and then with ethyl acetate, whereby 772 mg of methyl 7-[5-amino-6-(t-butyl)-2,3-dihydro-2,2-dimethylbenzo[b]furan-7-yl]-3,5-dihydroxyheptanoate (Compound No. 91) was obtained as a yellow oily material in a yield of 75.7%.

$^1$HNMR (300 MHz, CDCl$_3$): δ 1.43 (s, 3H), 1.46 (s, 3H), 1.57 (s, 9H), 1.58-1.75 (m, 4H), 2.42 (dd, J=15.5 and 5.3 Hz, 1H), 2.53 (dd, J=15.5 and 7.6 Hz, 1H), 2.82-2.94 (m, 1H), 2.94 (s, 2H), 3.04-3.16 (m, 1H), 3.51-3.63 (m, 2H), 3.69 (s, 3H), 3.69-3.80 (m, 1H), 4.13-4.18 (m, 1H), 4.20-4.30 (m, 1H), 4.42 (broad s, 1H), 6.40 (s, 1H) ppm IR (liquid film): 3476, 2954, 1735, 1628 cm$^{-1}$ Mass (m/z, %): 393 (M$^+$, 100), 343 (82), 216 (61), 177 (35), 176 (45)

EXAMPLE 49

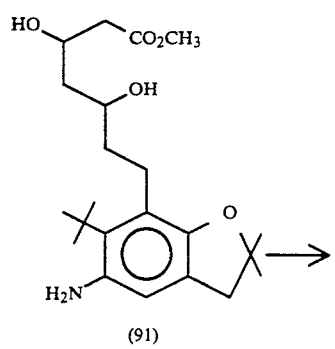

992 mg (3.76 mmol) of α,α'-dibromo-o-xylene and 1.04 g (7.53 mmol) of potassium carbonate were added to 10 ml of anhydrous DMF and then stirred. To thus mixture, a solution of 985 mg (2.51 mmol) of the Compound No. 91 synthesized in Example 48 in 10 ml of anhydrous DMF was added dropwise over a period of 2 hours. Furthermore, the above mixture was stirred for 1 hour and 30 minutes, poured into water, and extracted with ethyl acetate. The thus obtained extract layer was washed with a saturated aqueous solution of sodium chloride, dried over magnesium sulfate, and concentrated. The thus obtained concentrated material was chromatographed on a silica gel column, and eluted with a mixed solvent of ethyl acetate and hexane at a ratio of 2:1, and then with ethyl acetate, whereby 1.05 g of methyl 7-[6-(t-butyl)-2,3-dihydro-5-(isoindolin-2-yl)-2,2-dimethylbenzo[b]furan-7-yl]-3,5-dihydroxyheptanoate (Compound No. 92) was obtained in a yield of 84.4%.

Melting Point (°C.): 138.0-139.0 (colorless fine particles, recrystallized from ethyl acetate and hexane)

$^1$HNMR (300 MHz, CDCl$_3$): δ 1.46 (s, 3H), 1.48 (s, 3H), 1.57 (s, 6H), 1.57 (s, 9H), 1.52-1.67 (m, 2H), 1.72-1.83 (m, 2H), 2.47 (dd, J=15.8 and 5.0 Hz, 1H), 2.56 (dd, J=15.8 and 7.7 Hz, 1H), 2.84-2.95 (m, 1H), 2.95 (s, 2H), 2.99-3.10 (m, 1H), 3.71 (s, 3H), 3.79-3.81 (m, 1H), 3.83-3.95 (m, 1H), 4.23 (broad s, 1H), 4.27-4.44 (m, 3H), 4.46-4.53 (m, 2H), 7.09 (s, 1H), 7.20-7.30 (m, 4H) ppm IR (KBr): 3652, 3512, 2952, 1722 cm$^{-1}$ Mass (m/z, %): 495 (M$^+$, 99), 445 (100), 388 (37), 333 (43), 279 (41), 278 (37), 57 (18), 44 (25)

EXAMPLE 50

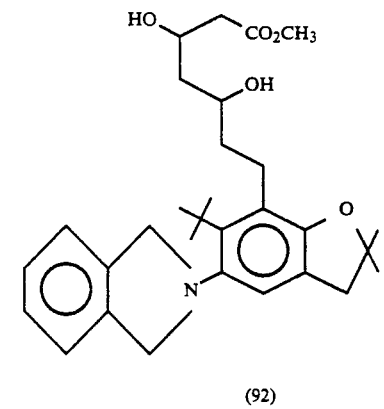

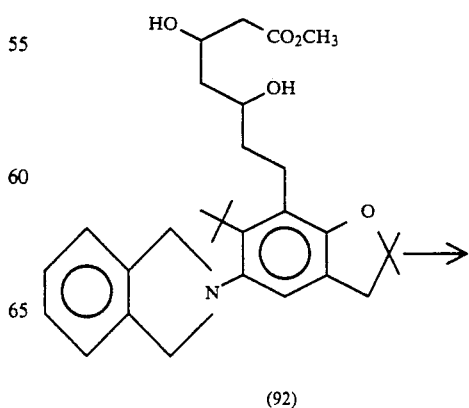

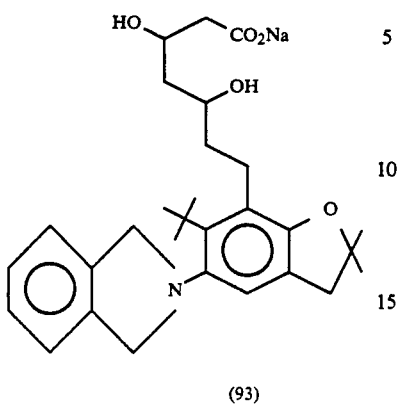

(93)

549 mg (1.11 mmol) of the Compound No. 92 synthesized in Example 49 was dissolved in a mixed solvent containing 5 ml of ethanol and 1 ml of water. 1.11 ml (1.11 mmol) of 1N sodium hydroxide was added to the above solution, followed by stirring at room temperature for 3 hours and 20 minutes. Thereafter, the above reaction mixture was concentrated, whereby crystals of sodium 7-[6-(t-butyl)-2,3-dihydro-5-(isoindolin-2-yl)-2,2-dimethylbenzo[b]furan-7-yl]-3,5-dihydroxyheptanoate (Compound No. 93) was obtained in a Melting Point (°C.): 218.0-219.0 (colorless fine particles, partially decomposed at 215° C.)

1HNMR (300 MHz, CD3OD): δ 1.43 (s, 3H), 1.44 (s, 3H), 1.56 (s, 9H), 1.62-1.80 (m, 4H), 2.30 (dd, J=15.1 and 7.7 Hz, 1H), 2.41 (dd, J=15.1 and 4.9 Hz, 1H), 2.75-2.88 (m, 1H), 2.93 (s with fine coupling, 2H), 2.97-3.10 (m, 1H), 3.82-3.93 (m, 1H), 4.12-4.24 (m, 1H), 4.30-4.44 (m, 4H), 7.06 (s, 1H), 7.21 (s, 4H) ppm IR (KBr): 3448, 2952, 1574 cm$^{-1}$ Mass (FAB-neg, m/z, %): 502 ([M-H]$^-$, 24), 480 (100), 466 (26), 376 (13), 318 (6), 262 (6), 116 (40), 85 (20)

EXAMPLE 51

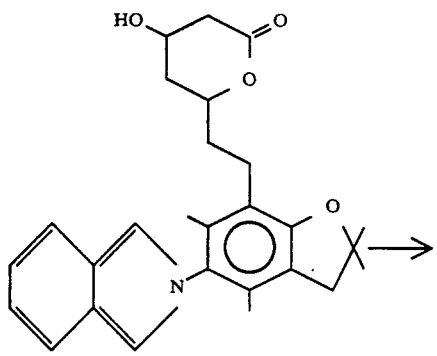

(14)

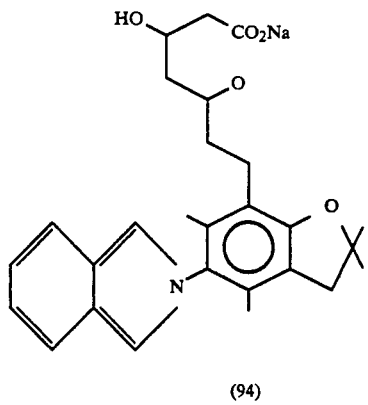

(94)

604 mg (1.30 mmol) of the Compound No. 14 synthesized in Example 7 was dissolved in a mixed solvent of 5 ml of methanol and 5 ml of water. 1.30 ml (1.30 mmol) of 1N sodium hydroxide was added to the above solution, followed by stirring in an atmosphere of argon gas at room temperature for 2 hours and 30 minutes. After the addition of 5 ml of methanol and 5 ml of water, the thus obtained mixture was further stirred for 2 hours, concentrated, dissolved in water, and lyophilized, whereby sodium 7-[2,3-dihydro-5-isoindolyl-2,2,4,6-tetramethylbenzo[b]furan-7-yl]-3,5-dihydroxyheptanoate (Compound No. 94) was obtained as a colorless amorphous solid in a yield of 100%.

1HNMR (300 MHz, CD3OD): δ 1.50 (s, 6H), 1.60-1.70 (m, 4H), 1.76 (s, 3H), 1.81 (s, 3H), 2.28 (dd, J=15.1 and 7.6 Hz, 1H), 2.38 (dd, J=15.1 and 5.0 Hz, 1H), 2.60-2.82 (m, 2H), 2.99 (s, 2H), 3.77-3.87 (m, 1H), 4.09-4.20 (m, 1H), 6.87 (dd, J=6.6 and 3.0 Hz, 2h), 7.02 (s, 2H), 7.52 (dd, J=6.6 and 3.0 Hz, 2H) ppm IR (KBr): 3436, 2976, 2928, 1568 cm$^{-1}$ Mass (FAB-neg, m/z, %): 472 ([M-H]$^-$, 25), 450 (100), 368 (15), 346 (21), 302 (9), 290 (7), 157 (9), 116 (49), 85 (11)

[Test 1] Measurement of Inhibitory Activity on HMG-CoA Reductase

The inhibition effect on HMG-CoA Reductase of each of representative examples of the 4-hydroxytetrahydropyran-2-one and 3,5-dihydroxyheptanoic acid derivatives prepared in the above-discussed examples was measured in accordance with the method described in Journal of Biological Chemistry (J. Biol. Chem.) Vol. 234, page 2835 (1959) in order to investigate the inhibitory activity of each derivative in terms of the activity ratio of the biosynthesis of cholesterol. The results are shown in the following Table 1:

TABLE 1

| Activity ratio of Biosynthesis of Cholesterol | |
|---|---|
| Example (Compound No.) | Reactive Inhibitory Potency (a) |
| 6 (12) | 1500 |
| 7 (13) | 250 |
| 7 (14) | 250 |
| 8 (15) | 830 |
| 28 (43) | 170 |
| 41 (76) | 2730 |
| 51 (94) | 1550 |
| Compactin (ML-236B) | 100 |

(a) Relative value when the value of Compactin is 100.

(a) Relative value when the value of Compactin is 100.

[Test 2] Measurement of Reduction in Cholesterol Value

By use of model rats with Triton-induced hyperlipemia, prepared in accordance with a method by Endo et al. (Endo, A., Thujita, K., Kuroda, M., and Tanzwas, K., Biochem. Biophys. Acta, 575, 266 (1979), the effect of the reduction in total serum cholesterol was investigated, using the value of Compactin (ML-236B) as a reference. The results are shown in Table 2:

TABLE 2

| Example (Compound No.) | Reduction of Cholesterol Value |
| --- | --- |
| 6 (12) | 330 |
| 7 (13) | 180 |
| 7 (13) | 160 |
| 8 (15) | 320 |
| Compactin (ML-236B) | 100 |

[Test 3] Measurement of Anti-oxidation Function

The anti-oxidation function of some examples of the 4-hydroxytetrahydropyran-2-one and 3,5-dihydroxyheptanoic acid derivatives prepared in the above-discussed examples was measured as a reference of the inhibition function of the automatic TBARS reproduction of the rat brain homogenate in accordance with the method described in Nippon Yakuri Gakkai-shi 87, 427–434 (1986) by K. Shintomi et al.

The anti-oxidation function of each of the tested samples was as follows:

TABLE 3

| Example (Compound No.) | Anti-oxidation Function $IC_{50}$ (M) |
| --- | --- |
| 4 (10) | $2.75 \times 10^{-6}$ |
| 6 (12) | $1.58 \times 10^{-6}$ |
| 7 (13) | $1.44 \times 10^{-6}$ |
| 7 (14) | $1.67 \times 10^{-6}$ |
| 8 (15) | $1.67 \times 10^{-6}$ |
| 10 (17) | $1.49 \times 10^{-6}$ |
| 17 (24) | $1.63 \times 10^{-6}$ |
| 41 (76) | $6.5 \times 10^{-6}$ |
| 44 (79) | $3.26 \times 10^{-6}$ |
| 50 (93) | $2.0 \times 10^{-6}$ |
| 51 (94) | $2.27 \times 10^{-6}$ |

What is claimed is:

1. 4-hydroxytetrahydropyran-2-one derivative of formula (I):

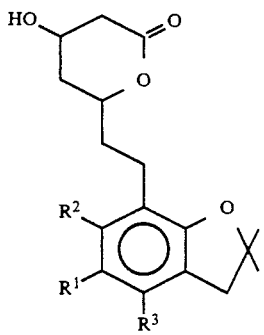

(I)

wherein $R^1$ represents hydrogen, a nitro group, or $-N(R^4)R^5$ in which $R^4$ and $R^5$ each represent a straight chain or branched chain alkyl group having 1 to 5 carbon atoms; an alkenyl group having 2 to 5 carbon atoms; an aryl group selected from the group consisting of furyl group, thienyl group, pyrrolyl group, phenyl group and pyridyl group; an aralkyl group selected from the group consisting of benzyl group, phenethyl group, phenylpropyl group, naphthylmethyl group, furfuryl group, and thienylmethyl group; an acyl group having 2 to 5 carbon atoms; an aroyl group selected from the group consisting of benzoyl group, pyridinecarbonyl group, imidazolylcarbonyl group, furoyl group, and thiophenecarbonyl group; a carbamoyl group; or a thiocarbamoyl group; and $R^4$ and $R^5$ may be combined to form a cyclic amino group; and $R^2$ and $R^3$ each represent hydrogen or a straight chain or branched chain alkyl group having 1 to 5 carbon atoms.

2. The 4-hydroxytetrahydropyran-2-one derivative as claimed in claim 1, wherein said straight chain or branched chain alkyl group represented by $R^4$ or $R^5$ in formula (I) is selected from the group consisting of methyl group, ethyl group, propyl group, isopropyl group, butyl group, isobutyl group, s-butyl group, and pentyl group.

3. The 4-hydroxytetrahydropyran-2-one derivative as claimed in claim 1, wherein said alkenyl group represented by $R^4$ or $R^5$ in formula (I) is selected from the group consisting of ethylene group, 1-propenyl group, 2-propenyl group, 2-methyl-1-propenyl group, 2-methyl-2-propenyl group, 1-butenyl group, 2-butenyl group, 3-butenyl group, and prenyl group.

4. The 4-hydroxytetrahydropyran-2-one derivative as claimed in claim 1, wherein said acyl group represented by $R^4$ or $R^5$ in formula (I) is selected from the group consisting of acetyl group, propionyl group, butyryl group, isobutyryl group, and pivaloyl group.

5. The 4-hydroxytetrahydropyran-2-one derivative as claimed in claim 1, wherein said carbamoyl group represented by $R^4$ or $R^5$ in formula (I) is a substituted carbamoyl group selected from the group consisting of methylcarbamoyl group, dimethylcarbamoyl group, ethylcarbamoyl group, diethylcarbamoyl group, phenylcarbamoyl group, and cyclohexylcarbamoyl group.

6. The 4-hydroxytetrahydropyran-2-one derivative as claimed in claim 1, wherein said thiocarbamoyl group represented by $R^4$ or $R^5$ in formula (I) is a substituted thiocarbamoyl group selected from the group consisting of methylthiocarbamoyl group, dimethylthiocarbamoyl group, ethylthiocarbamoyl group, diethylthiocarbamoyl group, phenylthiocarbamoyl group, and cyclohexylthiocarbamoyl group.

7. The 4-hydroxytetrahydropyran-2-one derivative as claimed in claim 1, wherein said cyclic amino group formed by $R^4$ and $R^5$ in combination in formula (I) is selected from the group consisting of pyrrolidine-1-yl group, piperidino group, morpholino group, isoindoline-2-yl group, isoindolyl group, and 1,2,3,4-tetrahydroisoquinoline-2-yl group.

8. 3,5-Dihydroxyheptanoic acid derivative of formula (II):

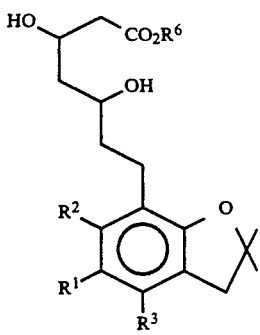

(II)

wherein R¹ represents hydrogen, a nitro group, or —N(R⁴)R⁵ in which R⁴ and R⁵ each represent a straight chain or branched chain alkyl group having 1 to 5 carbon atoms; an alkenyl group having 2 to 5 carbon atoms; an aryl group selected from the group consisting of furyl group, thienyl group, pyrrolyl group, phenyl group and pyridyl group; an aralkyl group selected from the group consisting of benzyl group, phenethyl group, phenylpropyl group, naphthylmethyl group, furfuryl group, and thienylmethyl group; an acyl group having 2 to 5 carbon atoms; an aroyl group selected from the group consisting of benzoyl group, pyridinecarbonyl group, imidazolylcarbonyl group, furoyl group, and thiophene-carbonyl group; a carbamoyl group; or a thiocarbamoyl group; and R⁴ and R⁵ may be combined to form a cyclic amino group;

R² and R³ each represent hydrogen or a straight chain or branched chain alkyl group having 1 to 5 carbon atoms; and R⁶ represents hydrogen, a straight chain or branched chain alkyl group having 1 to 5 carbon atoms, an alkali metal, or an alkaline earth metal.

9. The 3,5-dihydroxyheptanoic acid derivative as claimed in claim 8, wherein said straight chain or branched chain alkyl group represented by R⁴ or R⁵ in formula (II) is selected from the group consisting of methyl group, ethyl group, propyl group, isopropyl group, butyl group, isobutyl group, s-butyl group, and pentyl group.

10. The 3,5-dihydroxyheptanoic acid derivative as claimed in claim 8, wherein said alkenyl group represented by R⁴ or R⁵ in formula (II) is selected from the group consisting of ethylene group, 1-propenyl group, 2-propenyl group, 2-methyl-1-propenyl group, 2-methyl-2-propenyl group, 1-butenyl group, 2-butenyl group, 3-butenyl group, and prenyl group.

11. The 3,5-dihydroxyheptanoic acid derivative as claimed in claim 8, wherein said acyl group represented by R⁴ or R⁵ in formula (II) is selected from the group consisting of acetyl group, propionyl group, butyryl group, isobutyryl group, and pivaloyl group.

12. The 3,5-dihydroxyheptanoic acid derivative as claimed in claim 8, wherein said carbamoyl group represented by R⁴ or R⁵ in formula (II) is a substituted carbamoyl group selected from the group consisting of methylcarbamoyl group, dimethylcarbamoyl group, ethylcarbamoyl group, diethylcarbamoyl group, phenylcarbamoyl group, and cyclohexylcarbamoyl group.

13. The 3,5-dihydroxyheptanoic acid derivative as claimed in claim 8, wherein said thiocarbamoyl group represented by R⁴ or R⁵ in formula (II) is a substituted thiocarbamoyl group selected from the group consisting of methylthiocarbamoyl group, dimethylthiocarbamoyl group, ethylthiocarbamoyl group, diethylthiocarbamoyl group, phenylthiocarbamoyl group, and cyclohexylthiocarbamoyl group.

14. The 3,5-dihydroxyheptanoic acid derivative as claimed in claim 8, wherein said cyclic amino group formed by R⁴ and R⁵ in combination in formula (II) is selected from the group consisting of pyrrolidine-1-yl group, piperidino group, morpholino group, isoindoline-2-yl group, isoindolyl group, and 1,2,3,4-tetrahydroiso-quinoline-2-yl group.

15. The 3,5-dihydroxyheptanoic acid derivative as claimed in claim 8, wherein said straight chain or branched chain alkyl group represented by R⁶ in formula (II) is selected from the group consisting of methyl group, ethyl group, propyl group, isopropyl group, butyl group, isobutyl group, s-butyl group, and pentyl group.

16. The 3,5-dihydroxyheptanoic acid derivative as claimed in claim 8, wherein said alkali metal represented by R⁶ in formula (II) is selected from the group consisting of lithium, sodium, and potassium.

17. The 3,5-dihydroxyheptanoic acid derivative as claimed in claim 8, wherein said alkaline earth metal represented by R⁶ in formula (II) is selected from the group consisting of magnesium, calcium and barium.

* * * * *

UNITED STATES PATENT AND TRADEMARK OFFICE
CERTIFICATE OF CORRECTION

PATENT NO. : 5,266,707
DATED : NOVEMBER 30, 1993
INVENTOR(S) : MASAKATSU MATSUMOTO ET AL

It is certified that error appears in the above-identified patent and that said Letters Patent is hereby corrected as shown below:

Column 1, line 15, "alto relates" should read --also relates--.

Column 1, line 67, "wherein R" should read --wherein $R_1$--.

Column 2, line 44, "of the invention" should read --of the present invention--.

Column 11, line 35, "2.3-dihydro" should read --2,3-dihydro--.

Column 12, line 57 "6-15-(N-benzyl" should read --6-[5-(N-benzyl--.

Column 13, line 57 "as show in" should read --as shown in--.

Column 16, line 60 "1.47 (s, 311)" should read --1.47 (s, 3H)--.

Column 17, line 62, "(q, J=7,1 Hz, 2H)," should read --(q, J=7.1Hz, 2H),--.

UNITED STATES PATENT AND TRADEMARK OFFICE
CERTIFICATE OF CORRECTION

PATENT NO. : 5,266,707
DATED : NOVEMBER 30, 1993
INVENTOR(S) : MASAKATSU MATSUMOTO ET AL

It is certified that error appears in the above-identified patent and that said Letters Patent is hereby corrected as shown below:

Column 18, line 51 "in a yield Subsequently" should read --in a yield of 60.9%.
Subsequently--.

Column 19, line 10, "(m, 1H) 4.65-4.75" should read --(m, 1H), 4.65-4.75--.

Column 19, line 52, "(C°)" should read --(°C)--.

Column 20, line 39, "(C°)" should read --(°C)--.

Column 26, line 39, "No. 17) was" should read --No. 17) was obtained.--.

Column 27, line 38, "yellow oily" should read --yellow oily material.--.

Column 30, line 21, "hours and minutes" should read --hours and 30 minutes--.

Column 31, line 42, "1HNMR" should read --$^1$HNMR--.

UNITED STATES PATENT AND TRADEMARK OFFICE
CERTIFICATE OF CORRECTION

PATENT NO. : 5,266,707
DATED : NOVEMBER 30, 1993
INVENTOR(S) : MASAKATSU MATSUMOTO ET AL

It is certified that error appears in the above-identified patent and that said Letters Patent is hereby corrected as shown below:

Column 32, line 38, "mg of trams" should read --mg of trans--.

Column 32, line 41, "solid in a" should read --solid in a yield of 62.5%.--.

Column 33, line 36, "obtained in a" should read --obtained in a yield of 35.6%.--.

Column 34, line 41, "2,71-2.88" should read --2.71-2.88--.

Column 38, line 7, "(0C)" should read --(°C)--.

Column 39, line 41, "30-minutes" should read --30-minute--.

Column 42, line 50, "of trams" should read --of trans--.

Column 46, line 56, "of trams" should read --of trans--.

Column 48, line 56, "yield of" should read --yield of 78.8%.--.

UNITED STATES PATENT AND TRADEMARK OFFICE
CERTIFICATE OF CORRECTION

PATENT NO. : 5,266,707
DATED : NOVEMBER 30, 1993
INVENTOR(S) : MASAKATSU MATSUMOTO ET AL

It is certified that error appears in the above-identified patent and that said Letters Patent is hereby corrected as shown below:

Column 48, line 61, "2.19 (s. 3H)" should read --2.19 (s, 2H)--.

Column 49, line 62, "2,67" should read --2.67--.

Column 49, line 62, "2,95" should read --2.95--.

Column 51, line 32, "20-minutes" should read --20-minute--.

Column 52, line 33, "10-minutes" should read --10-minute--.

Column 52, line 49, "(m-2fi)" should read --(m, 2H)--.

Column 56, line 52, "successively water" should read --successively with water--.

Column 59, line 4, "propanal" should read --propanol--.

Column 61, line 60, "of 20mi" should read --of 20 mi--.

Column 63, line 31, "propanal" should read --propanol--.

UNITED STATES PATENT AND TRADEMARK OFFICE
CERTIFICATE OF CORRECTION

PATENT NO. : 5,266,707
DATED : NOVEMBER 30, 1993
INVENTOR(S) : MASAKATSU MATSUMOTO ET AL

It is certified that error appears in the above-identified patent and that said Letters Patent is hereby corrected as shown below:

Column 63, line 64, "of a the" should read --of the--.

Column 65, line 12, "yield of" should read --yield of 64.75.--.

Column 65, line 59, "benzo(b]" should read --benzo[b]--.

Column 67, line 54, "yield of" should read --yield of 79.7%.--.

Column 68, line 61, "as an colorless" should read --as a colorless--.

Column 75, line 56, "6 1.38" should read --δ 1.38--.

Column 86, line 25, "2hours" should read --2 hours--.

Column 87, line 32, "obtained in a" should read --obtained in a yield of 100%.--.

Column 89, lines 1 and 2 delete in their entirety.

UNITED STATES PATENT AND TRADEMARK OFFICE
CERTIFICATE OF CORRECTION

PATENT NO. : 5,266,707
DATED : NOVEMBER 30, 1993
INVENTOR(S) : MASAKATSU MATSUMOTO ET AL

It is certified that error appears in the above-identified patent and that said Letters Patent is hereby corrected as shown below:

Column 89, Table 2, "7(13) 160" should read --7(14) 160--.

Column 92, line 34, "$R^6$in" should read --$R^6$ in--.

Column 92, line 41, "$R^6$in" should read --$R^6$ in--.

Signed and Sealed this

Thirty-first Day of January, 1995

Attest:

BRUCE LEHMAN

Attesting Officer    Commissioner of Patents and Trademarks